United States Patent
Witschel et al.

(10) Patent No.: US 9,480,259 B2
(45) Date of Patent: Nov. 1, 2016

(54) PYRAZOLOPYRANS HAVING HERBICIDAL AND PHARMACEUTICAL PROPERTIES

(71) Applicant: BASF SE, Ludwigshafen (DE)

(72) Inventors: Matthias Witschel, Bad Duerkheim (DE); Frank Stelzer, Neuhofen (DE); Johannes Hutzler, Waldsee (DE); Tao Qu, Shanghai (CN); Thomas Mietzner, Annweiler (DE); Klaus Kreuz, Denzlingen (DE); Klaus Grossmann, Tuebingen (DE); Raphael Aponte, Mannheim (DE); Hans Wolfgang Hoeffken, Ludwigshafen (DE); Frederick Calo, Mannheim (DE); Thomas Ehrhardt, Berlin (DE); Anja Simon, Weinheim (DE); Liliana Parra Rapado, Offenburg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/405,942

(22) PCT Filed: May 29, 2013

(86) PCT No.: PCT/EP2013/061115
§ 371 (c)(1),
(2) Date: Dec. 5, 2014

(87) PCT Pub. No.: WO2013/182472
PCT Pub. Date: Dec. 12, 2013

(65) Prior Publication Data
US 2015/0126371 A1 May 7, 2015

Related U.S. Application Data

(60) Provisional application No. 61/656,025, filed on Jun. 6, 2012.

(51) Int. Cl.
*C07D 491/052* (2006.01)
*A01N 43/90* (2006.01)
*C07D 311/94* (2006.01)
*A01N 47/20* (2006.01)

(52) U.S. Cl.
CPC ............ *A01N 43/90* (2013.01); *A01N 47/20* (2013.01); *C07D 311/94* (2013.01); *C07D 491/052* (2013.01)

(58) Field of Classification Search
CPC .................... A01N 43/90; C07D 491/052
See application file for complete search history.

(56) References Cited

PUBLICATIONS

Golubev et al. (CAPLUS Abstract of: Journal of Fluorine Chemistry (2002), 114(1), 63-74).*
International Search Report dated Jun. 24, 2013, prepared in International Application No. PCT/EP2013/061115.
International Preliminary Report on Patentability dated Dec. 9, 2014, prepared in International Application No. PCT/EP2013/061115.
Elgemeie, G.H.,et al. "Synthesis of several arylpyridine and arylpyridazine derivatives", Arch. Pharm. 1989, p. 535-539, vol. 322.
Golubev, A.S., "Synthesis and some heterocyclisation reactions of $CF_2H$-and $CF_2Cl$-substituted 1,1-dicyanoethylenes", Journal of Fluorine Chemistry, 2002, p. 63-74, vol. 114.
Mishriky, N., et al., "Simple synthesis of condensed pyran containing compounds and their antimicrobial properties", Boll. Chim. Farmac., 2001, p. 129-139, vol. 40, No. 3.
Kanagaraj, K., et al. "Solvent-free multicomponent synthesis of pyranopyrazoles: per-6-amino-β-cyclodextrin as a remarkable catalyst and host", Tetrahedron Letters, 2010, p. 3312-3316, vol. 51.

* cited by examiner

*Primary Examiner* — Robert Havlin
(74) *Attorney, Agent, or Firm* — Brinks Gilson & Lione

(57) ABSTRACT

The present invention relates to a pyrazolopyran of the general formula I wherein the variables are defined according to the description, including a tautomer, salt, cleavable prodrug, or mixtures thereof, in particular to said pyrazolopyran for use as a medicament and/or an inhibitor of the enzyme serinehydroxymethyltransferase (SHMT). The invention also relates to a process the preparation of a pyrazolopyran of the formula I, to compositions comprising said compound and processes for the preparation of these compositions. Further it relates to use of the pyrazolopyran of formula I as an herbicide as well as to a method of controlling undesired vegetation.

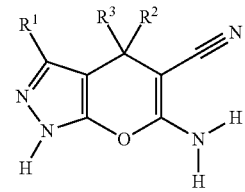

23 Claims, No Drawings

PYRAZOLOPYRANS HAVING HERBICIDAL AND PHARMACEUTICAL PROPERTIES

This application is a National Stage application of International Application No. PCT/EP2013/061115, filed May 29, 2013, which claims the benefit of U.S. Provisional Applicaiotn No. 61/656,025, filed Jun. 6, 2012, the entire contents of which are hereby incorporated herein by reference.

The present invention relates to a pyrazolopyran of the general formula I defined below including a tautomer, salt, cleavable prodrug, or mixture thereof, a process for its preparation and to its use as an herbicide and/or a medicament and/or an inhibitor of the enzyme serinehydroxymethyltransferase (SHMT). Further, the invention relates to an herbicidal composition, a process for its preparation, and to a method for controlling unwanted vegetation as well as to a pharmaceutical composition and a process for its preparation.

Kanagaraj et al, Tetrahedron Lett. 2010, 3312-3316 describes structurally related pyrazolopyrans and their isomers.

Raid et al., Arch. Pharm. Res, 1989, 201-206 and Mishriky et al., Boll. Chim. Farmac, 2001, 129-139 are dealing with certain pyrazolopyrans showing a slight antibacterial activity against some selected bacteria.

The herbicidal properties of known compounds with regard to the harmful plants are not always entirely satisfactory. Furthermore there is a need for novel compounds and compositions for use in treating or preventing parasitic and/or bacterial infections.

It is therefore an object of the present invention to provide compounds having herbicidal and/or pharmaceutical activity. To be provided are in particular compounds which have high herbicidal activity, in particular even at low application rates, and which are sufficiently compatible with crop plants for commercial utilization.

These and further objects are achieved by the pyrazolopyran of formula I

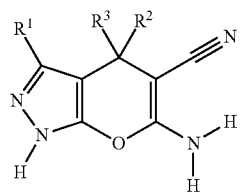

including a tautomer, salt, cleavable prodrug, or mixtures thereof, wherein the variables are as defined below:

$R^1$ is hydrogen, $C_1$-$C_6$-alkyl, $C_3$-$C_6$-cycloalkyl, $C_1$-$C_6$-haloalkyl, $C_3$-$C_6$-halocycloalkyl, $C_1$-$C_6$-hydroxyalkyl, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl, hydroxy, $C_1$-$C_6$-alkoxy, $C_1$-$C_6$-haloalkoxy, $C_3$-$C_6$-cycloalkoxy, $C_3$-$C_6$-alkenyloxy, $C_3$-$C_6$-alkynyloxy, $C_1$-$C_6$-alkylthio, $C_1$-$C_6$-alkylamino, cyano, $R^2$ is $C_2$-$C_6$-alkyl, $C_3$-$C_6$-cycloalkyl, $C_3$-$C_6$-halocycloalkyl, $C_1$-$C_6$-haloalkyl, $C_3$-$C_6$-cycloalkenyl, $C_3$-$C_6$-halocycloalkenyl, $C_1$-$C_6$-hydroxyalkyl, $C_1$-$C_6$-hydroxyhaloalkyl, $C_1$-$C_6$-hydroxycycloalkyl $C_1$-$C_6$-alkoxy-$C_1$-$C_6$-alkyl, $C_1$-$C_6$-haloalkoxy-$C_1$-$C_6$-alkyl, $C_1$-$C_6$-cyanoalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkylthio-$C_1$-$C_6$-alkyl, 3-7-membered heterocyclyl, 3-7-membered haloheterocyclyl, wherein each heterocyclylhas one to three nitrogen atoms and/or one or two oxygen and/or sulfur atoms, $R^3$ is $C_2$-$C_6$-alkyl, $C_3$-$C_6$-cycloalkyl, $C_1$-$C_6$-haloalkyl, $C_1$-$C_6$-hydroxyalkyl, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkyl-$C_3$-$C_6$-cycloalkyl, $C_1$-$C_6$-alkyl-phenyl, $C_1$-$C_6$-haloalkyl-phenyl, wherein the phenyl ring can be substituted by 1-3 halogen, cyano, nitro, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_1$-$C_6$-alkylcarbonyl, hydroxycarbonyl, $C_5$-$C_6$-aryl or $C_5$-$C_6$-heteroaryl having one to three nitrogen atoms and/or one or two oxygen and/or sulfur atoms, wherein $C_5$-$C_6$-aryl or $C_5$-$C_6$-heteroaryl may be substituted by at least one substituent of the list: 1-3 halogen, cyano, nitro, $C_1$-$C_6$-alkyl, $C_3$-$C_6$-cycloalkyl, $C_1$-$C_6$-haloalkyl, $C_1$-$C_6$-hydroxyalkyl, $C_1$-$C_6$-cyanoalkyl, $C_1$-$C_6$-alkoxy-$C_1$-$C_6$-alkyl, $C_1$-$C_6$-haloalkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, $C_2$-$C_6$-alkenyl, $C_2$-$C_6$-haloalkenyl, $C_2$-$C_6$-hydroxyalkenyl, $C_1$-$C_6$-alkoxy-$C_2$-$C_6$-alkenyl, $C_1$-$C_6$-haloalkoxy-$C_2$-$C_6$-alkenyl, amino-$C_2$-$C_6$-alkenyl, ($C_1$-$C_6$-alkyl)amino-$C_2$-$C_6$-alkenyl, di($C_1$-$C_6$-alkyl)amino-$C_2$-$C_6$-alkenyl, $C_2$-$C_6$-alkynyl, $C_2$-$C_6$-haloalkynyl, $C_2$-$C_6$-hydroxyalkynyl, $C_1$-$C_6$-alkoxy-$C_2$-$C_6$-alkynyl, $C_1$-$C_6$-haloalkoxy-$C_2$-$C_6$-alkynyl, amino-$C_2$-$C_6$-alkynyl, ($C_1$-$C_6$-alkyl)amino-$C_2$-$C_6$-alkynyl, di($C_1$-$C_6$-alkyl)amino-$C_2$-$C_6$-alkynyl, $C_1$-$C_6$-alkylcarbonyl, hydroxycarbonyl, $C_1$-$C_6$-alkoxycarbonyl, amino-carbonyl, ($C_1$-$C_6$-alkyl)aminocarbonyl, di($C_1$-$C_6$-alkyl)amino-carbonyl, hydroxy, $C_1$-$C_6$-alkoxy, $C_1$-$C_6$-haloalkoxy, $C_1$-$C_6$-cyanoalkoxy, $C_3$-$C_6$-cycloalkoxy, $C_3$-$C_6$-halocycloalkoxy, $C_3$-$C_6$-alkenyloxy, $C_3$-$C_6$-alkynyloxy, $C_1$-$C_6$-alkylcarbonyloxy, $C_1$-$C_6$-alkyoxycarbonyl-$C_1$-$C_6$-alkyl, hydroxycarbonyl-$C_1$-$C_6$-alkyl, $C_1$-$C_6$-alkoxycarbonyl-$C_1$-$C_6$-alkoxy, hydroxycarbonyl-$C_1$-$C_6$-alkoxy, $C_1$-$C_6$-hydroxyalkoxy, $C_1$-$C_6$-alkoxy-$C_1$-$C_6$-alkoxy, $C_1$-$C_6$-haloalkoxy-$C_1$-$C_6$alkoxy, amino-$C_1$-$C_6$-alkoxy, ($C_1$-$C_6$-alkyl)amino-$C_1$-$C_6$-alkoxy, di($C_1$-$C_6$-alkyl)amino-$C_1$-$C_6$-alkoxy, $C_1$-$C_6$-alkylsulfonyloxy, ($C_1$-$C_6$-alkyl)aminocarbonyloxy, di($C_1$-$C_6$-alkyl)aminocarbonyloxy, $C_1$-$C_6$-alkylthio, $C_1$-$C_6$-haloalkylthio, $C_3$-$C_6$-cycloalkylthio, $C_3$-$C_6$-alkenylthio, $C_3$-$C_6$-alkynylthio, $C_1$-$C_6$-hydroxyalkylthio, $C_1$-$C_6$-alkoxy-$C_1$-$C_6$-alkylthio, $C_1$-$C_6$-haloalkoxy-$C_1$-$C_6$-alkylthio, amino-$C_1$-$C_6$-alkylthio, ($C_1$-$C_6$-alkyl)amino-$C_1$-$C_6$-alkylthio, di($C_1$-$C_6$-alkyl)amino-$C_1$-$C_6$-alkylthio, cyano-$C_1$-$C_6$-alkylthio, amino, $C_1$-$C_6$-alkylamino, di-($C_1$-$C_6$-)alkylamino, $C_3$-$C_6$-cycloalkylamino, $C_3$-$C_6$-alkenylamino, $C_3$-$C_6$-alkynylamino, $C_1$-$C_6$-hydroxyalkylamino, $C_1$-$C_6$-alkoxy-$C_1$-$C_6$-alkylamino, $C_1$-$C_6$-haloalkoxy-$C_1$-$C_6$-alkylamino, amino-$C_1$-$C_6$-alkylamino, ($C_1$-$C_6$-alkyl)amino-$C_1$-$C_6$-alkylamino, di($C_1$-$C_6$-alkyl)amino-$C_1$-$C_6$-alkylamino, $C_1$-$C_6$-alkylsulfonylamino, $C_1$-$C_6$-haloalkylsulfonylamino, $C_1$-$C_6$-alkylsulfonyl($C_1$-$C_6$-alkyl)amino, hydroxycarbonyl-$C_1$-$C_6$-alkylsulfonyl ($C_1$-$C_6$-alkyl)amino, $C_1$-$C_6$-alkoxycarbonyl-$C_1$-$C_6$- alkylsulfonyl($C_1$-$C_6$-alkyl)amino, cyano-$C_1$-$C_6$-alkylsulfonyl($C_1$-$C_6$-alkyl)amino, ($C_1$-$C_6$-alkyl)aminosulfonylamino, di($C_1$-$C_6$-alkyl)aminosulfonylamino, formylamino, formyl($C_1$-$C_6$-alkyl)amino, ($C_1$-$C_6$-alkyl)carbonylamino, ($C_1$-$C_6$-alkoxy)carbonylamino, N($C_1$-$C_6$-alkylcarbonyl)-N($C_1$-$C_6$-alkyl)amino, N($C_1$-$C_6$-alkoxy-$C_1$-$C_6$-alkylcarbonyl)-N($C_1$-$C_6$-alkyl)amino, N($C_1$-$C_6$-alkylcarbonylamino-$C_1$-$C_6$-alkylcarbonyl)-N($C_1$-$C_6$-alkyl)amino, N($C_1$-$C_6$-alkylcarbonylamino-$C_1$-$C_6$-alkyl)-N($C_1$-$C_6$-alkyl)amino, N($C_1$-$C_6$-alkoxy-$C_1$-$C_6$-alkoxy-$C_1$-$C_6$-alkylcarbonyl)-N($C_1$-$C_6$-alkyl)amino, N(cyano-$C_1$-$C_6$-alkyl)-N($C_1$-$C_6$-alkyl)amino, N(cyano-$C_1$-$C_6$-alkylcarbonyl)-N($C_1$-$C_6$-alkyl)amino, N(hydroxycarbonyl-$C_1$-$C_6$-alkylcarbonyl)-N($C_1$-$C_6$-alkyl)amino, N($C_1$-$C_6$-alkoxycarbonyl-$C_1$-$C_6$-alkyl)-N($C_1$-$C_6$-alkyl)amino, N(hydroxycarbonyl-$C_1$-$C_6$-alkylcarbonyl)-amino-$C_1$-$C_6$-alkyl, N(hydroxycarbonyl-$C_1$-$C_6$-alkyl)-N($C_1$-$C_6$-alkyl)amino, ($C_1$-$C_6$-alkyl)aminocarbonylamino, di($C_1$-$C_6$-alkyl)aminocarbonylamino, ($C_1$-$C_6$-alkyl)aminocarbonyl($C_1$-$C_6$-alkyl)amino, $C_1$-$C_6$-alkylsulfinyl, Cl-$C_6$-alkylsulfonyl, $C_3$-$C_6$-cyclo-alkylsulfonyl, $C_3$-$C_6$-alkenylsulfonyl, $C_3$-$C_6$-alkynylsulfonyl, $C_1$-$C_6$-hydroxyalkylsulfonyl, $C_1$-$C_6$-alkoxy-$C_1$-$C_6$-alkylsulfonyl, $C_1$-$C_6$-haloalkoxy-$C_1$-$C_6$-alkylsulfonyl, amino-$C_1$-$C_6$-alkylsulfonyl, ($C_1$-$C_6$-alkyl)amino-$C_1$-$C_6$-alkylsulfonyl, di($C_1$-$C_6$-alkyl)amino-$C_1$-$C_6$-alkyl-sulfonyl, aminosulfonyl, ($C_1$-$C_6$-alkyl)aminosulfonyl, di($C_1$-$C_6$-alkyl)aminosulfonyl, phenyl, phenylcarbonyl, phenyloxy, phenyl-$C_1$-$C_6$-alkoxy, phenyl-$C_1$-$C_6$-alkoxycarbonyl, phenyl-$C_1$-$C_6$-alkoxycarbonyl-$C_1$-$C_6$-alkyl, phenyl-$C_1$-$C_6$-alkoxycarbonyl-$C_1$-$C_6$-alkoxy, phenylcarbonyloxy, phenylthio, phenylsulfinyl, phenylsulfonyl, phenylsulfonyloxy, phenyl-$C_1$-$C_6$-alkylsulfonyloxy, phenyl-$C_1$-$C_6$-alkoxysulfonyloxy, phenylsulfonylamino, phenylamino, N(phenyl)-N($C_1$-$C_6$-alkyl)amino, N(phenyl-$C_1$-$C_6$-alkyl)-N($C_1$-$C_6$-alkyl)amino, phenylcarbonylamino, N-phenylcarbonyl-N($C_1$-$C_6$-alkyl)amino, wherein each of the phenyl groups may be partially or fully halogenated and/or may carry one to three substituents selected from the group consisting of cyano, nitro, $C_1$-$C_6$-alkyl, $C_1$-$C_6$-haloalkyl, hydroxy, $C_1$-$C_6$-alkoxy, $C_1$-$C_6$-alkyl-carbonyloxy, $C_1$-$C_6$-haloalkoxy, $C_3$-$C_6$-alkenyloxy, $C_3$-$C_6$-alkynyloxy, $C_1$-$C_6$-alkylthio, $C_1$-$C_6$-alkylsulfonyl, $C_1$-$C_6$-alkylsulfonylamino, $C_1$-$C_6$-haloalkylsulfonylamino, $C_1$-$C_6$-alkoxycarbonyl, hydroxycarbonyl, hydroxycarbonyl-$C_1$-$C_6$-alkyl, hydroxycarbonyl-$C_1$-$C_6$-alkoxy, 3-7-membered heterocyclyl having one to four nitrogen atoms, one or two nitrogen atoms and one sulfur atom, one nitrogen atom and one oxygen atom, one or two sulfur atoms, or one or two oxygen atoms;

heterocyclyl, heterocyclyl-$C_1$-$C_6$-alkyl, heterocyclyl-$C_2$-$C_6$-alkenyl, heterocy-clyl-$C_2$-$C_6$-alkynyl, heterocyclyl-$C_1$-$C_6$-alkoxy, heterocyclyl-$C_1$-$C_6$-alkylthio, heterocyclyl-$C_1$-$C_6$-alkylamino, heterocyclyl-$C_1$-$C_6$-alkylsulfonyl, heterocyclyloxy, heterocyclylthio, heterocyclylsulfinyl, heterocyclylsulfonyl, heterocyclylsulfonyloxy, heterocyclylamino, heterocyclylcarbonyloxy, heterocyclylamino, heterocyclyl-[($C_1$-$C_6$-alkyl)amino], heterocyclylcarbonylamino, heterocyclylcarbonyl[($C_1$-$C_6$-alkyl)amino], N(heterocyclyl-$C_1$-$C_6$-alkyl)-N($C_1$-$C_6$-alkyl)amino, N(heterocyclyl-$C_1$-$C_6$-alkylcarbonyl)-N($C_1$-$C_6$-alkyl)amino, wherein each of the heterocyclyl groups being 3-7-membered saturated, partially unsaturated or unsaturated and having one to four nitrogen atoms, one or two nitrogen atoms and one sulfur atom, one nitrogen atom and one oxygen atom, one or two sulfur atoms, or one or two oxygen atoms, and wherein each of the heterocyclyl groups may be partially or fully halogenated and/or may be substituted with one to three substituents selected from the group consisting of cyano, $C_1$-$C_6$-alkyl, $C_1$-$C_6$-haloalkyl, hydroxy, mercapto, oxy, $C_1$-$C_6$-alkoxy, $C_1$-$C_6$-alkylcarbonyloxy, $C_1$-$C_6$-haloalkoxy, $C_3$-$C_6$-alkenyloxy, $C_3$-$C_6$-alkynyloxy, $C_1$-$C_6$-alkylthio, $C_1$-$C_6$-alkylsulfonyl, $C_1$-$C_6$-alkoxycarbonyl, hydroxycarbonyl, hydroxycarbonyl-$C_1$-$C_6$-alkyl, hydroxycarbonyl-$C_1$-$C_6$-alkoxy, 3-7-membered heterocyclyl having one to four nitrogen atoms, one or two nitrogen atoms and one sulfur atom, one nitrogen atom and one oxygen atom, one or two sulfur atoms, or one or two oxygen atoms;

the $C_5$-$C_6$-aryl or $C_5$-$C_6$-heteroaryl can also be anellated with another 3-7-membered saturated, partially unsaturated or unsaturated cycloalkyl or heterocyclyl, which cycloalkyl and heterocyclyl can be substituted by 1-3 halogen, cyano, nitro, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_1$-$C_6$-alkylcarbonyl, hydroxycarbonyl.

Surprisingly it has now been found that said pyrazolopyran effectively controls undesired vegetation.

Moreover it has been found that a pyrazolopyran of formula I can be used as inhibitor of the enzyme serinehydroxymethyltransferase (SHMT). Said enzyme plays a key role in the photorespiration cycle of plant, controlling the formyl-transfer between glycine and serine.

Thus, a further subject of the present invention is a pyrazolopyran of the formula I for use as an inhibitor of the enzyme serinehydroxymethyltransferase (SHMT).

Additionally it has now been found that a pyrazolopyran of the formula I is also useful for treating or preventing infections. Preferably it can be used for treating or preventing parasitic and/or bacterial infections.

Accordingly, a pyrazolopyran of the formula I for use as a medicament falls within this invention.

The present invention also provides an herbicidal composition comprising an herbicidal active amount of a pyrazolopyran of formula I and auxiliaries customary for formulating crop protection agents.

Additionally, the present invention provides a pharmaceutical composition comprising a pharmaceutically effective amount of a pyrazolopyran of formula I and auxiliaries customary for formulating pharmaceuticals.

Further, a process for the preparation of a pyrazolopyran of formula I was found. In this process a vinyl-1,1-dinitrile of formula II

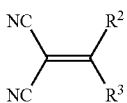

wherein R² and R³ are as defined above,
is cyclized with an hydroxypyrazole of formula III,

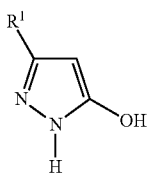

wherein R¹ is as defined above,
to give the pyrazolopyran of formula I,

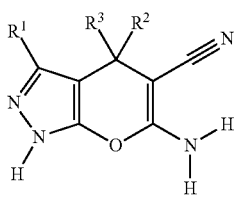

wherein R¹, R² and R³ are as defined above.

Herewith is further disclosed a process for the preparation of an herbicidal composition, which comprises mixing an herbicidal active amount of a pyrazolopyran of formula I and auxiliaries customary for formulating crop protection agents.

A process for the preparation of a pharmaceutical composition, which comprises mixing a pharmaceutically effective amount of a pyrazolopyran as defined in claim 1, 3 or 4 and auxiliaries customary for formulating pharmaceuticals is also the subject of the present invention.

In addition, the present invention provides a method of controlling undesired vegetation, which comprises allowing an herbicidal active amount of a pyrazolopyran of formula I or an herbicidal composition as defined above to act on plants, their environment or on seed.

Moreover, the subject of the present invention is the use of a pyrazolopyran of formula I or of an herbicidal composition as defined above for controlling undesired vegetation.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

As used herein, the term "pyrazolopyran of formula I" includes any pyrazolopyran of formula I, any tautomer thereof, any salt thereof, preferably an agriculturaly suitable and/or pharmaceutically acceptable salt, any cleavable prodrug thereof, or any mixture thereof.

If a pyrazolopyran of formula I as described herein has one or more centers of chirality and, as a consequence, is present as enantiomers or diastereomers, it is possible to use both, the pure enantiomers or diastereomers as well as any mixture thereof, in particular in the compositions according to the invention.

If a pyrazolopyran of formula I as described herein is capable of forming geometrical isomers, for example E/Z isomers, it is possible to use both, a pure isomer and any mixture thereof, in particular in the compositions according to the invention.

Thus, as used herein, the term "pyrazolopyran of formula I" also includes any possible enantiomer, diastereomer or geometrical isomer and mixtures thereof.

As used herein, the term "tautomer" includes both tautomeric forms (Ia) and (Ib) of a pyrazolopyran of formula I as well as a mixture thereof.

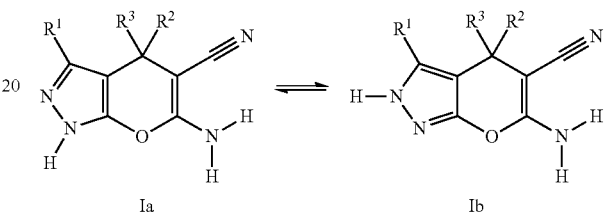

It is possible to use both, a pure tautomer and any mixture thereof, in particular in the compositions according to the invention.

As used herein, the term "salt" includes any salt or any mixture of the respective salts. All salts whether agriculturally suitable or pharmaceutically acceptable or not are included within the ambit of the present invention.

The term "agriculturally suitable salt" refers to the salts of those cations and the acid addition salts of those acids whose cations and anions, respectively, have no adverse effect on the desired activity of the active compounds.

Preferred cations are the ions of the alkali metals, preferably of lithium, sodium or potassium, of the alkaline earth metals, preferably of calcium or magnesium, and of the transition metals, preferably of manganese, copper, zinc or iron, further ammonium or substituted ammonium in which one to four hydrogen atoms are replaced by $C_1$-$C_4$-alkyl, hydroxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyeth-1-oxy)eth-1-ylammonium, di(2-hydroxyeth-1-yl)ammonium, benzyltrimethylammonium, benzyltriethylammonium, furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate or butyrate.

The term "pharmaceutically acceptable", as used herein, refers to entities that are physiologically tolerable and do not typically produce untoward reactions when administered to a subject, preferably to a mammal (e.g. a human). Preferably, the term "pharmaceutically acceptable" means approved by a regulatory agency or listed in e.g. the U.S. Pharmacopeia for use in mammals and particularly in humans.

The term "pharmaceutically acceptable salt" refers to those salts which possess the biological effectiveness and properties of the parent compound and which are not biologically or otherwise undesirable. The nature of the salt is not critical, provided that it is non-toxic and has no adverse effect on the desired pharmacological activity of the active compounds.

For therapeutic use, salts of the pyrazolopyran of formula I are those wherein the counter-ion is pharmaceutically acceptable. However, salts of acids and bases, which are non-pharmaceutically acceptable, may also find use, for example, in the preparation and purification of pharmaceutically acceptable compounds.

The pharmaceutically acceptable salts as mentioned above comprise the therapeutically active non-toxic salt forms, which the compounds of formula I are able to form. The latter can conveniently be obtained by treating the base form with such appropriate acids as inorganic acids, e.g. hydrohalic acids such as hydrochloric, hydrobromic or the like; sulfuric acid; nitric acid; phosphoric acid or the like; or organic acids such as acetic, propanoic, hydroxyacetic, 2-hydroxypropanoic, oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfonic, 2-hydroxybenzoic, 4-amino-2-hydroxybenzoic or the like acids. Conversely, the salt form can be converted by treatment with alkali into the free base form.

The term "therapeutically effective" applied to dose or amount refers to that quantity of a compound or pharmaceutical composition that is sufficient to result in a desired activity upon administration to a subject in need thereof.

The term "subject", as used in connection with therapeutic use refers to a living animal body, e.g. mammals and birds, preferably mammals, most preferably humans; also preferably birds, also most preferably poultry.

As used herein, the term "auxilaries" includes one or more respective auxilaries.

As used herein, the terms "undesirable vegetation" and "harmful plants" are synonyms.

The organic moieties mentioned in the definition of the variables $R_1$, $R_2$, $R_3$, $R_4$, $R^5$ and $R^6$, are—like the term "halogen"—collective terms for individual enumerations of the individual group members. The term halogen denotes in each case fluorine, chlorine, bromine or iodine. All hydrocarbon chains, i.e. all alkyl, can be straight-chain or branched, the prefix $C_n$-$C_m$ denoting in each case the possible number of carbon atoms in the group.

Examples of such meanings are:

$C_1$-$C_4$-alkyl: for example $CH_3$, $C_2H_5$, n-propyl, $CH(CH_3)_2$, n-butyl, $CH(CH_3)$—$C_2H_5$, $CH_2$—$CH(CH_3)_2$ and $C(CH_3)_3$;

$C_1$-$C_6$-alkyl and also the $C_1$-$C_6$-alkyl moieties of $C_1$-$C_6$-hydroxyalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkylthio, $C_1$-$C_6$-alkylamino, $C_1$-$C_6$-cyanoalkyl, $C_1$-$C_6$-alkylthio-$C_1$-$C_6$-alkyl, $C_1$-$C_6$-alkyl-$C_3$-$C_6$-cycloalkyl, $C_1$-$C_6$-alkylphenyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, ($C_1$-$C_6$-alkyl)amino-$C_2$-$C_6$-alkenyl, di($C_1$-$C_6$-alkyl)amino-$C_2$-$C_6$-alkenyl, ($C_1$-$C_6$-alkyl)amino-$C_2$-$C_6$-alkynyl, di($C_1$-$C_6$-alkyl)amino-$C_2$-$C_6$-alkynyl, $C_1$-$C_6$-alkylcarbonyl, ($C_1$-$C_6$-alkyl)aminocarbonyl, di($C_1$-$C_6$-alkyl)aminocarbonyl, $C_1$-$C_6$-alkylcarbonyloxy, ($C_1$-$C_6$-alkyl)amino-$C_1$-$C_6$-alkoxy, di($C_1$-$C_6$-alkyl)amino-$C_1$-$C_6$-alkoxy, $C_1$-$C_6$-alkyoxycarbonyl-$C_1$-$C_6$-alkyl, hydroxycarbonyl-$C_1$-$C_6$-alkyl, $C_1$-$C_6$-alkylsulfonyloxy, ($C_1$-$C_6$-alkyl)aminocarbonyloxy, di($C_1$-$C_6$-alkyl)aminocarbonyloxy, $C_1$-$C_6$-alkylthio, $C_1$-$C_6$-hydroxyalkylthio, $C_1$-$C_6$-alkoxy-$C_1$-$C_6$-alylthio, $C_1$-$C_6$-haloalkoxy-$C_1$-$C_6$-alkylthio, amino-$C_1$-$C_6$-alkylthio, ($C_1$-$C_6$-alkyl)amino-$C_1$-$C_6$-alkylthio, di($C_1$-$C_6$-alkyl)amino-$C_1$-$C_6$-alkylthio, cyano-$C_1$-$C_6$-alkylthio, $C_1$-$C_6$-alkylamino, di($C_1$-$C_6$-alkyl)amino, $C_1$-$C_6$-hydroxyalkylamino, $C_1$-$C_6$-alkoxy-$C_1$-$C_6$-alkylamino, $C_1$-$C_6$-haloalkoxy-$C_1$-$C_6$-alkylamino, amino-$C_1$-$C_6$-alkylamino, ($C_1$-$C_6$-alkyl)amino-$C_1$-$C_6$-alkylamino, di($C_1$-$C_6$-alkyl)amino-$C_1$-$C_6$-alkylamino, $C_1$-$C_6$-alkylsulfonylamino, $C_1$-$C_6$-alkylsulfonyl($C_1$-$C_6$-alkyl)amino, hydroxycarbonyl-$C_1$-$C_6$-alkylsulfonyl($C_1$-$C_6$-alkyl)amino, $C_1$-$C_6$-alkoxycarbonyl-$C_1$-$C_6$-alkylsulfonyl($C_1$-$C_6$-alkyl)amino, cyano-$C_1$-$C_6$-alkylsulfonyl($C_1$-$C_6$-alkyl)amino, ($C_1$-$C_6$-alkyl)aminosulfonylamino, di($C_1$-$C_6$-alkyl)aminosulfonylamino, formyl($C_1$-$C_6$-alkyl)amino, ($C_1$-$C_6$-alkyl)carbonylamino, N($C_1$-$C_6$-alkylcarbonyl)-N($C_1$-$C_6$-alkyl)amino, N($C_1$-$C_6$-alkoxy-$C_1$-$C_6$-alkylcarbonyl)-N($C_1$-$C_6$-alkyl)amino, N($C_1$-$C_6$-alkylcarbonylamino-$C_1$-$C_6$-alkylcarbonyl)-N($C_1$-$C_6$-alkyl)amino, N($C_1$-$C_6$-alkylcarbonylamino-$C_1$-$C_6$-alkyl)-N($C_1$-$C_6$-alkyl)amino, N($C_1$-$C_6$-alkoxy-$C_1$-$C_6$-alkoxy-$C_1$-$C_6$-alkylcarbonyl)-N($C_1$-$C_6$-alkyl)amino, N(cyano-$C_1$-$C_6$-alkyl)-N($C_1$-$C_6$-alkyl)amino, N(cyano-$C_1$-$C_6$-alkylcarbonyl)-N($C_1$-$C_6$-alkyl)amino, N(hydroxycarbonyl-$C_1$-$C_6$-alkylcarbonyl)-N($C_1$-$C_6$-alkyl)amino, N($C_1$-$C_6$-alkoxycarbonyl-$C_1$-$C_6$-alkyl)-N($C_1$-$C_6$-alkyl)amino, N(hydroxycarbonyl-$C_1$-$C_6$-alkylcarbonyl)-amino-$C_1$-$C_6$-alkyl, N(hydroxycarbonyl-$C_1$-$C_6$-alkyl)-N($C_1$-$C_6$-alkyl)amino, ($C_1$-$C_6$-alkyl)aminocarbonylamino, di($C_1$-$C_6$-alkyl)aminocarbonylamino, ($C_1$-$C_6$-alkyl)aminocarbonyl($C_1$-$C_6$-alkyl)amino, $C_1$-$C_6$-alkylsulfinyl, $C_1$-$C_6$-alkylsulfonyl, $C_1$-$C_6$-hydroxyalkylsulfonyl, $C_1$-$C_6$-alkoxy-$C_1$-$C_6$-alkylsulfonyl, $C_1$-$C_6$-haloalkoxy-$C_1$-$C_6$-alkylsulfonyl, amino-$C_1$-$C_6$-alkylsulfonyl, ($C_1$-$C_6$-alkyl)amino-$C_1$-$C_6$-alkylsulfonyl, di($C_1$-$C_6$-alkyl)amino-$C_1$-$C_6$-alkylsulfonyl, ($C_1$-$C_6$-alkyl)aminosulfonyl, di($C_1$-$C_6$-alkyl)aminosulfonyl, phenyl-$C_1$-$C_6$-alkoxycarbonyl-$C_1$-$C_6$-alkyl, N(phenyl)-N($C_1$-$C_6$-alkyl)amino, N(phenyl-$C_1$-$C_6$-alkyl)-N($C_1$-$C_6$-alkyl)amino, N-phenylcarbonyl-N($C_1$-$C_6$-alkyl)amino, phenyl-Cl-$C_6$-alkylsulfonyloxy, heterocyclyl-$C_1$-$C_6$-alkyl, heter-ocyclyl-$C_1$-$C_6$-alkylthio, heterocyclyl-$C_1$-$C_6$-alkylamino, heterocyclyl-$C_1$-$C_6$-alkylsulfonyl, heterocyclyl-[($C_1$-$C_6$-alkyl)amino], heterocyclylcarbonyl [($C_1$-$C_6$-alkyl)amino], N(heterocyclyl-$C_1$-$C_6$-alkyl)-N($C_1$-$C_6$-alkyl)amino, N(heterocyclyl-$C_1$-$C_6$-alkylcarbonyl)-N($C_1$-$C_6$-alkyl)amino: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: a $C_1$-$C_4$-alkyl as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyla $C_1$-$C_3$-haloalkyl radical as mentioned above, and also, for example, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl and also the $C_1$-$C_6$-haloalkyl moieties of $C_1$-$C_6$-hydroxyhaloalkyl, $C_1$-$C_6$-haloalkylthio, $C_1$-$C_6$-haloalkylsulfonylamino and $C_1$-$C_6$-haloalkyl-phenyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-cycloalkyl and also the cycloalkyl moieties of $C_1$-$C_6$-hydroxycycloalkyl, $C_3$-$C_6$-cycloalkylthio, $C_3$-$C_6$-cycloalkylamino and $C_3$-$C_6$-cycloalkylsulfonyl, $C_1$-$C_6$-alkyl-$C_3$-$C_6$-cycloalkyl: monocyclic saturated hydrocarbons having 3 to 6 ring members, such as cyclopropyl, cyclobutyl, cyclopentyl and cyclohexyl;

$C_3$-$C_7$-cycloalkyl: a $C_3$-$C_6$-cycloalkyl as mentioned above and also cycloheptyl;

$C_3$-$C_6$-halocycloalkyl: a $C_3$-$C_6$-cycloalkyl as mentioned above which is partially or fully substituted by fluorine, chlorine, bromine and/or iodine: for example 1-fluorocyclopropyl, 1-clorocyclopropyl, 1-bromocyclopropyl, 1-iodocyclopropyl, 2-fluorocyclopropyl, 2-clorocyclopropyl, 2-bromocyclopropyl, 2-iodocyclopropyl, 2,2-difluorocyclopropyl, 2,2-diclorocyclopropyl, 2,2-dibromocyclopropyl, 2,2-diiodocyclopropyl, 1-fluorocyclobutyl, 1-clorocyclobutyl, 1-bromocyclobutyl, 1-iodocyclobutyl, 2-fluorocyclobutyl, 2-clorocyclobutyl, 2-bromocyclobutyl, 2-iodocyclobutyl, 1,2-difluorocyclobutyl, 1,2-diclorocyclobutyl, 1,2-dibromocyclobutyl, 1,2-diiodocyclobutyl, 2,2-difluorocyclobutyl, 2,2-diclorocyclobutyl, 2,2-dibromocyclobutyl, 2,2-d iiodocyclobutyl, 1,3-difluorocyclobutyl, 1,3-diclorocyclobutyl, 1,3-dibromocyclobutyl, 1,3-diiodocyclobutyl, 1-fluorocyclopentyl, 1-clorocyclopentyl, 1-bromocyclopentyl, 1-iodocyclopentyl, 2-fluorocyclopentyl, 2-clorocyclopentyl, 2-bromocyclopentyl, 2-iodocyclopentyl, 3-fluorocyclopentyl, 3-clorocyclopentyl, 3-bromocyclopentyl, 3-iodocyclopentyl, 1-fluorocyclohexyl, 1-clorocyclohexyl, 1-bromocyclohexyl, 1-iodocyclohexyl, 2-fluorocyclohexyl, 2-clorocyclohexyl, 2-bromocyclohexyl, 2-iodocyclohexyl, 3-fluorocyclohexyl, 3-clorocyclohexyl, 3-bromocyclohexyl, 3-iodocyclohexyl, 4-fluorocyclohexyl, 4-clorocyclohexyl, 4-bromocyclohexyl, 4-iodocyclohexyl;

$C_3$-$C_6$-alkenyl and also the $C_3$-$C_6$-alkenyl moieties of $C_3$-$C_6$-alkenyloxy, $C_3$-$C_6$-alkenylthio, $C_3$-$C_6$-alkenylamino, $C_3$-$C_6$-alkenylsulfonyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkenyl and also the $C_2$-$C_6$-alkenyl moieties of $C_2$-$C_6$-hydroxyalkenyl, $C_1$-$C_6$-alkoxy-$C_2$-$C_6$-alkenyl, $C_1$-$C_6$-haloalkoxy-$C_2$-$C_6$-alkenyl, amino-$C_2$-$C_6$-alkenyl, ($C_1$-$C_6$-alkyl)amino-$C_2$-$C_6$-alkenyl, di($C_1$-$C_6$-alkyl)amino-$C_2$-$C_6$-alkenyl, heterocyclyl-$C_2$-$C_6$-alkenyl: $C_3$-$C_6$-alkenyl as mentioned above, and also ethenyl;

$C_2$-$C_6$-haloalkenyl: a $C_2$-$C_6$-alkenyl as mentioned above which is partially or fully substituted by fluorine, chlorine, bromine and/or iodine, for example 2-chlorovinyl, 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromovinyl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-cycloalkenyl: monocyclic unsaturated hydrocarbons having 3 to 6 ring members for example cyclopropenyl, cyclobutenyl, cyclopentenyl and cyclohexenyl, $C_3$-$C_6$-halocycloalkenyl: $C_3$-$C_6$-cycloalkenyl as mentioned above which is partially or fully substituted by fluorine, chlorine, bromine and/or iodine.

$C_3$-$C_6$-alkynyl and also the $C_3$-$C_6$-alkynyl moieties of $C_3$-$C_6$-alkynyloxy, $C_3$-$C_6$-alkynylthio, $C_3$-$C_6$-alkynyamino, $C_3$-$C_6$-alkynylsulfonyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_2$-$C_6$-alkynyl and also the $C_2$-$C_6$-alkynyl moieties of $C_2$-$C_6$-hydroxyalkynyl, $C_1$-$C_6$-alkoxy-$C_2$-$C_6$-alkynyl, $C_1$-$C_6$-haloalkoxy-$C_2$-$C_6$-alkynyl, amino-$C_2$-$C_6$-alkynyl, ($C_1$-$C_6$-alkyl)amino-$C_2$-$C_6$-alkynyl, di($C_1$-$C_6$-alkyl)amino-$C_2$-$C_6$-alkynyl, heterocyclyl-$C_2$-$C_6$-alkynyl: $C_3$-$C_6$-alkynyl as mentioned above, and also ethynyl;

$C_2$-$C_6$-haloalkynyl: a $C_2$-$C_6$-alkynyl as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of $C_1$-$C_6$-alkoxycarbonyl, $C_1$-$C_6$-alkyoxycarbonyl-$C_1$-$C_6$-alkyl, phenyl-$C_1$-$C_6$-alkoxycarbonyl-$C_1$-$C_6$-alkyl, $C_1$-$C_6$-hydroxyalkoxy, $C_1$-$C_6$-cyanoalkoxy, $C_1$-$C_6$-alkoxycarbonyl-$C_1$-$C_6$-alkoxy, phenyl-$C_1$-$C_6$-alkoxycarbonyl-$C_1$-$C_6$-alkoxy, hydroxycarbonyl-$C_1$-$C_6$-alkoxy, $C_1$-$C_6$-alkoxycarbonyl, $C_1$-$C_6$-alkoxy-$C_1$-$C_6$-alkoxy, amino-$C_1$-$C_6$-alkoxy, $C_1$-$C_6$-alkoxy-$C_1$-$C_6$-alkyl, $C_1$-$C_6$-alkoxy-$C_2$-$C_6$-alkenyl, $C_1$-$C_6$-alkoxy-$C_2$-$C_6$-alkynyl, $C_1$-$C_6$-haloalkoxy-$C_1$-$C_6$-alkoxy, ($C_1$-$C_6$-alkyl)amino-$C_1$-$C_6$-alkoxy, di($C_1$-$C_6$-alkyl)amino-$C_1$-$C_6$-alkoxy, $C_1$-$C_6$-alkoxy-$C_1$-$C_6$-alkylthio, $C_1$-$C_6$-alkoxy-$C_1$-$C_6$-alkylamino, $C_1$-$C_6$-alkoxycarbonyl-$C_1$-$C_6$-alkylsulfonyl($C_1$-$C_6$-alkyl)amino, ($C_1$-$C_6$-alkoxy)carbonylamino, N($C_1$-$C_6$-alkoxy-$C_1$-$C_6$-alkylcarbonyl)-N($C_1$-$C_6$-alkyl)amino, N($C_1$-$C_6$-alkoxy-$C_1$-$C_6$-alkoxy-$C_1$-$C_6$-alkylcarbonyl)-N($C_1$-$C_6$-alkyl)amino, N($C_1$-$C_6$-alkoxycarbonyl-$C_1$-$C_6$-alkyl)-N($C_1$-$C_6$-alkyl)amino, $C_1$-$C_6$-alkoxy-$C_1$-$C_6$-alkylsulfonyl, phenyl-$C_1$-$C_6$-alkoxy, phenyl-$C_1$-$C_6$-alkoxycarbonyl, heterocyclyl-$C_1$-$C_6$-alkoxy: $C_1$-$C_4$-alkoxy as mentioned above, and also, for example, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$-$C_4$-haloalkoxy: a $C_1$-$C_4$-alkoxy as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoro-propoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$-$C_6$-haloalkoxy and the $C_1$-$C_6$-haloalkoxy moieties of $C_1$-$C_6$-haloalkoxy-$C_1$-$C_6$-alkyl, $C_1$-$C_6$-haloalkoxy-$C_2$-$C_6$-alkenyl, $C_1$-$C_6$-haloalkoxy-$C_2$-$C_6$-alkynyl, $C_1$-$C_6$-haloalkoxy-$C_1$-$C_6$-alkoxy, $C_1$-$C_6$-haloalkoxy-$C_1$-$C_6$-alkylthio, $C_1$-$C_6$-haloalkoxy-$C_1$-$C_6$-alkylamino, $C_1$-$C_6$-haloalkoxy-$C_1$-$C_6$-alkylsulfonyl: $C_1$-$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_3$-$C_6$-cycloalkoxy: ethers of monocyclic saturated hydrocarbons having 3 to 6 ring members, such as cyclopropoxy, cyclobutoxy, cyclopentoxy and cyclohexoxy;

$C_3$-$C_6$-halocycloalkoxy: a $C_3$-$C_6$-cycloalkoxy as mentioned above which is partially or fully substituted by fluorine, chlorine, bromine and/or iodine.

heterocyclyl and the heterocyclyl moieties of heterocyclyl-$C_1$-$C_6$-alkyl, heterocyclyl-$C_2$-$C_6$-alkenyl, heterocyclyl-$C_2$-$C_6$-alkynyl, heterocyclyl-$C_1$-$C_6$-alkoxy, heterocyclyl-$C_1$-$C_6$-alkylthio, heterocyclyl-$C_1$-$C_6$-alkylamino, heterocyclyl-$C_1$-$C_6$-alkylsulfonyl, heterocyclyloxy, heterocyclylthio, heterocyclylsulfinyl, heterocyclylsulfonyl, heterocyclylsulfonyloxy, heterocyclylcarbonyl, heterocyclylcarbonyloxy, heterocyclylamino, heterocyclyl-[($C_1$-$C_6$-alkyl)amino], heterocyclylcarbonylamino, heterocyclylcarbonyl[($C_1$-$C_6$-alkyl)amino]: saturated, partially unsaturated or unsaturated 3- to 7-membered, preferably 4- to 7-membered, especially preferably 4- to 6-membered, most preferably 5- to 6-membered heterocycle having one to four nitrogen atoms, one or two nitrogen atoms and one sulfur atom, one nitrogen atom and one oxygen atom, one or two sulfur atoms, or one or two oxygen atoms, for example 3- and 4-membered rings like 2-oxiranyl, 2-oxetanyl, 3-oxetanyl, 2-aziridinyl, 2-thiiranyl, 2-thietanyl, 3-thietanyl, 1-azetidinyl, 2-azetidinyl, 1-azetinyl, 2-azetinyl;

5-membered saturated rings like 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 2-isothiazolidinyl, 3-isothiazolidinyl, 4-isothiazolidinyl, 5-isothiazolidinyl, 1-pyrazolidinyl, 3-pyrazolidinyl, 4-pyrazolidinyl, 5-pyrazolidinyl, 2-oxazolidinyl, 3-oxazolidinyl, 4-oxazolidinyl, 5-oxazolidinyl, 2-thiazolidinyl, 3-thiazolidinyl, 4-thiazolidinyl, 5-thiazolidinyl, 1-imidazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,2,4-oxadiazolidin-2-yl, 1,2,4-oxadiazolidin-4-yl, 1,3,4-oxadiazolidin-2-yl, 1,2,4-thiadiazolidin-2-yl, 1,2,4-thiadiazolidin-4-yl, 1,3,4-thiadiazolidin-2-yl, 1,2,4-triazolidin-1-yl, 1,3,4-triazolidin-2-yl;

5-membered partially unsaturated rings like 2,3-dihydrofur-2-yl, 2,3-dihydrofur-3-yl, 2,4-dihydrofur-2- yl, 2,4-dihydrofur-3-yl, dioxolan-2-yl, 1,3-dioxol-2-yl, 2,3-dihydrothien-2-yl, 2,3-dihydrothien-3-yl, 2,4-dihydrothien-2-yl, 2,4-dihydrothien-3-yl, 4,5-dihydropyrrol-1-yl, 4,5-dihydropyrrol-2-yl, 4,5-dihydropyrrol-3-yl, 2,5-dihydropyrrol-1-yl, 2,5-dihydropyrrol-2-yl, 2,5-dihydropyrrol-3-yl, 2,3-dihydroisoxazol-1-yl, 2,3-dihydroisoxazol-3-yl, 2,3-dihydroisoxazol-4-yl, 2,3-dihydroisoxazol-5-yl, 2,5-dihydroisoxazol-3-yl, 2,5-dihydroisoxazol-4-yl, 2,5-dihydroisoxazol-5-yl, 4,5-dihydroisoxazol-2-yl, 4,5-dihydroisoxazol-3-yl, 4,5-dihydroisoxazol-4-yl, 4,5-dihydroisoxazol-5-yl, 2,3-dihydroisothiazol-1-yl, 2,3-dihydroisothiazol-3-yl, 2,3-dihydroisothiazol-4-yl, 2,3-dihydroisothiazol-5-yl, 2,5-dihydroisothiazol-3-yl, 2,5-dihydroisothiazol-4-yl, 2,5-dihydroisothiazol-5-yl, 4,5-dihydroisothiazol-1-yl, 4,5-dihydroisothiazol-3-yl, 4,5-dihydroisothiazol-4-yl, 4,5-dihydroisothiazol-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydroimidazol-1-yl, 2,3-dihydroimidazol-2-yl, 2,3-dihydroimidazol-3-yl, 2,3-dihydroimidazol-4-yl, 2,3-dihydroimidazol-5-yl, 4,5-dihydroimidazol-1-yl, 4,5-dihydroimidazol-2-yl, 4,5-dihydroimidazol-4-yl, 4,5-dihydroimidazol-5-yl, 2,5-dihydroimidazol-1-yl, 2,5-dihydroimidazol-2-yl, 2,5-dihydroimidazol-4-yl, 2,5-dihydroimidazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 2,3-dihydrothiazol-2-yl, 2,3-dihydrothiazol-3-yl, 2,3-dihydrothiazol-4-yl, 2,3-dihydrothiazol-5-yl, 3,4-dihydrothiazol-2-yl, 3,4-dihydrothiazol-3-yl, 3,4-dihydrothiazol-4-yl, 3,4-dihydrothiazol-5-yl, 3,4-dihydrothiazol-2-yl, 3,4-dihydrothiazol-3-yl, 3,4-dihydrothiazol-4-yl;

5-membered unsaturated rings like furyl (for example 2-furyl, 3-furyl), thienyl (for example 2-thienyl, 3-thienyl), pyrrolyl (for example pyrrol-2-yl, pyrrol-3-yl), pyrazolyl (for example pyrazol-3-yl, pyrazol-4-yl), isoxazolyl (for example isoxazol-3-yl, isoxazol-4-yl, isoxazol-5-yl), isothiazolyl (for example isothiazol-3-yl, isothiazol-4-yl, isothiazol-5-yl), imidazolyl (for example imidazol-2-yl, imidazol-4-yl), oxazolyl (for example oxazol-2-yl, oxazol-4-yl, oxazol-5-yl), thiazolyl (for example thiazol-2-yl, thiazol-4-yl, thiazol-5-yl), oxadiazolyl (for example 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl), thiadiazolyl (for example 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl), triazolyl (for example 1,2,3-triazol-4-yl, 1,2,4-triazol-3-yl);

6-membered saturated rings like 1-piperidinyl, 2-piperidinyl, 3-piperidinyl, 4-piperidinyl, 1,3-dioxan-5-yl, 1,4-dioxanyl, 1,3-dithian-5-yl, 1,3-dithianyl, 1,3-oxathian-5-yl, 1,4-oxathianyl, 2-tetrahydropyranyl, 3-tetrahydropyranyl, 4-tetrahydropyranyl, 2-tetrahydrothiopyranyl, 3-tetrahydrothiopyranyl,4-tetrahydrothiopyranyl, 1-hexahydropyridazinyl, 3-hexahydropyridazinyl, 4-hexahydropyridazinyl, 1-hexahydropyrimidinyl, 2-hexahydropyrimidinyl, 4-hexahydropyrimidinyl, 5-hexahydropyrimidinyl, 1-piperazinyl, 2-piperazinyl, 1,3,5-hexahydrotriazin-1-yl, 1,3,5-hexahydrotriazin-2-yl, 1,2,4-hexahydrotriazin-1-yl, 1,2,4-hexahydrotriazin-3-yl, tetrahydro-1,3-oxazin-1-yl, tetrahydro-1,3-oxazin-2-yl, tetrahydro-1,3-oxazin-6-yl, 1-morpholinyl, 2-morpholinyl, 3-morpholinyl;

6-membered partially unsaturated rings like 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 5,6-dihydro-4H-1,3-oxazin-2-yl;

6-membered unsaturated rings like pyridyl (for example pyridin-2-yl, pyridin-3-yl, pyridin-4-yl), pyrazinyl (for example pyridazin-3-yl, pyridazin-4-yl), pyrimidinyl (for example pyrimidin-2-yl, pyrimidin-4-yl, pyrimidin-5-yl), pyrazin-2-yl, triazinyl (for example 1,3,5-triazin-2-yl, 1,2,4-triazin-3-yl, 1,2,4-triazin-5-yl, 1,2,4-triazin-6-yl);

7-membered saturated rings like azepanyl, oxepanyl, thiepanyl;

7-membered unsaturated rings azepinyl, oxepinyl, thiepinyl; and bicycles such as the benzo-fused derivatives of the abovementioned monocycles, for example quinolinyl, isoquinolinyl, indolyl, benzothienyl, benzofuranyl, benzoxazolyl, benzothiazolyl, benzisothiazolyl, benzimidazolyl, benzopyrazolyl, benzothiadiazolyl, benzotriazolyl;

haloheterocyclyl: is heterocyclyl moiety as mentioned above which is partially or fully substituted by fluorine, chlorine, bromine and/or iodine;

$C_5$-$C_6$-aryl or $C_5$-$C_6$-heteroaryl: 5- or 6-membered aromatic cycle or aromatic heterocycle, which both may have one to three nitrogen atoms and/or one or two oxygen and/or sulfur atoms: for example 5- and 6-membered unsaturated rings mentioned above and phenyl;

$C_5$-$C_6$-aryl or $C_5$-$C_6$-heteroaryl anellated with another 3-7-membered saturated, partially unsaturated or unsaturated cycloalkyl or heterocyclyl: partially unsaturated or unsaturated bicyclic heterocycle, which may comprise one to four nitrogen atoms, one or two nitrogen atoms and one sulfur atom, one nitrogen atom and one oxygen atom, one or two sulfur atoms, or one or two oxygen atoms, for example naphthyl, anthracenyl, quinolinyl, isoquinolinyl, indolyl, benzothienyl, benzofuranyl, benzoxazolyl, benzothiazolyl, benzisothiazolyl, benzimidazolyl, benzopyrazolyl, benzothiadiazolyl, benzotriazolyl.

The preferred embodiments of the invention mentioned herein below have to be understood as being preferred either independently from each other or in combination with one another.

According to a preferred embodiment of the invention preference is also given to those pyrazolopyrans of formula I wherein the variables, either independently of one another or in combination with one another, have the following meanings:

$R^1$ preferably is hydrogen, $C_1$-$C_6$-alkyl, $C_3$-$C_6$-cycloalkyl, $C_1$-$C_6$-haloalkyl, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl, more preferred is hydrogen, $C_1$-$C_6$-alkyl, $C_3$-$C_6$-cycloalkyl;

particularly preferred is $C_1$-$C_6$-alkyl;
especially preferred is methyl or ethyl;
most preferred is methyl;

$R^2$ preferably is $C_2$-$C_6$-alkyl, $C_3$-$C_6$-cycloalkyl, $C_1$-$C_6$-haloalkyl, $C_3$-$C_6$-cycloalkenyl, $C_1$-$C_6$-hydroxyalkyl, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl, 3-7-membered heterocyclyl, 3-7-membered haloheterocyclyl,
  more preferred is $C_2$-$C_6$-alkyl, $C_3$-$C_6$-cycloalkyl, $C_3$-$C_6$-cycloalkenyl, 4-6-membered heterocyclyl, 4-6-membered haloheterocyclyl,
  particularly preferred is $C_2$-$C_6$-alkyl, $C_3$-$C_6$-cycloalkyl, $C_3$-$C_6$-cycloalkenyl, and 4-6-membered heterocyclyl;
  especially preferred is ethyl, i-propyl, cyclobutyl, oxetanyl, cyclopropyl and cyclopentenyl;
  most preferred is i-propyl;

$R^3$ preferably is $C_2$-$C_6$-alkyl, $C_3$-$C_6$-cycloalkyl, $C_1$-$C_6$-haloalkyl, $C_1$-$C_6$-hydroxyalkyl, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkyl-$C_3$-$C_6$-cycloalkyl, $C_1$-$C_6$-alkyl-phenyl, $C_1$-$C_6$-haloalkyl-phenyl,
  wherin the phenyl ring can be substituted by 1-3 halogen, cyano, nitro, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_1$-$C_6$-alkylcarbonyl, hydroxycarbonyl,
$C_5$-$C_6$-aryl or $C_5$-$C_6$-heteroaryl having one to three nitrogen atoms and/or one or two oxygen and/or sulfur atoms, wherein $C_5$-$C_6$-aryl or $C_5$-$C_6$-heteroaryl may be substituted by at least one substituent of the list: 1-3 halogen, cyano, nitro, $C_1$-$C_6$-alkyl, $C_3$-$C_6$-cycloalkyl, $C_1$-$C_6$-haloalkyl, $C_1$-$C_6$-hydroxyalkyl, $C_1$-$C_6$-alkoxy-$C_1$-$C_6$-alkyl, $C_1$-$C_6$-haloalkoxy-$C_1$-$C_6$-alkyl, amino-$C_1$-$C_6$-alkyl, ($C_1$-$C_6$-alkyl)amino-$C_1$-$C_6$-alkyl, di($C_1$-$C_6$-alkyl)amino-$C_1$-$C_6$-alkyl, $C_2$-$C_6$-alkenyl, $C_2$-$C_6$-haloalkenyl, $C_2$-$C_6$-hydroxyalkenyl, $C_1$-$C_6$-alkoxy-$C_2$-$C_6$-alkenyl, $C_1$-$C_6$-haloalkoxy-$C_2$-$C_6$-alkenyl, amino-$C_2$-$C_6$-alkenyl, ($C_1$-$C_6$-alkyl)amino-$C_2$-$C_6$-alkenyl, di($C_1$-$C_6$-alkyl)amino-$C_2$-$C_6$-alkenyl, $C_2$-$C_6$-alkynyl, $C_2$-$C_6$-haloalkynyl, $C_2$-$C_6$-hydroxyalkynyl, $C_1$-$C_6$-alkoxy-$C_2$-$C_6$-alkynyl, $C_1$-$C_6$-haloalkoxy-$C_2$-$C_6$-alkynyl, amino-$C_2$-$C_6$-alkynyl, ($C_1$-$C_6$-alkyl)amino-$C_2$-$C_6$-alkynyl, di($C_1$-$C_6$-alkyl)amino-$C_2$-$C_6$-alkynyl, $C_1$-$C_6$-alkylcarbonyl, hydroxycarbonyl, $C_1$-$C_6$-alkoxycarbonyl, aminocarbonyl, ($C_1$-$C_6$-alkyl)aminocarbonyl, di($C_1$-$C_6$-alkyl)aminocarbonyl, hydroxy, $C_1$-$C_6$-alkoxy, $C_1$-$C_6$-haloalkoxy, $C_3$-$C_6$-cycloalkoxy, $C_3$-$C_6$-alkenyloxy, $C_3$-$C_6$-alkynyloxy, $C_1$-$C_6$-alkylcarbonyloxy, $C_1$-$C_6$-hydroxyalkoxy, $C_1$-$C_6$-alkoxy-$C_1$-$C_6$-alkoxy, $C_1$-$C_6$-haloalkoxy-$C_1$-$C_6$alkoxy, amino-$C_1$-$C_6$-alkoxy, ($C_1$-$C_6$-alkyl)amino-$C_1$-$C_6$-alkoxy, di($C_1$-$C_6$-alkyl)amino-$C_1$-$C_6$-alkoxy, $C_1$-$C_6$-alkylsulfonyloxy, ($C_1$-$C_6$-alkyl)amino-carbonyloxy, di($C_1$-$C_6$-alkyl)aminocarbonyloxy, $C_1$-$C_6$-alkylthio, $C_3$-$C_6$-cycloalkylthio, $C_3$-$C_6$-alkenylthio, $C_3$-$C_6$-alkynylthio, $C_1$-$C_6$-hydroxyalkylthio, $C_1$-$C_6$-alkoxy-$C_1$-$C_6$-alkylthio, $C_1$-$C_6$-haloalkoxy-$C_1$-$C_6$-alkylthio, amino-$C_1$-$C_6$-alkylthio, ($C_1$-$C_6$-alkyl)amino-$C_1$-$C_6$-alkylthio, di($C_1$-$C_6$-alkyl)amino-$C_1$-$C_6$-alkylthio, amino, $C_1$-$C_6$-alkylamino, di-($C_1$-$C_6$-alkyl)amino, $C_3$-$C_6$-cycloalkylamino, $C_3$-$C_6$-alkenylamino, $C_3$-$C_6$-alkynylamino, $C_1$-$C_6$-hydroxyalkylamino, $C_1$-$C_6$-alkoxy-$C_1$-$C_6$-alkylamino, $C_1$-$C_6$-haloalkoxy-$C_1$-$C_6$-alkylamino, amino-$C_1$-$C_6$-alkylamino, ($C_1$-$C_6$-alkyl)amino-$C_1$-$C_6$-alkylamino, di($C_1$-$C_6$-alkyl)amino-$C_1$-$C_6$-alkylamino, $C_1$-$C_6$-alkyl-sulfonylamino, $C_1$-$C_6$-haloalkylsulfonylamino, $C_1$-$C_6$-alkylsulfonyl($C_1$-$C_6$-alkyl)amino, ($C_1$-$C_6$-alkyl)aminosulfonylamino, di($C_1$-$C_6$-alkyl)aminosulfonylamino, formylamino, formyl($C_1$-$C_6$-alkyl)amino, ($C_1$-$C_6$-alkyl)carbonylamino, N($C_1$-$C_6$-alkylcarbonyl)-N($C_1$-$C_6$-alkyl)amino, ($C_1$-$C_6$-alkyl)aminocarbonylamino, di($C_1$-$C_6$-alkyl)aminocarbonylamino, ($C_1$-$C_6$-alkyl)aminocarbonyl($C_1$-$C_6$-alkyl)amino, $C_1$-$C_6$-alkylsulfinyl, $C_1$-$C_6$-alkylsulfonyl, $C_3$-$C_6$-cycloalkylsulfonyl, $C_3$-$C_6$-alkenylsulfonyl, $C_3$-$C_6$-alkynylsulfonyl, $C_1$-$C_6$-hydroxyalkylsulfonyl, $C_1$-$C_6$-alkoxy-$C_1$-$C_6$-alkylsulfonyl, $C_1$-$C_6$-haloalkoxy-$C_1$-$C_6$-alkylsulfonyl, amino-$C_1$-$C_6$-alkylsulfonyl, ($C_1$-$C_6$-alkyl)amino-$C_1$-$C_6$-alkylsulfonyl, di($C_1$-$C_6$-alkyl)amino-$C_1$-$C_6$-alkylsulfonyl, aminosulfonyl, ($C_1$-$C_6$-alkyl)aminosulfonyl, di($C_1$-$C_6$-alkyl)aminosulfonyl, phenyl, phenylcarbonyl, phenyloxy, phenylcarbonyloxy, phenylthio, phenylsulfinyl, phenylsulfonyl, phenylsulfonyloxy, phenylamino, N(phenyl)-N($C_1$-$C_6$-alkyl)amino, phenylcarbonylamino, N-phenylcarbonyl-N($C_1$-$C_6$-alkyl)amino,
  wherein each of the phenyl groups may be partially or fully halogenated and/or may carry one to three substituents selected from the group consisting of cyano, $C_1$-$C_6$-alkyl, $C_1$-$C_6$-haloalkyl, hydroxy, $C_1$-$C_6$-alkoxy, $C_1$-$C_6$-alkylcarbonyloxy, $C_1$-$C_6$-haloalkoxy, $C_3$-$C_6$-alkenyloxy, $C_3$-$C_6$-alkynyloxy, $C_1$-$C_6$-alkylthio, $C_1$-$C_6$-alkylsulfonyl, $C_1$-$C_6$-alkylsulfonylamino, $C_1$-$C_6$-haloalkylsulfonylamino;
heterocyclyl, heterocyclyl-$C_1$-$C_6$-alkyl, heterocyclyl-$C_2$-$C_6$-alkenyl, heterocyclyl-$C_2$-$C_6$-alkynyl, heterocyclyl-$C_1$-$C_6$-alkoxy, heterocyclyl-$C_1$-$C_6$-alkylthio, heterocyclyl-$C_1$-$C_6$-alkylamino, heterocyclyl-$C_1$-$C_6$-alkylsulfonyl,heterocyclyloxy, heterocyclylthio, heterocyclylsulfinyl, heterocyclylsulfonyl, heterocyclylsulfonyloxy, heterocyclyl-carbonyl, heterocyclylcarbonyloxy, heterocyclylamino, heterocyclyl-[($C_1$-$C_6$-alkyl)amino], heterocyclylcarbonylamino, heterocyclylcarbonyl[($C_1$-$C_6$-alkyl)amino],
  wherein each of the heterocyclyl groups being three- to seven-membered and having one to four nitrogen atoms, one or two nitrogen atoms and one sulfur atom, one nitrogen atom and one oxygen atom, one or two sulfur atoms, or one or two oxygen atoms, and
  wherein each of the heterocyclyl groups may be partially or fully halogenated and/or may be substituted with one to three substituents selected from the group consisting of cyano, $C_1$-$C_6$-alkyl, $C_1$-$C_6$-haloalkyl, hydroxy, mercapto, $C_1$-$C_6$-alkoxy, $C_1$-$C_6$-alkylcarbonyloxy, $C_1$-$C_6$-haloalkoxy, $C_3$-$C_6$-alkenyloxy, $C_3$-$C_6$-alkynyloxy, $C_1$-$C_6$-alkylthio, $C_1$-$C_6$-alkylsulfonyl;
more preferred is phenyl substituted by at least one substituent of the list: 1-3 halogen, cyano, $C_1$-$C_6$-alkyl, $C_1$-$C_6$-haloalkyl, $C_1$-$C_6$-alkoxy, $C_1$-$C_6$-haloalkoxy, phenyl, phenyloxy,
  wherein each of the phenyl groups may be partially or fully halogenated and/or may carry one to three substituents selected from the group consisting of cyano, $C_1$-$C_6$-alkyl, $C_1$-$C_6$-haloalkyl, $C_1$-$C_6$-alkoxy, heterocyclyl, heterocyclyl-$C_1$-$C_6$-alkyl, heterocyclyl-$C_1$-$C_6$-alkoxy, heterocyclyloxy,
  wherein each of the heterocyclyl groups being three- to seven-membered and having one to four nitrogen atoms, one or two nitrogen atoms and one sulfur atom, one nitrogen atom and one oxygen atom, one or two sulfur atoms, or one or two oxygen atoms, and
wherein each of the heterocyclyl groups may be partially or fully halogenated and/or may be substituted with one to three substituents selected from the group consisting of cyano, $C_1$-$C_6$-alkyl, $C_1$-$C_6$-haloalkyl;

particularly preferred is phenyl substituted by 1-3 halogen, cyano, $C_1$-$C_6$-alkyl, $C_1$-$C_6$-haloalkyl, $C_1$-$C_6$-alkoxy, $C_1$-$C_6$-haloalkoxy, phenyl, phenyloxy,
wherein each of the phenyl groups may be partially or fully halogenated and/or may carry one to three substituents selected from the group consisting of cyano, $C_1$-$C_6$-alkyl, $C_1$-$C_6$-haloalkyl, $C_1$-$C_6$-alkoxy;

especially preferred is phenyl substituted by 1-3 chlorine, cyano, bromine, trifluoromethyl;

most preferred is 3,5-dicyanophenyl, 3,5-dichlorophenyl, 3,4-dichlorophenyl, 3-chloro-5-cyanophenyl.

The preferred embodiments of the invention include a pyrazolopyran of formula I, wherein
$R^1$ has its broadest definition,
$R^2$ has its broadest definition and
$R^3$ has preferred or more preferred or particulary preferred or especially preferred or most preferred radical definitions
or
$R^2$ has preferred radical definitions and
$R^3$ has preferred or more preferred or particulary preferred or especially preferred or most preferred radical definitions
or
$R^2$ has more preferred radical definitions and
$R^3$ has its broadest definition or has preferred or more preferred or particulary preferred or especially preferred or most preferred radical definitions
or
$R^2$ has particulary preferred radical definitions and
$R^3$ has its broadest definition or has preferred or more preferred or particulary preferred or especially preferred or most preferred radical definitions
or
$R^2$ has especially preferred radical definitions and
$R^3$ has its broadest definition or has preferred or more preferred or particulary preferred or especially preferred or most preferred radical definitions
or
$R^2$ has most preferred radical definitions and
$R^3$ has its broadest definition or has preferred or more preferred or particulary preferred or especially preferred or most preferred radical definitions.

Further preferred embodiments of the invention include a pyrazolopyran of formula I, wherein
$R^1$ has preferred radical definitions and
$R^2$ and $R^3$ are used in combinations defined for the preferred embodiments above
or
$R^1$ has more preferred radical definitions and
$R^2$ and $R^3$ are used in combinations defined for the preferred embodiments above
or
$R^1$ has particulary preferred radical definitions and
$R^2$ and $R^3$ are used in combinations defined for the preferred embodiments above
or
$R^1$ has especially preferred radical definitions and
$R^2$ and $R^3$ are used in combinations defined for the preferred embodiments above
or
$R^1$ has most preferred radical definitions and
$R^2$ and $R^3$ are used in combinations defined for the preferred embodiments above.

Particular preference is given to pyrazolopyrans of the formula I.1

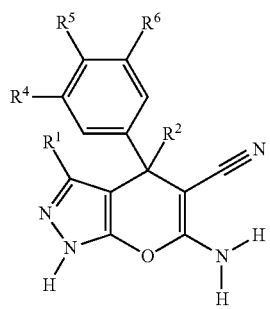

wherein the variables $R^1$ and $R^2$ have the meanings, in particular the preferred meanings, as defined above
$R^4$ and $R^5$ are hydrogen, halogen, $C_1$-$C_6$-haloalkyl or cyano; and
$R^6$ is halogen, $C_1$-$C_6$-haloalkyl or cyano.

Preferred are pyrazolopyrans of formula I.1.A, particularly preferred are pyrazolopyrans of formulae I.1.A.1 to I.1.A.180 of Table 1, wherein each line of table 1 represents one compound of formula I.1.A.

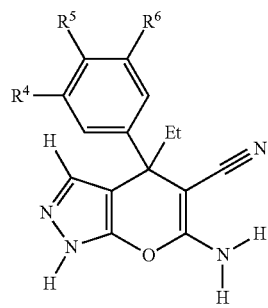

TABLE 1

| No. | $R^4$ | $R^5$ | $R^6$ |
|---|---|---|---|
| I.1.A.1. | H | H | F |
| I.1.A.2. | H | H | Cl |
| I.1.A.3. | H | H | Br |
| I.1.A.4. | H | H | $CF_3$ |
| I.1.A.5. | H | H | CN |
| I.1.A.6. | H | F | F |
| I.1.A.7. | H | F | Cl |
| I.1.A.8. | H | F | Br |
| I.1.A.9. | H | F | $CF_3$ |
| I.1.A.10. | H | F | CN |
| I.1.A.11. | H | Cl | F |
| I.1.A.12. | H | Cl | Cl |
| I.1.A.13. | H | Cl | Br |
| I.1.A.14. | H | Cl | $CF_3$ |
| I.1.A.15. | H | Cl | CN |
| I.1.A.16. | H | Br | F |
| I.1.A.17. | H | Br | Cl |

TABLE 1-continued

| No. | $R^4$ | $R^5$ | $R^6$ |
|---|---|---|---|
| I.1.A.18. | H | Br | Br |
| I.1.A.19. | H | Br | $CF_3$ |
| I.1.A.20. | H | Br | CN |
| I.1.A.21. | H | $CF_3$ | F |
| I.1.A.22. | H | $CF_3$ | Cl |
| I.1.A.23. | H | $CF_3$ | Br |
| I.1.A.24. | H | $CF_3$ | $CF_3$ |
| I.1.A.25. | H | $CF_3$ | CN |
| I.1.A.26. | H | CN | F |
| I.1.A.27. | H | CN | Cl |
| I.1.A.28. | H | CN | Br |
| I.1.A.29. | H | CN | $CF_3$ |
| I.1.A.30. | H | CN | CN |
| I.1.A.31. | F | H | F |
| I.1.A.32. | F | H | Cl |
| I.1.A.33. | F | H | Br |
| I.1.A.34. | F | H | $CF_3$ |
| I.1.A.35. | F | H | CN |
| I.1.A.36. | F | F | F |
| I.1.A.37. | F | F | Cl |
| I.1.A.38. | F | F | Br |
| I.1.A.39. | F | F | $CF_3$ |
| I.1.A.40. | F | F | CN |
| I.1.A.41. | F | Cl | F |
| I.1.A.42. | F | Cl | Cl |
| I.1.A.43. | F | Cl | Br |
| I.1.A.44. | F | Cl | $CF_3$ |
| I.1.A.45. | F | Cl | CN |
| I.1.A.46. | F | Br | F |
| I.1.A.47. | F | Br | Cl |
| I.1.A.48. | F | Br | Br |
| I.1.A.49. | F | Br | $CF_3$ |
| I.1.A.50. | F | Br | CN |
| I.1.A.51. | F | $CF_3$ | F |
| I.1.A.52. | F | $CF_3$ | Cl |
| I.1.A.53. | F | $CF_3$ | Br |
| I.1.A.54. | F | $CF_3$ | $CF_3$ |
| I.1.A.55. | F | $CF_3$ | CN |
| I.1.A.56. | F | CN | F |
| I.1.A.57. | F | CN | Cl |
| I.1.A.58. | F | CN | Br |
| I.1.A.59. | F | CN | $CF_3$ |
| I.1.A.60. | F | CN | CN |
| I.1.A.61. | Cl | H | F |
| I.1.A.62. | Cl | H | Cl |
| I.1.A.63. | Cl | H | Br |
| I.1.A.64. | Cl | H | $CF_3$ |
| I.1.A.65. | Cl | H | CN |
| I.1.A.66. | Cl | F | F |
| I.1.A.67. | Cl | F | Cl |
| I.1.A.68. | Cl | F | Br |
| I.1.A.69. | Cl | F | $CF_3$ |
| I.1.A.70. | Cl | F | CN |
| I.1.A.71. | Cl | Cl | F |
| I.1.A.72. | Cl | Cl | Cl |
| I.1.A.73. | Cl | Cl | Br |
| I.1.A.74. | Cl | Cl | $CF_3$ |
| I.1.A.75. | Cl | Cl | CN |
| I.1.A.76. | Cl | Br | F |
| I.1.A.77. | Cl | Br | Cl |
| I.1.A.78. | Cl | Br | Br |
| I.1.A.79. | Cl | Br | $CF_3$ |
| I.1.A.80. | Cl | Br | CN |
| I.1.A.81. | Cl | $CF_3$ | F |
| I.1.A.82. | Cl | $CF_3$ | Cl |
| I.1.A.83. | Cl | $CF_3$ | Br |
| I.1.A.84. | Cl | $CF_3$ | $CF_3$ |
| I.1.A.85. | Cl | $CF_3$ | CN |
| I.1.A.86. | Cl | CN | F |
| I.1.A.87. | Cl | CN | Cl |
| I.1.A.88. | Cl | CN | Br |
| I.1.A.89. | Cl | CN | $CF_3$ |
| I.1.A.90. | Cl | CN | CN |
| I.1.A.91. | Br | H | F |
| I.1.A.92. | Br | H | Cl |
| I.1.A.93. | Br | H | Br |
| I.1.A.94. | Br | H | $CF_3$ |
| I.1.A.95. | Br | H | CN |
| I.1.A.96. | Br | F | F |
| I.1.A.97. | Br | F | Cl |
| I.1.A.98. | Br | F | Br |
| I.1.A.99. | Br | F | $CF_3$ |
| I.1.A.100. | Br | F | CN |
| I.1.A.101. | Br | Cl | F |
| I.1.A.102. | Br | Cl | Cl |
| I.1.A.103. | Br | Cl | Br |
| I.1.A.104. | Br | Cl | $CF_3$ |
| I.1.A.105. | Br | Cl | CN |
| I.1.A.106. | Br | Br | F |
| I.1.A.107. | Br | Br | Cl |
| I.1.A.108. | Br | Br | Br |
| I.1.A.109. | Br | Br | $CF_3$ |
| I.1.A.110. | Br | Br | CN |
| I.1.A.111. | Br | $CF_3$ | F |
| I.1.A.112. | Br | $CF_3$ | Cl |
| I.1.A.113. | Br | $CF_3$ | Br |
| I.1.A.114. | Br | $CF_3$ | $CF_3$ |
| I.1.A.115. | Br | $CF_3$ | CN |
| I.1.A.116. | Br | CN | F |
| I.1.A.117. | Br | CN | Cl |
| I.1.A.118. | Br | CN | Br |
| I.1.A.119. | Br | CN | $CF_3$ |
| I.1.A.120. | Br | CN | CN |
| I.1.A.121. | $CF_3$ | H | F |
| I.1.A.122. | $CF_3$ | H | Cl |
| I.1.A.123. | $CF_3$ | H | Br |
| I.1.A.124. | $CF_3$ | H | $CF_3$ |
| I.1.A.125. | $CF_3$ | H | CN |
| I.1.A.126. | $CF_3$ | F | F |
| I.1.A.127. | $CF_3$ | F | Cl |
| I.1.A.128. | $CF_3$ | F | Br |
| I.1.A.129. | $CF_3$ | F | $CF_3$ |
| I.1.A.130. | $CF_3$ | F | CN |
| I.1.A.131. | $CF_3$ | Cl | F |
| I.1.A.132. | $CF_3$ | Cl | Cl |
| I.1.A.133. | $CF_3$ | Cl | Br |
| I.1.A.134. | $CF_3$ | Cl | $CF_3$ |
| I.1.A.135. | $CF_3$ | Cl | CN |
| I.1.A.136. | $CF_3$ | Br | F |
| I.1.A.137. | $CF_3$ | Br | Cl |
| I.1.A.138. | $CF_3$ | Br | Br |
| I.1.A.139. | $CF_3$ | Br | $CF_3$ |
| I.1.A.140. | $CF_3$ | Br | CN |
| I.1.A.141. | $CF_3$ | $CF_3$ | F |
| I.1.A.142. | $CF_3$ | $CF_3$ | Cl |
| I.1.A.143. | $CF_3$ | $CF_3$ | Br |
| I.1.A.144. | $CF_3$ | $CF_3$ | $CF_3$ |
| I.1.A.145. | $CF_3$ | $CF_3$ | CN |
| I.1.A.146. | $CF_3$ | CN | F |
| I.1.A.147. | $CF_3$ | CN | Cl |
| I.1.A.148. | $CF_3$ | CN | Br |
| I.1.A.149. | $CF_3$ | CN | $CF_3$ |
| I.1.A.150. | $CF_3$ | CN | CN |
| I.1.A.151. | CN | H | F |
| I.1.A.152. | CN | H | Cl |
| I.1.A.153. | CN | H | Br |
| I.1.A.154. | CN | H | $CF_3$ |
| I.1.A.155. | CN | H | CN |
| I.1.A.156. | CN | F | F |
| I.1.A.157. | CN | F | Cl |
| I.1.A.158. | CN | F | Br |
| I.1.A.159. | CN | F | $CF_3$ |
| I.1.A.160. | CN | F | CN |
| I.1.A.161. | CN | Cl | F |
| I.1.A.162. | CN | Cl | Cl |
| I.1.A.163. | CN | Cl | Br |
| I.1.A.164. | CN | Cl | $CF_3$ |
| I.1.A.165. | CN | Cl | CN |
| I.1.A.166. | CN | Br | F |
| I.1.A.167. | CN | Br | Cl |
| I.1.A.168. | CN | Br | Br |
| I.1.A.169. | CN | Br | $CF_3$ |
| I.1.A.170. | CN | Br | CN |
| I.1.A.171. | CN | $CF_3$ | F |
| I.1.A.172. | CN | $CF_3$ | Cl |
| I.1.A.173. | CN | $CF_3$ | Br |

TABLE 1-continued

| No. | R⁴ | R⁵ | R⁶ |
|---|---|---|---|
| I.1.A.174. | CN | CF₃ | CF₃ |
| I.1.A.175. | CN | CF₃ | CN |
| I.1.A.176. | CN | CN | F |
| I.1.A.177. | CN | CN | Cl |
| I.1.A.178. | CN | CN | Br |
| I.1.A.179. | CN | CN | CF₃ |
| I.1.A.180. | CN | CN | CN |

Also preferred are pyrazolopyrans of formula I.1.B, particularly preferred are pyrazolopyrans of formulae I.1.B.1 to I.1.B.180, where the definitions of the variables $R^4$, $R^5$ and $R^6$ correspond to those of compounds I.1.A.1 to I.1.A.180 of Table 1.

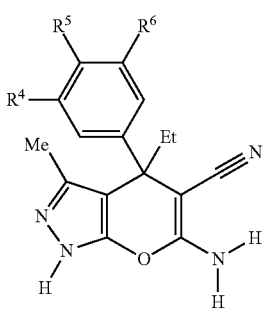

I.1.B

Also preferred are pyrazolopyrans of formula I.1.C, particularly preferred are pyrazolopyrans of formulae I.1.C.1 to I.1.C.180, where the definitions of the variables $R^4$, $R^5$ and $R^6$ correspond to those of compounds I.1.A.1 to I.1.A.180 of Table 1.

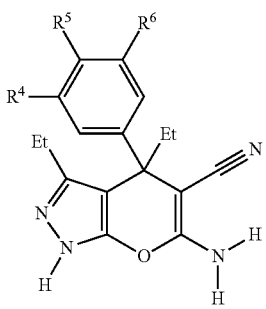

I.1.C

Also preferred are pyrazolopyrans of formula I.1.D, particularly preferred are pyrazolopyrans of formulae I.1.D.1 to I.1.D.180, where the definitions of the variables $R^4$, $R^5$ and $R^6$ correspond to those of compounds I.1.A.1 to I.1.A.180 of Table 1.

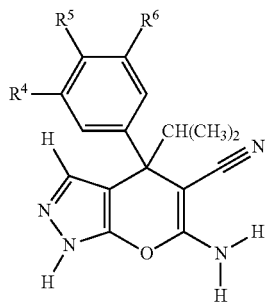

I.1.D

Also preferred are pyrazolopyrans of formula I.1.E, particularly preferred are pyrazolopyrans of formulae I.1.E.1 to I.1.E.180, where the definitions of the variables $R^4$, $R^5$ and $R^6$ correspond to those of compounds I.1.A.1 to I.1.A.180 of Table 1.

I.1.E

Also preferred are pyrazolopyrans of formula I.1.F, particularly preferred are pyrazolopyrans of formulae I.1.F.1 to I.1.F.180, where the definitions of the variables $R^4$, $R^5$ and $R^6$ correspond to those of compounds I.1.A.1 to I.1.A.180 of Table 1.

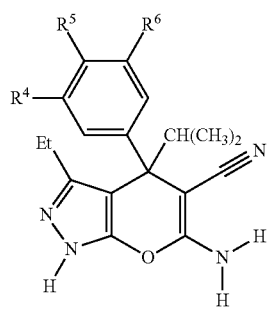

I.1.F

Also preferred are pyrazolopyrans of formula I.1.G, particularly preferred are pyrazolopyrans of formulae I.1.G.1 to I.1.G.180, where the definitions of the variables $R^4$, $R^5$ and $R^6$ correspond to those of compounds I.1.A.1 to I.1.A.180 of Table 1.

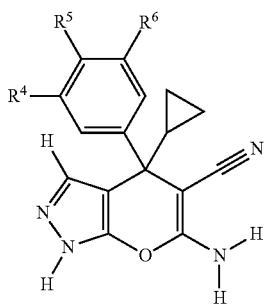

I.1.G

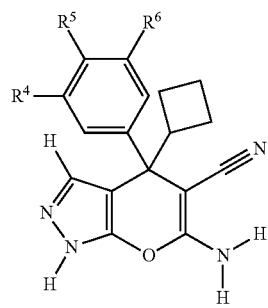

I.1.J

Also preferred are pyrazolopyrans of formula I.1.H, particularly preferred are pyrazolopyrans of formulae I.1.H.1 to I.1.H.180, where the definitions of the variables $R^4$, $R^5$ and $R^6$ correspond to those of compounds I.1.A.1 to I.1.A.180 of Table 1.

Also preferred are pyrazolopyrans of formula I.1.K, particularly preferred are pyrazolopyrans of formulae I.1.K.1 to I.1.K.180, where the definitions of the variables $R^4$, $R^5$ and $R^6$ correspond to those of compounds I.1.A.1 to I.1.A.180 of Table 1.

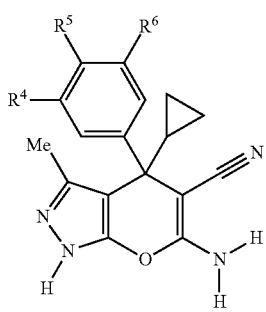

I.1.H

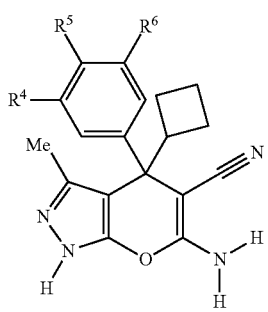

I.1.K

Also preferred are pyrazolopyrans of formula I.1.I, particularly preferred are pyrazolopyrans of formulae I.1.I.1 to I.1.I.180, where the definitions of the variables $R^4$, $R^5$ and $R^6$ correspond to those of compounds I.1.A.1 to I.1.A.180 of Table 1.

Also preferred are pyrazolopyrans of formula I.1.L, particularly preferred are pyrazolopyrans of formulae I.1.L.1 to I.1.L.180, where the definitions of the variables $R^4$, $R^5$ and $R^6$ correspond to those of compounds I.1.A.1 to I.1.A.180 of Table 1.

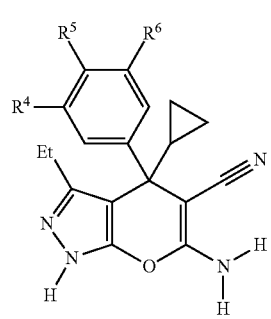

I.1.I

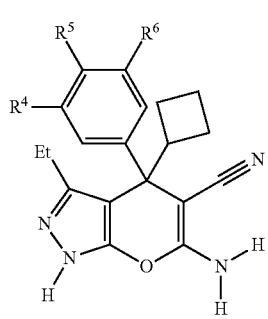

I.1.L

Also preferred are pyrazolopyrans of formula I.1.J, particularly preferred are pyrazolopyrans of formulae I.1.J.1 to I.1.J.180, where the definitions of the variables $R^4$, $R^5$ and $R^6$ correspond to those of compounds I.1.A.1 to I.1.A.180 of Table 1.

Also preferred are pyrazolopyrans of formula I.1.M, particularly preferred are pyrazolopyrans of formulae I.1.M.1 to I.1.M.180, where the definitions of the variables $R^4$, $R^5$ and $R^6$ correspond to those of compounds I.1.A.1 to I.1.A.180 of Table 1.

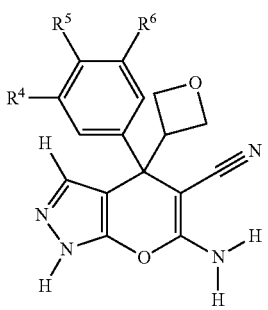

I.1.M

Also preferred are pyrazolopyrans of formula I.1.N, particularly preferred are pyrazolopyrans of formulae I.1.N.1 to I.1.N.180, where the definitions of the variables $R^4$, $R^5$ and $R^6$ correspond to those of compounds I.1.A.1 to I.1.A.180 of Table 1.

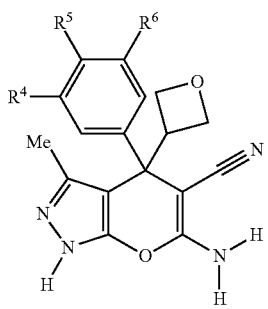

I.1.N

Also preferred are pyrazolopyrans of formula I.1.O, particularly preferred are pyrazolopyrans of formulae I.1.O.1 to I.1.O.180, where the definitions of the variables $R^4$, $R^5$ and $R^6$ correspond to those of compounds I.1.A.1 to I.1.A.180 of Table 1.

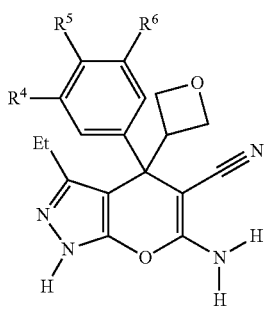

I.1.O

A pyrazolopyran of formula I according to the invention can be prepared by standard processes of organic chemistry, for example by the following processes:

Process A)

A pyrazolopyran of formula I can be obtained by condensation of a ketone of formula II with malodinitrile to the vinyldinitrile of formula III and subsequent cyclization with a hydroxypyrazole IV:

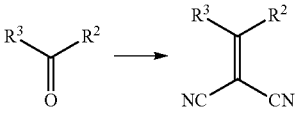
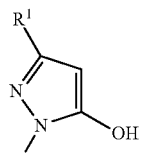
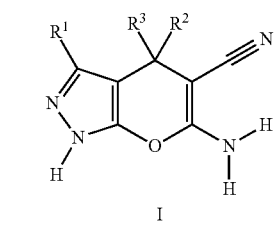

The condensation of the ketone of formula II with malodinitrile is usually carried out at a temperature from 20° C. to the boiling point of the reaction mixture, preferably from 50° C. to 150° C., particularly preferably from 80° C. to 150° C., in an inert organic solvent optionally in the presence of dehydrating agent.

The condensation of the vinyldinitrile of formula III with the hydroxypyrazole of the formula IV is usually carried out at a temperature from 20° C. to the boiling point of the reaction mixture, preferably from 50° C. to 150° C., particularly preferably at from 80° C. to 150° C., in an inert organic solvent optionally in the presence of dehydrating agent.

Suitable solvents for both steps are aliphatic hydrocarbons such as $C_5$-$C_8$-alkanes, e.g. pentane, hexane, cyclohexane and mixtures of $C_5$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methylether, dioxane, anisole and tetrahydrofuran, nitriles such as acetonitrile and propionitrile, ketones such as acetone, methyl ethyl ketone, diethyl ketone and tert-butyl methyl ketone, alkoholes such as methanol, ethanol, n-propanol, isopropanol, n-butanol, isobutanol and tert.-butanol, as well as dimethylsulfoxide, dimethylformamide and N,N-dimethylacetamide or N-methylpyrrolidone. Particular preference is given to alkoholes such as methanol, ethanol, n-propanol, isopropanol, n-butanol, isobutanol and tert.-butanol. It is also possible to use mixtures of the solvents mentioned.

In both steps the dehydration is preferably performed by e.g. aceotropic removal of water, addition of magnesium-sulfate, titanium tetraisopropoxide or titanium trichloride.

The reaction mixtures in both steps may be worked up in a known manner, for example by mixing with water, separation of the phases and, if appropriate, chromatographic purification of the crude product. Some of the intermediates and end products are obtained in the form of viscous oils, which can be purified or freed from volatile components under reduced pressure and at moderately elevated temperature. If the intermediates and the end products are obtained as solid, purification can also be carried out by recrystallisation or digestion.

Alternatively, the two reaction steps can be carried out as a one-pot synthesis.

The ketones of formula II are either known or commertially available or can be prepared according to methods generally known from literature.

The hydroxypyrazole of the formula VI are either known or commertially available or can be prepared according to methods generally known from literature. They can also be prepared in a one-pot-procedure and directly condensed in a four component condensation to a pyrazolopyran of formula I (Kanagaraj et al, Tetrahedron Lett. 2010, 3312-3316).

A pyrazolopyran of formula I is suitable as a herbicide. It is suitable as such or as an appropriately formulated herbicidal composition. Herbicidal compositions comprising a pyrazolopyran of formula I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, a pyrazolopyran of formula I as such or in form of herbicidal compositions can additionally be employed in a further number of crop plants for eliminating undesirable plants. Examples of suitable crops are the following: *Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N.rustica*), *Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor* (*s. vulgare*), *Theobroma cacao, Trifolium pratense, Triticum aestivum, Triticale, Triticum durum, Vicia faba, Vitis vinifera* and *Zea mays*.

Preferred crops are the following: *Arachis hypogaea, Beta vulgaris* spec. *altissima, Brassica napus* var. *napus, Brassica oleracea, Citrus limon, Citrus sinensis, Coffea arabica* (*Coffea canephora, Coffea liberica*), *Cynodon dactylon, Glycine max, Gossypium hirsutum,* (*Gossypium arboreum, Gossypium herbaceum, Gossypium vitifolium*), *Helianthus annuus, Hordeum vulgare, Juglans regia, Lens culinaris, Linum usitatissimum, Lycopersicon lycopersicum, Malus* spec., *Medicago sativa, Nicotiana tabacum* (*N. rustica*), *Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor* (*s. vulgare*), *Triticale, Triticum aestivum, Triticum durum, Vicia faba, Vitis vinifera* and *Zea mays*.

A pyrazolopyran of formula I according to the invention can also be used in genetically modified plants. The term "genetically modified plants" is to be understood as plants, which genetic material has been modified by the use of recombinant DNA techniques in a way that under natural circumstances it cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s), oligo- or polypeptides e. g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxyphenylpyruvate dioxygenase (HPPD) inhibitors or phytoene desaturase (PDS) inhibitors; acetolactate synthase (ALS) inhibitors such as sulfonyl ureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering; inhibitors of serinhydroxymethylthansferase (SHMT). Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as ä-endotoxins, e.g. Cry1A(b), Cry1A(c), CryIF, CryIF(a2), Cry1lA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (*Coeloptera*), two-winged insects (*Diptera*), and moths (*Lepidoptera*) and to nematodes (*Nematoda*). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); BtXtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars produ-cing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e. g. potato cultivars, which express resistance genes acting against *Phytophthora infestans* derived from the mexican wild potato *Solanum bulbocastanum*) or T4-lyso-zym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

A pyrazolopyran of formula I, or the herbicidal compositions according to the invention comprising a pyrazolopyran of formula I, can be used, for example, in form of ready-to-spray aqueous solutions, powders, suspensions, also highly concentrated aqueous, oily or other suspensions or dispersions, emulsions, oil dispersions, pastes, dusts, materials for broadcasting, or granules, by means of spraying, atomizing, dusting, spreading, watering or treatment of the seed or mixing with the seed. The use forms depend on the intended purpose; in any case, they should ensure the finest possible distribution of the active ingredients according to the invention.

The herbicidal compositions comprise an herbicidal effective amount of a pyrazolopyran of the formula I and auxiliaries customary for formulating crop protection agents.

Examples of auxiliaries customary for the formulation of crop protection agents are inert auxiliaries, solid carriers, surfactants (such as dispersants, protective colloids, emulsifiers, wetting agents and tackifiers), organic and inorganic thickeners, bactericides, antifreeze agents, antifoams, optionally colorants and, for seed formulations, adhesives. The person skilled in the art is sufficiently familiar with the recipes for such formulations.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R.T. Vanderbilt), and also organic and inorganic sheet minerals, such as Attaclay® (from Engelhardt).

Examples of antifoams are silicone emulsions (such as, for example, Silikon SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations. Examples of bactericides are bactericides based on diclorophen and benzyl alcohol hemiformal (Proxel® from ICI or Acticide® RS from Thor Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments and water-soluble dyes, e.g. the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

Suitable inert auxiliaries are, for example, the following: mineral oil fractions of medium to high boiling point, such as kerosene and diesel oil; furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone or strongly polar solvents, for example amines such as N-methylpyrrolidone, and water.

Suitable carriers include liquid and solid carriers. Liquid carriers include e.g. non-aqeuos solvents such as cyclic and aromatic hydrocarbons, e.g. paraffins, tetrahydronaphtalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water as well as mixtures thereof. Solid carriers include e.g. mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutyl-naphthalenesulfonic acid (Nekal types, BASF AG), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denaturated proteins, polysaccharides (e.g. methylcellulose), hydrophobically modified starches, polyvinyl alcohol (Mowiol types Clariant), polycarboxylates (BASF AG, Sokalan types), polyalkoxylates, polyvinylamine (BASF AG, Lupamine types), polyethyleneimine (BASF AG, Lupasol types), polyvinylpyrrolidone and copolymers thereof.

Powders, materials for broadcasting and dusts can be prepared by mixing or concomitant grinding the active ingredients together with a solid carrier.

Granules, for example coated granules, impregnated granules and homogeneous granules, can be prepared by binding the active ingredients to solid carriers.

Aqueous use forms can be prepared from emulsion concentrates, suspensions, pastes, wettable powders or water-dispersible granules by adding water.

To prepare emulsions, pastes or oil dispersions, a pyrazolopyran of formula I, either as such or dissolved in an oil or solvent, can be homogenized in water by means of a wetting agent, tackifier, dispersant or emulsifier. Alternatively, it is also possible to prepare concentrates comprising active compound, wetting agent, tackifier, dispersant or emulsifier and, if desired, solvent or oil, which are suitable for dilution with water.

The concentrations of a pyrazolopyran of formula I in the ready-to-use preparations (formulations) can be varied within wide ranges. In general, the formulations comprise approximately from 0.001 to 98% by weight, preferably 0.01 to 95% by weight of at least one active ingredient. The active ingredients are employed in a purity of from 90% to 100%, preferably 95% to 100% (according to NMR spectrum).

In formulations of a pyrazolopyran of formula I according to the present invention the active ingredients are present in suspended, emulsified or dissolved form. Formulations according to the invention can be in form of aqueous solutions, powders, suspensions, also highly concentrated aqueous, oily or other suspensions or dispersions, aqueous emulsions, aqueous microemulsions, aqueous suspo-emulsions, oil dispersions, pastes, dusts, materials for spreading or granules.

A pyrazolopyran of formula I can, for example, be formulated as follows:

1. Products for Dilution with Water

A Water-Soluble Concentrates 10 parts by weight of active compound are dissolved in 90 parts by weight of water or a water-soluble solvent. As an alternative, wetters or other adjuvants are added. The active compound dissolves upon dilution with water. This gives a formulation with an active compound content of 10% by weight.

B Dispersible Concentrates 20 parts by weight of active compound are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates 15 parts by weight of active compound are dissolved in 75 parts by weight of an organic solvent (eg. alkylaromatics) with addition of calcium dodecylbenzenesulfonate and castor oil ethoxylate (in each case 5 parts by weight). Dilution with water gives an emulsion. The formulation has an active compound content of 15% by weight.

D Emulsions 25 parts by weight of active compound are dissolved in 35 parts by weight of an organic solvent (eg. alkylaromatics) with addition of calcium dodecylbenzenesulfonate and castor oil ethoxylate (in each case 5 parts by weight). This mixture is introduced into 30 parts by weight of water by means of an emulsifier (Ultraturrax) and made into a homogeneous emulsion. Dilution with water gives an emulsion. The formulation has an active compound content of 25% by weight.

E Suspensions

In an agitated ball mill, 20 parts by weight of active compound are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F Water-dispersible granules and water-soluble granules 50 parts by weight of active compound are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders 75 parts by weight of active compound are ground in a rotor-stator mill with addition of 25 parts by weight of dispersants, wetters and silica gel. Dilution with water gives a stable dispersion or solution of the active compound. The active compound content of the formulation is 75% by weight.

H Gel Formulations

In a ball mill, 20 parts by weight of active compound, 10 parts by weight of dispersant, 1 part by weight of gelling agent and 70 parts by weight of water or of an organic solvent are mixed to give a fine suspension. Dilution with water gives a stable suspension with active compound content of 20% by weight.

2. Products to be Applied Undiluted

I Dusts 5 parts by weight of active compound are ground finely and mixed intimately with 95 parts by weight of finely divided kaolin. This gives a dusting powder with an active compound content of 5% by weight.

J Granules (GR, FG, GG, MG)

0.5 parts by weight of active compound are ground finely and associated with 99.5 parts by weight of carriers. Current methods here are extrusion, spray-drying or the fluidized bed. This gives granules to be applied undiluted with an active compound content of 0.5% by weight.

K ULV solutions (UL)

10 parts by weight of active compound are dissolved in 90 parts by weight of an organic solvent, for example xylene. This gives a product to be applied undiluted with an active compound content of 10% by weight.

Aqueous use forms can be prepared from emulsion concentrates, suspensions, pastes, wettable powders or water-dispersible granules by adding water.

Application can be done before, during and/or after, preferably during and/or after, the emergence of the undesirable plants.

A pyrazolopyran of formula I as such or in form of a herbicidal composition can be applied pre-, post-emergence or pre-plant, or together with the seed of a crop plant. It is also possible to apply the herbicidal composition or active compounds by applying seed, pretreated with the herbicidal compositions or active compounds, of a crop plant. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

In a further embodiment, a pyrazolopyran of the formula I as such or in form of herbicidal compositions can be applied by treating seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on a pyrazolopyran of formula I according to the invention or the compositions prepared therefrom. Here, the herbicidal compositions can be applied diluted or undiluted.

The term "seed" comprises seed of all types, such as, for example, corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods.

The rates of application of a pyrazolopyran of formula I according to the present invention (total amount of pyrazolopyran of formula I) are from 0.1 g/ha to 3000 g/ha, preferably 10 g/ha to 1000 g/ha of active substance (a.s.), depending on the control target, the season, the target plants and the growth stage.

In another preferred embodiment of the invention, the application rates of a pyrazolopyran of formula I are in the range from 0.1 g/ha to 5000 g/ha and preferably in the range from 1 g/ha to 2500 g/ha or from 5 g/ha to 2000 g/ha of active substance (a.s.).

In another preferred embodiment of the invention, the application rate of the pyrazolopyran of formula I is 0.1 to 1000 g/ha, preferably 1 to 750 g/ha, more preferably 5 to 500 g/ha, of active substance.

To treat the seed, a pyrazolopyran of formula I is generally employed in amounts of from 0.001 to 10 kg per 100 kg of seed.

To widen the spectrum of action and to achieve synergistic effects, a pyrazolopyran of formula I may be mixed with a large number of representatives of other herbicidal or growth-regulating active ingredient groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, 2-hetaroyl-1,3-cyclohexanediones, hetaryl aryl ketones, benzylisoxazolidinones, meta-CF3-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides, uracils, phenyl pyrazolines and isoxazolines and derivatives thereof.

It may furthermore be beneficial to apply a pyrazolopyran of formula I alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

Moreover, it may be useful to apply a pyrazolopyran of formula I in combination with safeners. Safeners are chemical compounds which prevent or reduce damage on useful plants without having a major impact on the herbicidal action of a pyrazolopyran of formula I towards unwanted plants. They can be applied either before sowings (e.g. on seed treatments, shoots or seedlings) or in the pre-emergence application or post-emergence application of the useful plant. The safeners and a pyrazolopyran of formula I can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl)-3-isoxazol carboxylic acids, dichloroacetamides, alphaoximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such as amides, esters, and thioesters, provided they have an acid group.

A pyrazolopyran of formula I according to the present invention can be used as a pharmaceutically active ingredient (medicament), especially for treating or preventing infections, preferably parasitic and/or bacterial infections.

Parasitic and bacterial infections can occur in humans and animals.

Examples for parasitic infections are coccidiosis and toxoplasmosis. These parasitic infections are caused by parasitic Protozoa, e.g. of the genus *Eimeria* (e.g. the species *E. tenella* and *E. necatrix*) and Toxoplasma (e.g. the species *T. gondii*). *Eimeria* and *Toxoplasma* both belong to the order of *Eucoccidiorida*. *Eucoccidiorida* belongs to the phylum *Apicomplexa*. *Aplicomplexa* is an example for "parasitic Protozoa".

Examples for bacterial infections are tuberculosis, mycetoma, listeriosis, meningitis, botulism, tetanus, urethritis, pelvic inflammatoric disease, typhoid fever, paratyphoid fever and foodborne illness salmonellosis. These infections are caused by bacteria, e.g. of the genus *Mycobacterium* (e.g the species *M. tuberculosis*), *Streptomyces* (e.g. the species *S. sudanensis*, *S. somaliensis*), *Listeria* (e.g. the species *L. monocytogenes*), *Clostridium* (e.g. the species *C. botulinum*, *C. difficile*, *C. perfringens*, *C. tetani*), *Chlamydia* (e.g. the species *C. pneumoniae*) and *Salmonella* (e.g. the species *S. bongori*, *S. enterica* containing the sub-subspecies *S. typhi* and *S. typhimurium*). *Mycobacterium* and *Streptomyces* both belong to the order of *Actinomycetales*, whereas *Listeria* belongs to the order of *Bacillaes*, *Clostridium* belongs to the order of *Clostridiales*, *Chlamydia* belongs to the order of *Chlamydiales* and *Salmonella* belongs to the order of *Enterobacteriales*. *Actinomycetales* of the phylum Actinobacteria as well as *Bacillaes* and *Clostridiales*, both of the phylum *Firmicutes*, are examples for Gram-positive bacteria. *Chlamydiales* (phylum Clamydiae) and *Enterobacteriales* (phylum Gamma Probacteria) are both examples for Gram-negative bacteria.

In one embodiment of the invention, the pyrazolopyrans of formula I are used as pharmaceutical active ingredients for treating or preventing parasitic and/or bacterial infections caused by *Apicomplexa* selected from the order *Eucoccidiorida* and/or Gram-positive bacteria.

In another embodiment of the invention, the pyrazolopyrans of formula I are used as pharmaceutical active ingredients for treating or preventing parasitic infections caused by Apicomplexa selected from the order *Eucoccidiorida*, particularly preferred caused by Eimeria and Toxoplasma, most preferably caused *E. tenella* and *T. gondii*.

In another embodiment of the invention, the pyrazolopyrans of formula I are used as pharmaceutical active ingredients for treating or preventing bacterial infections caused by *Actinobacteria, Firmicutes, Chlamydiae* and Gamma Probacteria, preferably caused by *Actinomycetales, Bacillaes, Clostridiales, Chlamydiales* and *Enterocbacteriales*, more preferably caused by *Mycobacterium, Streptomyces, Listeria, Clostridium, Chlamydia* and *Salmonella* particularly preferred caused by *Mycobacterium, Streptomyces, Listeria* and *Clostridium*, especially preferred caused by *Mycobacterium, Listeria* and *Clostridium*.

In another embodiment of the invention, the pyrazolopyrans of formula I are used as pharmaceutical active ingredients for treating or preventing bacterial infections caused by Gram-positive bacteria, preferably caused by Actinobacteria and Firmicutes, more preferably caused by *Actinomycetales, Bacillaes* and *Clostridiales*, particularly preferred caused by *Mycobacterium, Streptomyces, Listeria* and *Clostridium*, especially preferred caused by *M. tuberculosis, L. monocytogenes, C. botulinum* and *C. tetani;* most preferably caused by *M. tuberculosis, C. botulinum* and *C. tetani*.

In another embodiment of the invention, the pyrazolopyrans of formula I are used as pharmaceutical active ingredients for treating or preventing bacterial infections caused by Gram-negative bacteria, preferably caused by *Chlamydiales* and *Enterobacteriales*, more preferably caused by *Chlamydia* and *Salmonella*, particularly preferred caused by *C. pneumoniae, S. bongori* and *S. enterica*.

A pyrazolopyran of formula I together with auxiliaries customary for formulating pharmaceutical, e.g. one or more conventional adjuvants, carriers, or diluents, may be placed into the form of pharmaceutical compositions and unit dosages thereof.

In such form a pyrazolopyran of formula I may be employed as solid, such as coated or uncoated tablets or filled capsules, or liquid, such as solutions, suspensions, emulsions, elixirs, or capsules filled with the same, all for oral use; in the form of suppositories or capsules for rectal administration or in the form of sterile injectable solutions for parenteral, including intravenous or subcutaneous, use.

Such pharmaceutical compositions and unit dosage forms thereof may comprise conventional or new ingredients in conventional or special proportions, with or without additional active compounds or principles, and such unit dosage forms may contain any suitable effective amount of the active ingredient commensurate with the intended daily dosage range to be employed. Tablets containing from 0.1 to 600 milligrams of active ingredient, more preferred from 0.5 to 500 milligrams per tablet, are suitable representative unit dosage forms.

The term "carrier" applied to pharmaceutical compositions of the invention refers to a diluent, excipient or vehicle with which an active compound is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. A. R. Gennaro, 20th Edition, describes suitable pharmaceutical carriers in "Remington: The Science and Practice of Pharmacy".

Due to their high degree of activity, the high metabolic stability and their low toxicity, together presenting favorable therapeutic index, a pyrazolopyran of formula I of the invention may be administered to a subject, e.g., a living animal (including a human) body in need thereof, for the treatment, alleviation, or amelioration, palliation, or elimination of an indication or condition which is susceptible thereto, or representatively of an indication or condition set forth elsewhere in this application, preferably concurrently, simultaneously, or together with one or more pharmaceutically-acceptable excipients, carriers or diluents.

Suitable dosage ranges are 0.1 to 1000 milligrams daily, preferably 1 to 500 milligrams daily, and especially 5 to 500 milligrams daily, depending as usual upon the exact mode of administration, form in which administered, the indication toward which the administration is directed, the subject involved and the body weight of the subject involved, and the preference and experience of the physician or veterinarian in charge.

A pyrazolopyran of formula I may be administered orally, topically, parenterally (including intravenous and subcutaneous), or mucosally (e.g., buccally, by inhalation, or rectally) in dosage unit formulations containing conventional non-toxic pharmaceutically acceptable carriers.

It is usually desirable to use the oral route. The active agents may be administered orally in the form of a capsule, a tablet, or the like (see Remington: The Science and Practice of Pharmacy, 20th Edition). The orally administered medicaments may be administered in the form of a time-controlled release vehicle, including diffusion-controlled systems, osmotic devices, dissolution-controlled matrices, and erodible/degradable matrices.

For oral administration in the form of a tablet or capsule, a pyrazolopyran of formula I may be combined with a non-toxic, pharmaceutically acceptable excipients such as binding agents (e.g., pregelatinized maize starch, polyvinylpyrrolidone or hydroxypropyl methylcellulose); fillers (e.g., lactose, sucrose, glucose, mannitol, sorbitol and other reducing and non-reducing sugars, microcrystalline cellulose, calcium sulfate, or calcium hydrogen phosphate); lubricants (e.g., magnesium stearate, talc, or silica, steric acid, sodium stearyl fumarate, glyceryl behenate, calcium stearate, and the like); disintegrants (e.g., potato starch or sodium starch glycolate); or wetting agents (e.g., sodium lauryl sulphate), coloring and flavoring agents, gelatin, sweeteners, natural and synthetic gums (such as acacia, tragacanth or alginates), buffer salts, carboxymethyl-cellulose, polyethyleneglycol, waxes, and the like. For oral administration in liquid form, the drug components may be combined with non-toxic, pharmaceutically acceptable inert carriers (e.g., ethanol, glycerol, water), suspending agents (e.g., sorbitol syrup, cellulose derivatives or hydrogenated edible fats), emulsifying agents (e.g., lecithin or acacia), non-aqueous vehicles (e.g., almond oil, oily esters, ethyl alcohol or fractionated vegetable oils), preservatives (e.g., methyl or propyl-p-hydroxybenzoates or sorbic acid), and the like. Stabilizing agents such as antioxidants (BHA, BHT, propyl gallate, sodium ascorbate, citric acid) may also be added to stabilize the dosage forms.

The tablets containing as active compound a pyrazolopyran of formula I may be coated by methods well known in the art. The compositions of the invention containing as active compound a pyrazolopyran of formula I may be also introduced in beads, microspheres or microcapsules, e.g., fabricated from polyglycolic acid/lactic acid (PGLA). Liquid preparations for oral administration may take the form of, for example, solutions, syrups, emulsions or suspensions, or they may be presented as a dry product for reconstitution with water or other suitable vehicle before use. Preparations for oral administration may be suitably formulated to give controlled or postponed release of the active compound.

A pyrazolopyran of formula I may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines, as is well known. Drugs of the invention containing as active compound a compound of formula I may also be delivered by the use of monoclonal antibodies as individual carriers to which the compound molecules are coupled. Active drugs may also be coupled with soluble polymers as targetable drug carriers. Such polymers include polyvinyl-pyrrolidone, pyran copolymer, polyhydroxy-propyl methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxybutyric acid, polyorthoesters, polyacetals, polyhydropyrans, polycyanoacrylates, and cross-linked or amphipathic block copolymers of hydrogels.

For administration by inhalation, the therapeutics according to the present invention containing as active compound a pyrazolopyran of formula I may be conveniently delivered in the form of an aerosol spray presentation from pressurized packs or a nebulizer, with the use of a suitable propellant, e.g., dichlorodifluoromethane, trichlorofluoromethane, dichlorotetra-fluoroethane, carbon dioxide, or other suitable gas. In the case of a pressurized aerosol, the dosage unit may be determined by providing a valve to deliver a metered amount. Capsules and cartridges of, e.g., gelatin for use in an inhaler or insufflator can be formulated containing a powder mix of the compound and a suitable powder base such as lactose or starch.

The formulations of the invention containing a pyrazolopyran of formula I may be delivered parenterally, i.e., by intravenous (i.v.), intracerebroventricular (i.c.v.), subcutaneous (s.c.), intraperitoneal (i.p.), intramuscular (i.m.), subdermal (s.d.), or intradermal (i.d.) administration, by direct injection, via, for example, bolus injection or continuous infusion. Formulations for injection can be presented in unit dosage form, e.g., in ampoules or in multi-dose containers, with an added preservative. The compositions can take such forms as excipients, suspensions, solutions, or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water, before use.

Compositions of the present invention containing a pyrazolopyran of formula I may also be formulated for rectal administration, e.g., as suppositories or retention enemas (e.g., containing conventional suppository bases such as cocoa butter or other glycerides).

The compositions containing a pyrazolopyran of formula I may, if desired, be presented in a pack or dispenser device, which may contain one or more unit dosage forms containing the active ingredient and/or may contain different dosage levels to facilitate dosage titration. The pack may, for example, comprise metal or plastic foil, such as a blister pack.

Compositions of the invention formulated in a compatible pharmaceutical carrier may also be prepared, placed in an appropriate container, and labeled for treatment of an indicated condition.

As disclosed herein, the dose of the components in the compositions of the present invention is determined to ensure that the dose administered continuously or intermittently will not exceed an amount determined after consideration of the results in test animals and the individual conditions of a patient.

A specific dose naturally varies depending on the dosage procedure, the conditions of a patient or a subject animal such as age, body weight, sex, sensitivity, feed, dosage period, drugs used in combination, seriousness of the disease. The appropriate dose and dosage times under certain conditions can be determined by the test based on the above-described indices but may be refined and ultimately decided according to the judgment of the practitioner and each patient's circumstances (age, general condition, severity of symptoms, sex, etc.) according to standard clinical techniques.

Toxicity and therapeutic efficacy of the compositions of the invention can be determined by standard pharmaceutical procedures in experimental animals, e.g., by determining the LD50 (the dose lethal to 50% of the population) and the ED50 (the dose therapeutically effective in 50% of the population). The dose ratio between therapeutic and toxic effects is the therapeutic index and it may be expressed as the ratio ED50/LD50. Compositions that exhibit large therapeutic indices are preferred.

Hereinbelow, the preparation of the pyrazolopyrans of the formula I is illustrated by examples; however, the subject matter of the present invention is not limited to the examples given.

Preparation of
3,5-dibromo-N-methoxy-N-methyl-benzamide

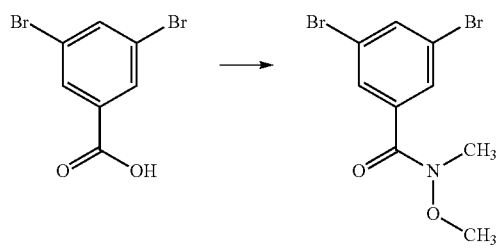

A solution of 3,5-dibromobenzoic acid (112 g, 0.4 mol) and carbonyldiimidazole (24 g, 149 mmol) in 1000 ml DCM was stirred at rt for 1 h. Methoxymethylamine (71.3 g, 0.44 mol) was added, and the mixture was stirred at roomtemperature for 18 h. Filtration was done and the filtrate was washed with saturated NaHCO3 solution and brine, dried over anhydrous Na2SO4, filtered and the filtrate was evaporated to give 3,5-dibromo-N-methoxy-N-methyl-benzamide (360 g, yield 93.1%).

Preparation of
1-(3,5-dibromophenyl)-2-methyl-propan-1-one

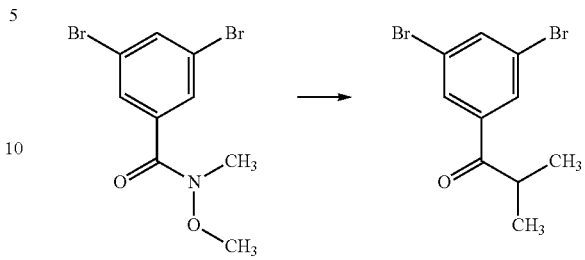

A solution of 3,5-dibromo-N-methoxy-N-methyl-benzamide (60 g, 186 mmol) in 2 L anhydrous Et$_2$O was added i-PrMgCI (2M in Et$_2$O, 140 mL, 164 mmol) dropwise at rt under N$_2$ atmosphere. The mixture was stirred at rt overnight, then quenched with sat. NH$_4$Cl, extracted with EtOAc, washed with brine, dried over anhydrous Na$_2$SO$_4$, to give the crude product after concentration. The crude product was purified by column chromatography (Petrolether: EtOAc=200:1) to give 1-(3,5-dibromophenyl)-2-methyl-propan-1-one (128 g, yield 37.4%).

Preparation of
5-(2-methylpropanoyl)benzene-1,3-dicarbonitrile

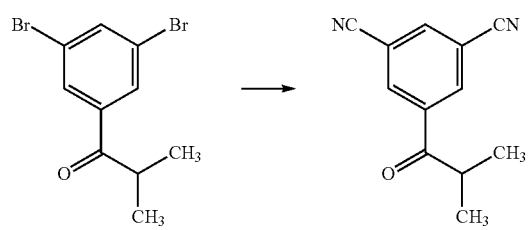

A solution of 1-(3,5-dibromophenyl)-2-methyl-propan-1-one (128 g, 417 mmol), Zn(CN)$_2$ (145 g, 1.25 mol), Zn (2.71 g, 41.7 mmol) and dppf (17.6 g, 31.3 mmol) in 2.5 l dixoane was flushed with N$_2$ for 10 min, then was added Pd(dba)2 (19.1 g, 20.9 mmol). The mixture was stirred at 100° C. overnight, filtered and evaporated. The resulting crude product was purified by silicon-gel column (Petrolether: EtOAc=5:1) to give 56 g of 5-(2-methylpropanoyl)benzene-1,3-dicarbonitrile (yield: 67.8%).

$^1$H NMR (400 MHz, CDCl$_3$): d 8.41 (s, 2H), 8.10 (s, 1H), 3.47 (quintet, 1H, J=6.8 Hz), 1.25 (d, 6H, J=4.8 Hz).

Preparation of 5-[1-(dicyanomethylene)-2-methyl-propyl]benzene-1,3-dicarbonitrile

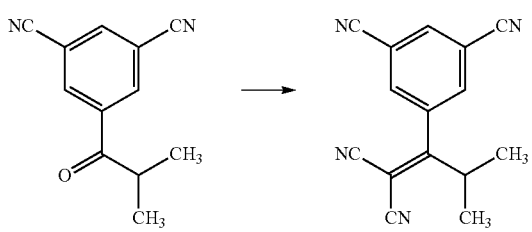 [SMILES: CC(C)C(=O)c1cc(C#N)cc(C#N)c1 ; CC(C)C(=C(C#N)C#N)c1cc(C#N)cc(C#N)c1]

A solution of 5-(2-methylpropanoyl)benzene-1,3-dicarbonitrile (7.5 g, 38 mmol)was dissolved in chloroform (30 ml) and malodinitrile (10 g, 152 mmol), titaniumtetrachloride (1 M in CHCl3; 38 ml, 38 mmol) and pyridine (6.1 ml, 76 mmol) were added. The solution was refluxed for 48 h. After cooling the solution it was added to 2N HCl (30 ml) and extracted with methylenchloride and the organic phase dried with sodiumsulfate. After evaporation of the solvents the residue was chromatographed on silica with cyclohexane/ethylacetate gradient to yield 8.0 g 5-[1-(dicyanomethylene)-2-methyl-propyl]benzene-1,3-dicarbonitrile (86% yield) as colorless solid.

LCMS: M+H=247.1
$^1$H NMR (400 MHz, CDCl$_3$): 8.45 (s, 2H; 8.10 (s, 1H); 3.50 (m, 1H); 1.25 (d, 1H)

Preparation of 5-(6-amino-5-cyano-4-isopropyl-3-methyl-1H-pyrano[2,3-c]pyrazol-4-yl)benzene-1,3-dicarbonitrile A solution of 5-[1-(dicyanomethylene)-2-methyl-propyl]benzene-1,3-dicarbonitrile (2.2 g, 8.9 mmol) and 3-hydroxy-5-methylpyrazole (0.88 g, 8.9 mmol) in ethanol (6 ml) dioxane (6 ml) and piperidine (3 drops) was heated for 3 h at 65° C.. in the microwave. After cooling water was added and extracted with ethylacetate. The organic phase was dried with sodiumsulfate and the solvents evaporated. The residue was was chromatographed on silica with cyclohexane/ethylacetate gradient to yield 0.66 g 5-(6-amino-5-cyano-4-isopropyl-3-methyl-1H-pyrano[2,3-c]pyrazol-4-yl)benzene-1,3-dicarbonitrile (21% yield) als colourless solid.

LCMS: M+H=345.1
$^1$H NMR (400 MHz, DMSO-d6): 12.3 (s, NH); 8.40 (s, 1H; 8.18 (s, 2H); 7.2 (s, NH2); 2.85 (m, 1H); 1.75 (s, 3H); 0.90 (d, 3H); 0.75 (d, 3H)

Further pyrazolopyrans of formula I have been prepared in accordance to the processes described above, and are, in addition to the compounds mentioned above, listed in tables 2 to 4 below.

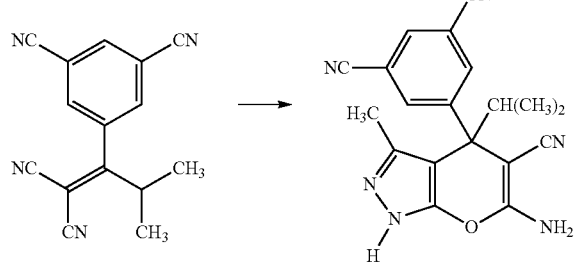

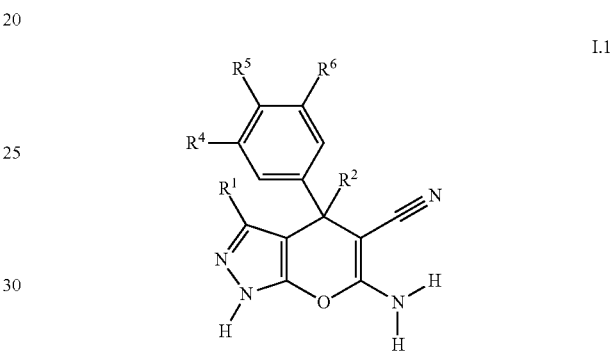

I.1

TABLE 2

| No | R$^1$ | R$^2$ | R$^4$ | R$^5$ | R$^6$ | LCMS (M + H) | ED50 SHMT |
|---|---|---|---|---|---|---|---|
| 2.1. | CH$_3$ | C$_2$H$_5$ | OC$_6$H$_5$ | H | H | 373.2 | <1e-7M |
| 2.2. | CH$_3$ | C$_2$H$_5$ | H | F | H | 299.2 | <1e-5M |
| 2.3. | CH$_3$ | C$_2$H$_5$ | H | CH$_3$ | H | 294.2 | |
| 2.4. | CH$_3$ | C$_2$H$_5$ | Br | H | H | 359.0 | <1e-6M |
| 2.5. | CH$_3$ | C$_2$H$_5$ | H | CH(CH$_3$)$_2$ | H | 323.2 | |
| 2.6. | CH$_3$ | C$_2$H$_5$ | H | NHCOCH$_3$ | H | 338.2 | <1e-5M |
| 2.7. | CH$_3$ | C$_2$H$_5$ | H | C(CH$_3$)$_3$ | H | 337.2 | <1e-5M |
| 2.8. | CH$_3$ | C$_2$H$_5$ | H | OC$_6$H$_5$ | H | 373.2 | <1e-6M |
| 2.9. | CH$_3$ | C$_2$H$_5$ | F | H | H | 316.2 | <1e-6M |
| 2.10. | CH$_3$ | C$_2$H$_5$ | H | Cl | H | 316.2 | <1e-5M |
| 2.11. | CH$_3$ | C$_2$H$_5$ | OC$_6$H$_5$ | F | H | 391.1 | <1e-6M |
| 2.12. | CH$_3$ | C$_2$H$_5$ | Cl | H | Cl | 349.2 | <1e-7M |
| 2.13. | CH$_3$ | C$_2$H$_5$ | Br | F | H | 376.0 | <1e-6M |
| 2.14. | CH$_3$ | C$_2$H$_5$ | Cl | Cl | H | 349.2 | <1e-7M |
| 2.15. | CH$_3$ | C$_2$H$_5$ | F | H | H | 299.2 | <1e-5M |
| 2.16. | CH$_3$ | C$_2$H$_5$ | F | F | H | 317.2 | <1e-5M |
| 2.17. | CH$_3$ | C$_2$H$_5$ | F | H | F | 317.2 | <1e-6M |
| 2.18. | CH$_3$ | C$_2$H$_5$ | F | F | F | 335.2 | <1e-6M |
| 2.19. | CH$_3$ | C$_2$H$_5$ | Cl | F | H | 333.2 | <1e-7M |
| 2.20. | CH$_3$ | C$_2$H$_5$ | F | H | Cl | 333.2 | <1e-6M |
| 2.21. | CH$_3$ | C$_2$H$_5$ | OCH$_3$ | OCH$_3$ | H | 341.2 | <1e-6M |
| 2.22. | CH$_3$ | C$_2$H$_5$ | H | OCH$_3$ | H | 311.2 | <1e-6M |
| 2.23. | CH$_3$ | C$_2$H$_5$ | CH$_3$ | O-(2-Cl-4-CF$_3$—C$_6$H$_3$) | H | 489.1 | <1e-5M |
| 2.24. | CH$_3$ | C$_2$H$_5$ | CH$_3$ | CH$_3$ | H | 310.2 | <1e-6M |
| 2.25. | CH$_3$ | C$_2$H$_5$ | CH$_3$ | OH | H | 311.2 | <1e-6M |
| 2.26. | CH$_3$ | C$_2$H$_5$ | H | OSO$_2$C$_2$H$_5$ | H | 389.1 | <1e-5M |
| 2.27. | CH$_3$ | C$_2$H$_5$ | H | OC(CH$_3$)$_3$ | H | 352.2 | <1e-5M |
| 2.28. | CH$_3$ | C$_2$H$_5$ | H | OCH$_2$C$_6$H$_5$ | H | 387.2 | <1e-6M |
| 2.29. | CH$_3$ | C$_2$H$_5$ | F | CF$_3$ | H | 367.1 | <1e-5M |
| 2.30. | CH$_3$ | C$_2$H$_5$ | H | CF$_3$ | H | 349.2 | <1e-5M |
| 2.31. | CH$_3$ | C$_2$H$_5$ | CF$_3$ | H | H | 349.2 | <1e-6M |
| 2.32. | CH$_3$ | C$_2$H$_5$ | H | OCHF$_2$ | H | 347.2 | <1e-5M |
| 2.33. | CH$_3$ | C$_2$H$_5$ | CF$_3$ | H | F | 367.1 | <1e-7M |
| 2.34. | CH$_3$ | C$_2$H$_5$ | F | OH | F | 333.2 | <1e-5M |

TABLE 2-continued

| No | R$^1$ | R$^2$ | R$^4$ | R$^5$ | R$^6$ | LCMS (M + H) | ED50 SHMT |
|---|---|---|---|---|---|---|---|
| 2.35. | CH$_3$ | C$_2$H$_5$ | C$_6$H$_5$ | H | H | 357.2 | <1e-6M |
| 2.36. | CH$_3$ | C$_2$H$_5$ | H | OC$_6$H$_{13}$ | H | 381.2 | <1e-5M |
| 2.37. | CH$_3$ | C$_2$H$_5$ | NO$_2$ | OH | H | 342.2 | <1e-6M |
| 2.38. | CH$_3$ | C$_2$H$_5$ | H | N(CH$_3$)$_2$ | H | 324.2 | |
| 2.39. | CH$_3$ | C$_2$H$_5$ | H | NHCOC(CH$_3$)$_3$ | H | 380.2 | <1e-6M |
| 2.40. | CH$_3$ | C$_2$H$_5$ | H | NO$_2$ | H | 326.2 | <1e-6M |
| 2.41. | CH$_3$ | C$_2$H$_5$ | H | F | H | 407.0 | <1e-5M |
| 2.42. | CH$_3$ | C$_2$H$_5$ | CH$_3$ | H | H | 294.2 | <1e-5M |
| 2.43. | CH$_3$ | C$_2$H$_5$ | NO$_2$ | OCH$_2$COOC$_2$H$_5$ | H | 427.1 | <1e-6M |
| 2.44. | CH$_3$ | C$_2$H$_5$ | H | 2-F—C$_6$H$_4$ | H | 375.1 | <1e-6M |
| 2.45. | CH$_3$ | C$_2$H$_5$ | F | OCH$_3$ | F | 347.2 | <1e-6M |
| 2.46. | CH$_3$ | cyclopropyl | H | Cl | H | 327.2 | <1e-6M |
| 2.47. | CH$_3$ | C$_2$H$_5$ | CF$_3$ | H | CF$_3$ | 417.1 | <1e-7M |
| 2.48. | CH$_3$ | C$_2$H$_5$ | CH$_3$ | OCO(2-Cl-6-Cl—C$_6$H$_3$) | H | 484.1 | <1e-5M |
| 2.49. | CH$_3$ | C$_2$H$_5$ | CH$_3$ | OCOC$_6$H$_5$ | H | 415.1 | <1e-6M |
| 2.50. | CH$_3$ | C$_2$H$_5$ | CH$_3$ | OCO(2-CF$_3$—C$_6$H$_4$) | H | 483.1 | <1e-6M |
| 2.51. | CH$_3$ | C$_2$H$_5$ | CH$_3$ | OCO(morpholinyl) | H | 424.1 | <1e-6M |
| 2.52. | CH$_3$ | C$_2$H$_5$ | CH$_3$ | OCOC(CH$_3$)$_3$ | H | 395.1 | <1e-6M |
| 2.53. | CH$_3$ | C$_2$H$_5$ | CH$_3$ | OCO(picolinyl) | H | 422.1 | <1e-6M |
| 2.54. | CH$_3$ | C$_2$H$_5$ | CH$_3$ | OSO$_2$CH(CH$_3$)$_2$ | H | 417.1 | <1e-6M |
| 2.55. | CH$_3$ | C$_2$H$_5$ | CH$_3$ | OSO$_2$CH$_2$C$_6$H$_5$ | H | 465.1 | <1e-6M |
| 2.56. | CH$_3$ | C$_2$H$_5$ | CH$_3$ | OSO$_2$(3-Cl-4-Cl—C$_6$H$_3$) | H | 519.1 | <1e-5M |
| 2.57. | CH$_3$ | C$_2$H$_5$ | CH$_3$ | OSO$_2$(4-Cl—C$_6$H$_4$) | H | 485.1 | <1e-6M |
| 2.58. | CH$_3$ | C$_2$H$_5$ | CH$_3$ | OSO$_2$C$_6$H$_5$ | H | 451.1 | <1e-6M |
| 2.59. | CH$_3$ | C$_2$H$_5$ | CH$_3$ | OSO$_2$(2-Cl-4-Cl—C$_6$H$_3$) | H | 519.1 | <1e-5M |
| 2.60. | CH$_3$ | cyclopropyl | CF$_3$ | H | H | 361.1 | <1e-6M |
| 2.61. | CH$_3$ | cyclopropyl | Cl | H | Cl | 361.1 | <1e-6M |
| 2.62. | H | C$_2$H$_5$ | Cl | H | Cl | 335.0 | <1e-5M |
| 2.63. | H | C$_2$H$_5$ | CF$_3$ | H | H | 335.2 | <1e-5M |
| 2.64. | H | C$_2$H$_5$ | CF$_3$ | H | CF$_3$ | 403.1 | <1e-6M |
| 2.65. | CH$_3$ | C$_2$H$_5$ | CF$_3$ | F | H | 367.1 | <1e-6M |
| 2.66. | CH$_2$OCH$_3$ | C$_2$H$_5$ | Cl | H | H | 345.2 | <1e-6M |
| 2.67. | C$_2$H$_5$ | C$_2$H$_5$ | Cl | H | H | 329.2 | |
| 2.68. | CH$_3$ | CF$_3$ | NO$_2$ | H | H | 366.1 | <1e-6M |
| 2.69. | CH$_3$ | cyclopropyl | Cl | H | F | 345.2 | |
| 2.70. | CH$_3$ | cyclopropyl | Cl | H | H | 327.2 | |
| 2.71. | CH$_3$ | cyclopropyl | Cl | F | H | 345.2 | |
| 2.72. | CH$_3$ | C$_2$H$_5$ | O-(2,2-diF-cyclopropyl) | H | H | 373.1 | |
| 2.73. | CH$_3$ | C$_2$H$_5$ | CF$_3$ | H | CF$_3$ | 429.1 | <1e-6M |
| 2.74. | CH$_3$ | cyclopropyl | CF$_3$ | H | F | 379.1 | |
| 2.75. | CH$_3$ | C$_2$H$_5$ | H | H | H | 361.1 | |
| 2.76. | CH$_3$ | cyclopropyl | O-(3-F—C$_6$H$_4$) | H | H | 403.1 | |
| 2.77. | CH$_3$ | C$_2$H$_5$ | CF$_3$ | Cl | H | 383.1 | |
| 2.78. | CH$_3$ | CH$_2$SCH$_3$ | CF$_3$ | H | CF$_3$ | 449.1 | |
| 2.79. | CH$_3$ | C$_2$H$_5$ | H | Cl | H | 319.2 | <1e-5M |
| 2.80. | CH$_3$ | C$_2$H$_5$ | H | NHCOOCH$_3$ | H | 354.1 | <1e-6M |
| 2.81. | CH$_3$ | C$_2$H$_5$ | H | NHCOC$_2$H$_5$ | H | 352.2 | <1e-6M |
| 2.82. | CH$_2$OCH$_3$ | C$_2$H$_5$ | CF$_3$ | H | CF$_3$ | 447.1 | <1e-6M |
| 2.83. | C$_3$H$_7$ | C$_2$H$_5$ | CF$_3$ | H | CF$_3$ | 445.1 | <1e-6M |
| 2.84. | C$_2$H$_5$ | C$_2$H$_5$ | CF$_3$ | H | CF$_3$ | 431.1 | <1e-7M |
| 2.85. | C$_3$H$_7$ | C$_2$H$_5$ | Cl | H | H | 343.2 | <1e-5M |
| 2.86. | CH$_3$ | C$_2$H$_5$ | CF$_3$ | H | OC$_6$H$_5$ | 441.1 | <1e-6M |
| 2.87. | CH$_3$ | CF$_3$ | Cl | H | H | 355.0 | <1e-5M |
| 2.88. | CH$_3$ | CF$_3$ | Cl | H | Cl | 389.0 | <1e-6M |
| 2.89. | CH$_3$ | C$_3$H$_7$ | Cl | H | Cl | 363.1 | <1e-6M |
| 2.90. | CH$_3$ | C$_3$H$_7$ | Cl | H | Cl | 363.1 | <1e-6M |
| 2.91. | CH$_3$ | C$_4$H$_9$ | Cl | H | H | 343.2 | <1e-5M |
| 2.92. | CH$_3$ | C$_4$H$_9$ | Cl | H | Cl | 377.1 | <1e-5M |
| 2.93. | CH$_3$ | C$_4$H$_9$ | Cl | H | Cl | 377.1 | <1e-5M |
| 2.94. | CH$_3$ | C$_3$H$_7$ | Cl | H | H | 329.2 | <1e-6M |
| 2.95. | CH$_3$ | CF$_3$ | CF$_3$ | H | H | 389.1 | <1e-6M |
| 2.96. | CH$_3$ | CF$_2$CF$_3$ | H | Cl | H | 405.0 | |
| 2.97. | CH$_2$OCH$_3$ | C$_2$H$_5$ | CF$_3$ | H | H | 378.1 | <1e-5M |
| 2.98. | C$_2$H$_5$ | C$_2$H$_5$ | CF$_3$ | H | H | 363.1 | <1e-6M |
| 2.99. | C$_3$H$_7$ | C$_2$H$_5$ | CF$_3$ | H | H | 377.1 | <1e-5M |
| 2.100. | CH$_3$ | CH$_2$CH$_2$CN | Cl | H | H | 340.2 | <1e-5M |
| 2.101. | CH$_3$ | CH$_2$CH$_2$CF$_3$ | CF$_3$ | H | H | 417.1 | <1e-5M |
| 2.102. | C$_2$H$_5$ | CH$_2$CH$_2$CF$_3$ | CF$_3$ | H | H | 431.1 | |
| 2.103. | C$_3$H$_7$ | cyclopropyl | CF$_3$ | H | H | 289.2 | <1e-6M |
| 2.104. | C$_2$H$_5$ | cyclopropyl | CF$_3$ | H | H | 375.1 | <1e-6M |
| 2.105. | CH$_2$CH$_2$CHF$_2$ | C$_2$H$_5$ | Cl | H | H | 379.1 | <1e-5M |
| 2.106. | CH$_2$CH$_2$CHF$_2$ | C$_2$H$_5$ | CF$_3$ | H | H | 413.1 | <1e-6M |
| 2.107. | CH$_2$CH$_2$CHF$_2$ | C$_2$H$_5$ | CF$_3$ | H | CF$_3$ | 481.1 | <1e-6M |
| 2.108. | CH$_3$ | CH$_2$CH(CH$_3$)$_2$ | CF$_3$ | H | CF$_3$ | 445.1 | <1e-7M |
| 2.109. | C$_2$H$_5$ | C$_2$H$_5$ | Cl | H | Cl | 363.1 | <1e-6M |
| 2.110. | C$_3$H$_7$ | C$_2$H$_5$ | Cl | H | Cl | 377.1 | <1e-6M |
| 2.111. | CH$_3$ | cyclopropyl | CH$_3$ | OH | H | 323.2 | <1e-5M |

TABLE 2-continued

| No | R¹ | R² | R⁴ | R⁵ | R⁶ | LCMS (M + H) | ED50 SHMT |
|---|---|---|---|---|---|---|---|
| 2.112. | CH₃ | CH(CH₃)₂ | Cl | H | Cl | 363.1 | <1e-8M |
| 2.113. | CH₃ | C₂H₅ | Cl | H | OC₆H₅ | 407.1 | <1e-7M |
| 2.114. | C₂H₅ | cyclopropyl | H | Cl | H | 341.2 | <1e-7M |
| 2.115. | C₃H₇ | cyclopropyl | H | Cl | H | 355.1 | <1e-7M |
| 2.116. | CH(CH₃)₂ | C₂H₅ | Cl | H | H | 343.2 | <1e-6M |
| 2.117. | CH(CH₃)₂ | C₂H₅ | Cl | H | H | 341.2 | <1e-5M |
| 2.118. | CH(CH₃)₂ | C₂H₅ | CF₃ | H | H | 377.1 | <1e-6M |
| 2.119. | cyclopropyl | C₂H₅ | CF₃ | H | H | 375.1 | <1e-6M |
| 2.120. | CH(CH₃)₂ | C₂H₅ | CF₃ | H | CF₃ | 445.1 | <1e-7M |
| 2.121. | cyclopropyl | C₂H₅ | CF₃ | H | CF₃ | 443.1 | <1e-7M |
| 2.122. | CH₃ | CH(CH₃)₂ | Cl | H | H | 329.2 | <1e-7M |
| 2.123. | CH₃ | CH(CH₃)₂ | H | SCH₃ | H | 341.2 | <1e-7M |
| 2.124. | CH₃ | CH(CH₃)₂ | Cl | OCH₃ | H | 359.1 | <1e-8M |
| 2.125. | CH₃ | CH₂CH(CH₃)₂ | Cl | H | Cl | 377.1 | <1e-7M |
| 2.126. | CH₃ | CH₂CH(CH₃)₂ | Cl | H | H | 343.2 | <1e-6M |
| 2.127. | C₂H₅ | CH(CH₃)₂ | H | F | H | 327.2 | |
| 2.128. | CH(CH₃)₂ | cyclopropyl | H | Cl | H | 355.1 | <1e-5M |
| 2.129. | cyclopropyl | cyclopropyl | H | Cl | H | 353.1 | <1e-5M |
| 2.130. | C₂H₅ | C₂H₅ | H | OC₆H₅ | H | 387.2 | <1e-6M |
| 2.131. | cyclopropyl | C₂H₅ | H | OC₆H₅ | H | 399.1 | <1e-5M |
| 2.132. | CH(CH₃)₂ | C₂H₅ | Cl | H | Cl | 377.1 | <1e-6M |
| 2.133. | cyclopropyl | C₂H₅ | Cl | H | Cl | 375.1 | <1e-6M |
| 2.134. | CH₃ | CH(CH₃)₂ | Cl | F | H | 347.2 | <1e-7M |
| 2.135. | CH₃ | CH(CH₃)₂ | Cl | Cl | H | 363.1 | <1e-7M |
| 2.136. | cyclopropyl | CH(CH₃)₂ | Cl | H | Cl | 389.1 | <1e-7M |
| 2.137. | CH₃ | CH(CH₃)₂ | CF₃ | H | H | 363.1 | <1e-7M |
| 2.138. | CH₃ | cyclobutyl | H | Cl | H | 341.2 | <1e-6M |
| 2.139. | C₂H₅ | cyclobutyl | H | Cl | H | 355.1 | <1e-6M |
| 2.140. | cyclopropyl | cyclobutyl | H | Cl | H | 367.1 | <1e-5M |
| 2.141. | CH₃ | CH₂CH(CH₃)₂ | Cl | Cl | H | 377.1 | <1e-6M |
| 2.142. | CH₃ | CH₂CH(CH₃)₂ | H | Cl | H | 343.2 | <1e-5M |
| 2.143. | CH₃ | CH(CH₃)₂ | H | Cl | H | 329.2 | <1e-6M |
| 2.144. | CH₃ | CH(CH₃)₂ | CF₃ | OCH₃ | H | 393.1 | <1e-8M |
| 2.145. | CH₃ | CH(CH₃)₂ | H | OCF₃ | H | 378.1 | <1e-6M |
| 2.146. | CH₃ | cyclopropyl | Br | H | Cl | 405.0 | |
| 2.147. | C₂H₅ | CH(CH₃)₂ | Cl | OCH₃ | H | 373.1 | <1e-6M |
| 2.148. | cyclopropyl | CH(CH₃)₂ | Cl | OCH₃ | H | 385.1 | <1e-6M |
| 2.149. | CH₃ | cyclopropyl | Cl | OCH₃ | H | 357.1 | <1e-7M |
| 2.150. | CH₃ | cyclopropyl | CF₃ | OCH₃ | H | 391.1 | <1e-7M |
| 2.151. | C₂H₅ | cyclopropyl | Cl | OCH₃ | H | 371.1 | <1e-6M |
| 2.152. | C₂H₅ | cyclopropyl | CF₃ | OCH₃ | H | 405.1 | <1e-6M |
| 2.153. | CH₃ | cyclopropyl | Cl | H | OC₆H₅ | 419.1 | <1e-7M |
| 2.154. | CH₃ | cyclobutyl | Cl | H | Cl | 375.1 | <1e-8M |
| 2.155. | C₂H₅ | cyclobutyl | Cl | H | Cl | 389.1 | <1e-7M |
| 2.156. | cyclopropyl | cyclobutyl | Cl | H | Cl | 402.1 | <1e-7M |
| 2.157. | CH₃ | cyclobutyl | Cl | H | F | 359.1 | <1e-7M |
| 2.158. | CH₃ | cyclobutyl | H | H | H | 373.1 | <1e-7M |
| 2.159. | CH₃ | cyclobutyl | H | H | H | 385.1 | <1e-7M |
| 2.160. | CH(CH₃)₂ | C₂H₅ | H | OC₆H₅ | H | 401.1 | <1e-5M |
| 2.161. | CH₃ | CH(CH₃)₂ | H | H | H | 313.2 | <1e-6M |
| 2.162. | C₂H₅ | C₂H₅ | CH₃ | O(2-Cl-4-CF₃—C₆H₃) | H | 503.1 | |
| 2.163. | CH(CH₃)₂ | C₂H₅ | CH₃ | O(2-Cl-4-CF₃—C₆H₃) | H | 517.2 | |
| 2.164. | cyclopropyl | C₂H₅ | CH₃ | O(2-Cl-4-CF₃—C₆H₃) | H | 515.2 | <1e-5M |
| 2.165. | CHF₂ | C₂H₅ | Cl | H | H | 351.1 | <1e-6M |
| 2.166. | CHF₂ | C₂H₅ | CF₃ | H | CF₃ | 453.1 | <1e-7M |
| 2.167. | CH₃ | CH(CH₃)₂ | H | OCH₃ | H | 325.2 | <1e-6M |
| 2.168. | CHF₂ | cyclobutyl | Cl | H | Cl | 411.1 | <1e-7M |
| 2.169. | CH₃ | cyclobutyl | CF₃ | H | H | 375.1 | <1e-8M |
| 2.170. | C₂H₅ | cyclobutyl | CF₃ | H | H | 389.1 | <1e-7M |
| 2.171. | cyclopropyl | cyclobutyl | CF₃ | H | H | 401.1 | <1e-7M |
| 2.172. | CH₃ | cyclobutyl | Cl | H | H | 341.2 | <1e-7M |
| 2.173. | C₂H₅ | cyclobutyl | Cl | H | H | 355.1 | <1e-7M |
| 2.174. | cyclopropyl | cyclobutyl | Cl | H | H | 367.1 | <1e-7M |
| 2.175. | CHF₂ | cyclobutyl | CF₃ | H | H | 411.1 | <1e-6M |
| 2.176. | CH₃ | cyclobutyl | CF₃ | OCH₃ | H | 405.1 | <1e-8M |
| 2.177. | CH₃ | cyclopropyl | O(3-Cl-5-Cl—C₆H₃) | H | Cl | 455.1 | <1e-6M |
| 2.178. | CH₃ | cyclobutyl | Cl | OCH₃ | H | 371.1 | <1e-8M |
| 2.179. | CH₃ | cyclobutyl | OC₆H₅ | H | Cl | 433.1 | <1e-6M |
| 2.180. | CH₃ | 1-F-cyclobutyl | Cl | H | Cl | 393.1 | <1e-7M |
| 2.181. | CH₃ | CH(CH₃)₂ | Cl | H | Cl | 349.2 | <1e-7M |
| 2.182. | CH₃ | cyclobutyl | Cl | F | H | 359.1 | <1e-7M |
| 2.183. | CH₃ | cyclopropyl | H | OCF₃ | H | 391.1 | <1e-6M |
| 2.184. | CH₃ | cyclopropyl | Cl | H | C₆H₅ | 403.1 | <1e-7M |
| 2.185. | CH₃ | CH(CH₃)₂ | Cl | OCH₂C₆H₅ | H | 435.1 | <1e-7M |
| 2.186. | CH₃ | cyclopropyl | Cl | OCH₂C₆H₅ | H | 433.1 | <1e-7M |
| 2.187. | CH₃ | cyclopropyl | 3-F—C₆H₅ | H | Cl | 421.1 | <1e-7M |
| 2.188. | CH₃ | cyclopropyl | S—CF₃—C₆H₅ | H | Cl | 471.1 | <1e-7M |

TABLE 2-continued

| No | $R^1$ | $R^2$ | $R^4$ | $R^5$ | $R^6$ | LCMS (M + H) | ED50 SHMT |
|---|---|---|---|---|---|---|---|
| 2.189. | $CH_3$ | cyclopropyl | Cl | H | $O(4\text{-F}—C_6H_4)$ | 437.1 | <1e-7M |
| 2.190. | $CH_3$ | cyclopropyl | $O(3\text{-F}—C_6H_4)$ | H | Cl | 437.1 | <1e-7M |
| 2.191. | $CH_3$ | cyclobutyl | $CF_3$ | H | $CF_3$ | 443.1 | <1e-7M |
| 2.192. | $CH_3$ | cyclobutyl | CN | H | H | 332.2 | <1e-7M |
| 2.193. | $CH_3$ | cyclobutyl | Cl | Cl | H | 375.1 | <1e-8M |
| 2.194. | $CHF_2$ | cyclobutyl | CN | H | H | 368.1 | <1e-6M |
| 2.195. | H | cyclobutyl | $CF_3$ | H | H | 361.1 | <1e-6M |
| 2.196. | $CH_2OCH_3$ | cyclobutyl | $CF_3$ | H | H | 405.1 | <1e-6M |
| 2.197. | $C_6H_{13}$ | $C_2H_5$ | Cl | H | H | 385.1 | <1e-6M |
| 2.198. | $CH_3$ | cyclobutyl | 3-thienyl | H | Cl | 423.1 | <1e-8M |
| 2.199. | $CH_3$ | cyclopentyl | Cl | H | Cl | 389.1 | <1e-6M |
| 2.200. | $CH_3$ | cyclobutyl | $O(3\text{-F}—C_6H_4)$ | H | Cl | 451.1 | <1e-7M |
| 2.201. | $CH_3$ | cyclobutyl | $O(4\text{-F}—C_6H_4)$ | H | Cl | 451.1 | <1e-7M |
| 2.202. | $CH_3$ | cyclopentyl | $CF_3$ | H | $CF_3$ | 557.1 | <1e-7M |
| 2.203. | $CH_3$ | cyclopentyl | Cl | $OCH_3$ | H | 385.1 | <1e-6M |
| 2.204. | OH | $C_2H_5$ | Cl | H | H | 317.2 | |
| 2.205. | H | $CH_2CH(CH_3)_2$ | Cl | H | Cl | 363.1 | <1e-5M |
| 2.206. | $CH_3$ | cyclohexyl | Cl | H | Cl | 404.1 | <1e-5M |
| 2.207. | $CH_3$ | cyclobutyl | Br | H | Cl | 419.0 | <1e-8M |
| 2.208. | $CH_3$ | cyclobutyl | Br | $OCH_3$ | H | 415.1 | <1e-8M |
| 2.209. | $CH_3$ | cyclobutyl | Cl | Cl | Cl | 409.0 | <1e-8M |
| 2.210. | $CH_3$ | cyclopentyl | Cl | Cl | H | 389.1 | <1e-7M |
| 2.211. | $CH_3$ | cyclopentyl | Cl | H | H | 355.1 | <1e-7M |
| 2.212. | $CH_3$ | cyclohexyl | Cl | Cl | H | 404.1 | <1e-5M |
| 2.213. | $CH_3$ | cyclopentyl | $CF_3$ | H | H | 389.1 | <1e-8M |
| 2.214. | $CH_3$ | 1-F-cyclopropyl | Cl | H | Cl | 379.0 | <1e-8M |
| 2.215. | $CH_3$ | cyclopentyl | $CF_3$ | $OCH_3$ | H | 419.1 | <1e-8M |
| 2.216. | $CH_3$ | cyclobutyl | $CF_3$ | H | $CF_3$ | 429.1 | <1e-8M |
| 2.217. | $CHF_2$ | cyclobutyl | $CF_3$ | H | $CF_3$ | 480.1 | <1e-8M |
| 2.218. | $C_2H_5$ | cyclobutyl | $CF_3$ | H | $CF_3$ | 557.1 | <1e-8M |
| 2.219. | $CH_3$ | cyclobutyl | $CF_3$ | H | $CF_3$ | 417.1 | <1e-8M |
| 2.220. | $CH_3$ | cyclobutyl | 3-furyl | H | Cl | 407.1 | <1e-8M |
| 2.221. | $CH_3$ | cyclobutyl | $CF_3$ | H | Cl | 409.1 | <1e-8M |
| 2.222. | $CH_3$ | $CH(CH_3)_2$ | Br | $OCH_3$ | H | 403.1 | <1e-8M |
| 2.223. | $CH_3$ | cyclobutyl | $3\text{-F}—C_6H_4$ | H | Cl | 435.1 | <1e-8M |
| 2.224. | $CH_3$ | cyclobutyl | $4\text{-F}—C_6H_4$ | H | Cl | 435.1 | <1e-8M |
| 2.225. | $CH_3$ | cyclobutyl | $4\text{-Cl}—C_6H_4$ | H | Cl | 452.1 | <1e-8M |
| 2.226. | $CH_3$ | cyclobutyl | $4\text{-OH}—C_6H_4$ | H | Cl | 433.1 | <1e-8M |
| 2.227. | $CH_3$ | cyclobutyl | $3\text{-Cl}—C_6H_4$ | H | Cl | 452.1 | <1e-8M |
| 2.228. | $CH_3$ | cyclopentyl | Cl | F | H | 373.1 | <1e-7M |
| 2.229. | $CH_2NH_2$ | $C_2H_5$ | $CF_3$ | H | H | 364.1 | |
| 2.230. | $CH_3$ | cyclohexyl | $CF_3$ | H | H | 403.1 | <1e-5M |
| 2.231. | OH | cyclobutyl | Cl | H | F | 361.1 | <1e-5M |
| 2.232. | $CH_3$ | cyclobutyl | Br | H | Br | 463.0 | <1e-8M |
| 2.233. | $CH_3$ | cyclobutyl | $CF_3$ | H | Br | 453.0 | <1e-8M |
| 2.234. | $CH_3$ | cyclobutyl | $O(3\text{-CF}_3—C_6H_4)$ | H | Cl | 501.1 | <1e-8M |
| 2.235. | $CH_3$ | cyclobutyl | $O(2\text{-F}—C_6H_4)$ | H | Cl | 451.1 | <1e-8M |
| 2.236. | $CH_3$ | cyclobutyl | $O(2\text{-Cl}—C_6H_4)$ | H | Cl | 468.1 | <1e-8M |
| 2.237. | $CH_3$ | cyclobutyl | $O(3\text{-Cl}—C_6H_4)$ | H | Cl | 468.1 | <1e-8M |
| 2.238. | $CH_3$ | cyclobutyl | $O(3\text{-OCH}_3—C_6H_4)$ | H | Cl | 463.1 | <1e-8M |
| 2.239. | $CH_3$ | cyclobutyl | $O(3\text{-CH}_3—C_6H_4)$ | H | Cl | 447.1 | <1e-7M |
| 2.240. | $CH_3$ | cyclobutyl | $O(4\text{-CH}_3—C_6H_4)$ | H | Cl | 447.1 | <1e-8M |
| 2.241. | $CH_3$ | cyclobutyl | Br | $OCH_3$ | Br | 494.0 | <1e-8M |
| 2.242. | $CH_3$ | cyclobutyl | Cl | F | Cl | 393.1 | <1e-8M |
| 2.243. | H | cyclohexyl | Cl | H | H | 369.1 | <1e-5M |
| 2.244. | H | cyclobutyl | Cl | H | Cl | 361.1 | <1e-8M |
| 2.245. | $CH_3$ | 1-F-cyclopropyl | Cl | Cl | H | 379.0 | <1e-8M |
| 2.246. | $CH_3$ | 1-F-cyclopropyl | $CF_3$ | H | $CF_3$ | 433.1 | <1e-8M |
| 2.247. | $CH_3$ | 1-F-cyclopropyl | $CF_3$ | H | $CF_3$ | 447.1 | <1e-8M |
| 2.248. | H | cyclobutyl | Br | H | Cl | 405.0 | <1e-8M |
| 2.249. | $CH_3$ | cyclobutyl | $3\text{-CF}_3—C_6H_4$ | H | Cl | 485.1 | <1e-8M |
| 2.250. | $CH_3$ | cyclobutyl | $4\text{-CF}_3—C_6H_4$ | H | Cl | 485.1 | <1e-8M |
| 2.251. | H | cyclobutyl | Br | H | Br | 449.0 | <1e-8M |
| 2.252. | H | cyclobutyl | $CF_3$ | H | Cl | 395.1 | <1e-8M |
| 2.253. | H | cyclobutyl | Cl | $OCH_3$ | H | 357.1 | <1e-8M |
| 2.254. | H | cyclopentyl | Cl | $OCH_3$ | H | 371.1 | <1e-5M |
| 2.255. | H | cyclobutyl | Br | $OCH_3$ | H | 401.1 | <1e-8M |
| 2.256. | H | cyclopentyl | Cl | H | Cl | 375.1 | <1e-5M |
| 2.257. | H | cyclohexyl | $CF_3$ | H | $CF_3$ | 557.1 | <1e-5M |
| 2.258. | $CH_3$ | cyclobutyl | CN | H | F | 350.1 | <1e-8M |
| 2.259. | H | cyclobutyl | $CF_3$ | H | Br | 439.0 | <1e-8M |
| 2.260. | $CH_3$ | 1-F-cyclopropyl | Cl | $OCH_3$ | H | 375.1 | <1e-8M |
| 2.261. | $CH_3$ | cyclohexyl | Cl | $OCH_3$ | H | 399.1 | |
| 2.262. | $CH_3$ | cyclohexyl | Cl | H | 2-furyl | 407.1 | <1e-8M |
| 2.263. | $CH_3$ | cyclobutyl | Cl | H | 2-thienyl | 423.1 | <1e-8M |
| 2.264. | $CH_3$ | cyclobutyl | $OCHF_2$ | H | H | 373.1 | <1e-8M |
| 2.265. | $CH_3$ | cyclobutyl | $OCF_3$ | F | H | 409.1 | <1e-8M |

TABLE 2-continued

| No | R¹ | R² | R⁴ | R⁵ | R⁶ | LCMS (M + H) | ED50 SHMT |
|---|---|---|---|---|---|---|---|
| 2.266. | CH₃ | cyclobutyl | OCF₃ | H | Cl | 425.1 | <1e−8M |
| 2.267. | CH₃ | 1-F-cyclopropyl | CF₃ | OCH₃ | H | 409.1 | <1e−8M |
| 2.268. | CH₃ | cyclobutyl | Cl | 1-pyirolidinyl | H | 410.1 | <1e−8M |
| 2.269. | CH₃ | cyclobutyl | CN | F | H | 350.1 | <1e−8M |
| 2.270. | CH₃ | 2,2-diF-cyclopropyl | Cl | H | Cl | 397.0 | <1e−8M |
| 2.271. | CH₃ | cyclobutyl | 4-morpholinyl | H | CF₃ | 460.1 | <1e−8M |
| 2.272. | CH₃ | cyclobutyl | CF₃ | CF₃ | H | 443.1 | <1e−8M |
| 2.273. | CH₃ | cyclobutyl | CF₃ | Cl | Cl | 443.1 | <1e−8M |
| 2.274. | H | cyclopropyl | 4-morpholinyl | H | CF₃ | 446.1 | <1e−8M |
| 2.275. | CH₃ | cyclopropyl | 3-thienyl | H | Cl | 409.1 | <1e−8M |
| 2.276. | CH₃ | cyclopropyl | 2-thienyl | H | Cl | 409.1 | <1e−6M |
| 2.277. | CH₃ | cyclobutyl | CHF₂ | H | H | 357.1 | <1e−8M |
| 2.278. | CH₃ | cyclobutyl | OCF₃ | H | H | 391.1 | <1e−8M |
| 2.279. | CH₃ | CH(CH₃)₂ | Cl | OCH₃ | H | 345.2 | <1e−8M |
| 2.280. | CH₃ | cyclobutyl | CN | H | Cl | 366.1 | <1e−8M |
| 2.281. | CH₃ | cyclobutyl | CN | H | Br | 410.0 | <1e−8M |
| 2.282. | CH₃ | cyclobutyl | CF₃ | H | CN | 400.1 | <1e−8M |
| 2.283. | CH₃ | cyclobutyl | CN | H | CN | 357.1 | <1e−7M |
| 2.284. | CH₃ | cyclobutyl | CONH₂ | H | Cl | 384.1 | <1e−8M |
| 2.285. | CH₃ | cyclobutyl | CN | H | Cl | 352.1 | <1e−8M |
| 2.286. | H | cyclobutyl | CN | H | CN | 343.2 | <1e−8M |
| 2.287. | H | CH(CH₃)₂ | Br | H | Br | 437.0 | <1e−8M |
| 2.288. | H | 1-F-cyclobutyl | Cl | H | Cl | 379.0 | <1e−7M |
| 2.289. | CH₃ | cyclobutyl | OCF₃ | Cl | H | 425.1 | <1e−8M |
| 2.290. | H | cyclobutyl | OCF₃ | Cl | H | 411.1 | <1e−7M |
| 2.291. | CH₃ | 4-cyclopentenyl | Cl | H | Cl | 388.1 | <1e−8M |
| 2.292. | CH₃ | cyclobutyl | Cl | OCH₃ | Cl | 405.1 | <1e−8M |
| 2.293. | H | cyclobutyl | Cl | OCH₃ | Cl | 391.1 | <1e−8M |
| 2.294. | CH₃ | cyclobutyl | CF₃ | H | Cl | 427.1 | <1e−8M |
| 2.295. | H | cyclobutyl | CF₃ | H | Cl | 413.1 | <1e−8M |
| 2.296. | CH₃ | cyclobutyl | OCF₃ | H | H | 407.1 | <1e−8M |
| 2.297. | H | cyclobutyl | SCF₃ | H | H | 393.1 | <1e−7M |
| 2.298. | H | cyclobutyl | Cl | H | I | 453.0 | <1e−8M |
| 2.299. | CH₃ | cyclobutyl | Cl | H | I | 467.0 | <1e−8M |
| 2.300. | CH₃ | 4-cyclopentenyl | Br | H | Br | 476.0 | <1e−8M |
| 2.301. | H | 4-cyclopentenyl | Br | H | Br | 461.0 | <1e−7M |
| 2.302. | H | cyclobutyl | CF₃ | CF₃ | H | 429.1 | <1e−8M |
| 2.303. | CH₃ | cyclobutyl | Cl | OCF₃ | H | 425.1 | <1e−8M |
| 2.304. | CH₃ | cyclobutyl | CF₃ | H | NO₂ | 420.1 | |
| 2.305. | CH₃ | cyclobutyl | CF₂CH₃ | H | H | 371.1 | <1e−7M |
| 2.306. | H | cyclobutyl | OCF₃ | H | H | 455.0 | <1e−8M |
| 2.307. | CH₃ | cyclobutyl | OCF₃ | H | Br | 469.0 | <1e−8M |
| 2.308. | CH₃ | cyclobutyl | I | H | I | 558.9 | <1e−8M |
| 2.309. | H | cyclobutyl | I | H | I | 544.9 | <1e−8M |
| 2.310. | CH₃ | cyclobutyl | SCH₃ | H | H | 353.1 | <1e−8M |
| 2.311. | H | cyclobutyl | SCH₃ | H | H | 339.2 | <1e−6M |
| 2.312. | CH₃ | cyclobutyl | SOCH₃ | H | H | 369.1 | <1e−6M |
| 2.313. | CH₃ | cyclobutyl | SO₂CH₃ | H | H | 385.1 | <1e−6M |
| 2.314. | CH₃ | CH₂CH₂C≡CH | Cl | H | Cl | 373.1 | <1e−7M |
| 2.315. | H | CH(CH₃)₂ | CF₃ | H | Cl | 383.1 | <1e−8M |
| 2.316. | CH₃ | CH(CH₃)₂ | CF₃ | H | Cl | 397.1 | <1e−8M |
| 2.317. | H | CH(CH₃)₂ | Cl | H | Br | 393.0 | <1e−8M |
| 2.318. | CH₃ | cyclobutyl | 2-pyridyl | H | Cl | 418.1 | <1e−8M |
| 2.319. | H | cyclobutyl | 2-thiazolyl | H | Cl | 410.1 | <1e−8M |
| 2.320. | CH₃ | cyclobutyl | 2-thiazolyl | H | Cl | 424.1 | <1e−8M |
| 2.321. | H | cyclobutyl | CF₃ | H | CN | 386.1 | <1e−8M |
| 2.322. | H | CH(CH₃)₂ | Br | OCH₃ | H | 389.1 | <1e−8M |
| 2.323. | CH₃ | cyclobutyl | C₆H₅ | H | CN | 408.1 | <1e−7M |
| 2.324. | CH₃ | cyclobutyl | 3-pyridyl | H | Cl | 418.1 | <1e−8M |
| 2.325. | CH₃ | cyclobutyl | 3-CF₃—C₆H₄ | H | CN | 476.1 | <1e−8M |
| 2.326. | CH₃ | cyclobutyl | 4-CF₃—C₆H₄ | H | CN | 476.1 | <1e−8M |
| 2.327. | CH₃ | cyclobutyl | 3-F—C₆H₄ | H | CN | 426.1 | <1e−8M |
| 2.328. | CH₃ | cyclobutyl | 4-F—C₆H₄ | H | CN | 426.1 | <1e−8M |
| 2.329. | CH₃ | cyclobutyl | 3-thienyl | H | CN | 414.1 | <1e−8M |
| 2.330. | H | CH(CH₃)₂ | Cl | OCH₃ | Cl | 379.1 | <1e−8M |
| 2.331. | CH₃ | CH(CH₃)₂ | Cl | OCH₃ | Cl | 393.1 | <1e−8M |
| 2.332. | CH₃ | cyclobutyl | 3-Cl—C₆H₄ | H | CN | 442.1 | <1e−8M |
| 2.333. | CH₃ | cyclobutyl | 4-Cl—C₆H₄ | H | CN | 442.1 | <1e−8M |
| 2.334. | CH₃ | CH(CH₃)₂ | Br | H | CN | 398.1 | <1e−8M |
| 2.335. | CH₃ | CH(CH₃)₂ | CN | H | CN | 345.2 | <1e−8M |
| 2.336. | H | CH(CH₃)₂ | CN | H | CN | 331.2 | <1e−8M |
| 2.337. | H | CH(CH₃)₂ | CF₃ | H | CN | 373.1 | <1e−8M |
| 2.338. | CH₃ | CH(CH₃)₂ | CF₃ | H | CN | 388.1 | <1e−8M |
| 2.339. | H | cyclobutyl | 4-thiazolyl | H | Cl | 410.1 | <1e−7M |
| 2.340. | CH₃ | cyclobutyl | 4-thiazolyl | H | Cl | 414.1 | <1e−8M |
| 2.341. | CH₃ | cyclobutyl | O-(4-Cl—C₆H₄) | H | Cl | 468.1 | <1e−8M |
| 2.342. | CH₃ | cyclopropyl | O-(4-Cl—C₆H₄) | H | Cl | 454.1 | <1e−8M |

TABLE 2-continued

| No | R¹ | R² | R⁴ | R⁵ | R⁶ | LCMS (M + H) | ED50 SHMT |
|---|---|---|---|---|---|---|---|
| 2.343. | H | cyclobutyl | O(4-OCH₃—C₆H₄) | H | Cl | 449.1 | <1e-8M |
| 2.344. | CH₃ | cyclobutyl | O-(4-OCH₃—C₆H₄) | H | Cl | 463.1 | <1e-8M |
| 2.345. | CH₃ | CH(CH₃)₂ | CN | H | Cl | 354.1 | <1e-8M |
| 2.346. | H | CH(CH₃)₂ | CN | H | Cl | 340.2 | |
| 2.347. | CH₃ | cyclopropyl | O-(3-Cl—C₆H₄) | H | Cl | 454.1 | <1e-8M |
| 2.348. | H | cyclobutyl | 2-pyridyl | H | CN | 395.2 | <1e-8M |
| 2.349. | CH₃ | cyclobutyl | 2-pyridyl | H | CN | 409.1 | |
| 2.350. | CH₃ | cyclobutyl | 3-pyridyl | H | CN | 409.1 | <1e-8M |
| 2.351. | H | cyclobutyl | 2-thiazolyl | H | CN | 401.1 | <1e-8M |
| 2.352. | H | cyclobutyl | 4-thiazolyl | H | CN | 401.1 | <1e-7M |
| 2.353. | CN | cyclobutyl | 4-thiazolyl | H | CN | 415.1 | <1e-8M |
| 2.354. | CH₃ | cyclobutyl | 5-tetrazolyl | H | 5-tetrazolyl | 443.1 | <1e-5M |
| 2.355. | CH₃ | cyclobutyl | CF₃ | H | 5-tetrazolyl | 443.1 | <1e-8M |
| 2.356. | CH₃ | cyclobutyl | O—CF₂CHF₂ | H | H | 423.1 | <1e-8M |
| 2.357. | CH₃ | cyclobutyl | 5-tetrazolyl | H | CN | 400.1 | <1e-7M |
| 2.358. | CH₃ | cyclobutyl | Br | H | I | 511.0 | <1e-8M |
| 2.359. | CH₃ | cyclopropyl | CN | H | Cl | 352.1 | <1e-8M |
| 2.360. | H | cyclopropyl | CN | H | Cl | 338.2 | <1e-7M |
| 2.361. | H | cyclopropyl | CF₃ | H | CN | 372.1 | <1e-7M |
| 2.362. | CH₃ | cyclopropyl | CF₃ | H | CN | 386.1 | <1e-8M |
| 2.363. | CH₃ | cyclobutyl | 3-(2-Cl-thienyl) | H | CN | 448.1 | <1e-8M |
| 2.364. | CH₃ | cyclobutyl | 3-(2-Cl-5-Cl-thienyl) | H | CN | 482.1 | <1e-8M |
| 2.365. | CH₃ | cyclopropyl | CN | H | Br | 396.0 | <1e-8M |
| 2.366. | CH₃ | cyclopropyl | CN | H | CN | 343.2 | <1e-8M |
| 2.367. | CH₃ | 4-cyclopentenyl | CF₃ | H | CN | 412.1 | <1e-8M |
| 2.368. | CH₃ | 4-cyclopentenyl | Cl | H | CN | 378.1 | <1e-8M |
| 2.369. | H | cyclobutyl | COOCH₂C₆H₅ | H | CN | 452.1 | <1e-8M |
| 2.370. | CH₃ | cyclobutyl | COOCH₂C₆H₅ | H | CN | 466.1 | <1e-8M |
| 2.371. | CH₃ | cyclobutyl | COOH | H | CN | 376.1 | <1e-6M |
| 2.372. | H | cyclobutyl | COOH | H | CN | 362.1 | <1e-5M |
| 2.373. | CH₃ | cyclobutyl | 1-pyrrolidinonyl | H | CF₃ | 458.1 | |
| 2.374. | CH₃ | 1-F-cyclopropyl | 1-pyrrolidinyl | H | Cl | 414.1 | |
| 2.375. | CH₃ | cyclobutyl | 1-azetidinonyl | H | CF₃ | 444.1 | |
| 2.376. | H | 4-cyclopentenyl | CN | H | Br | 408.0 | <1e-8M |
| 2.377. | CH₃ | 4-cyclopentenyl | CN | H | Br | 422.1 | <1e-8M |
| 2.378. | OCH₃ | CH(CH₃)₂ | Cl | H | Cl | 379.1 | <1e-8M |
| 2.379. | CH₃ | 1-F-cyclopropyl | CN | H | Cl | 414.0 | <1e-8M |
| 2.380. | H | 1-F-cyclopropyl | CN | H | Br | 400.0 | <1e-8M |
| 2.381. | CH₃ | cyclobutyl | Cl | H | COOCH2C₆H₅ | 475.1 | <1e-8M |
| 2.382. | CH₃ | cyclobutyl | COOH | H | Cl | 385.1 | <1e-7M |
| 2.383. | CH₃ | 1-F-cyclopropyl | CN | H | CN | 361.1 | <1e-8M |
| 2.384. | OC₂H₅ | CH(CH₃)₂ | Cl | H | Cl | 393.1 | <1e-8M |
| 2.385. | CH₃ | CF₂CH₂OH | CF₃ | H | CF₃ | 469.1 | |
| 2.386. | OCH₃ | cyclobutyl | Cl | H | Cl | 391.1 | <1e-8M |
| 2.387. | OC₂H₅ | cyclobutyl | Cl | H | Cl | 405.1 | <1e-7M |
| 2.388. | OCH₃ | cyclobutyl | CN | H | Br | 426.0 | <1e-8M |
| 2.389. | OC₂H₅ | cyclobutyl | CN | H | Br | 440.1 | <1e-8M |
| 2.390. | OCH₃ | cyclobutyl | CF₃ | H | CN | 416.1 | <1e-8M |
| 2.391. | OC₂H₅ | cyclobutyl | CF₃ | H | CN | 430.1 | <1e-7M |
| 2.392. | OCH₃ | cyclopropyl | CF₃ | H | CN | 402.1 | <1e-7M |
| 2.393. | OC₂H₅ | cyclopropyl | CF₃ | H | CN | 416.1 | <1e-6M |
| 2.394. | OCH₃ | 1-F-cyclopropyl | CN | H | Br | 430.0 | <1e-7M |
| 2.395. | OC₂H₅ | 1-F-cyclopropyl | CN | H | Br | 444.0 | <1e-6M |
| 2.396. | OCH₃ | cyclobutyl | CN | H | Br | 373.1 | <1e-8M |
| 2.397. | OC₂H₅ | cyclobutyl | CN | H | CN | 387.1 | <1e-7M |
| 2.398. | CH₃ | 4-cyclopentenyl | CN | H | CN | 369.2 | |
| 2.399. | CH₃ | cyclobutyl | 1-CH₃-tetrazol-4-yl | H | CF₃ | 457.1 | |
| 2.400. | CH₃ | 1-F-cyclopropyl | CN | H | Cl | 370.1 | |
| 2.401. | H | 1-F-cyclopropyl | CN | H | Cl | 356.1 | |
| 2.402. | OCH₃ | 1-F-cyclopropyl | CN | H | Cl | 386.1 | |
| 2.403. | CH₃ | cyclobutyl | 4-(1-CH₃-pyrazolyl) | H | CN | 412.1 | |
| 2.404. | CH₃ | 1-F-cyclopropyl | CF₃ | H | CN | 404.1 | |
| 2.405. | H | 1-F-cyclopropyl | CF₃ | H | CN | 390.1 | |
| 2.406. | OCH₃ | 1-F-cyclopropyl | CF₃ | H | CN | 419.1 | |
| 2.407. | CH₃ | cyclobutyl | 3-(2-Cl-thienyl) | H | Cl | 457.1 | |
| 2.408. | CH₃ | cyclobutyl | 3-(2-Cl-4-Cl-thienyl) | H | Cl | 493.0 | |
| 2.409. | CH₃ | cyclobutyl | CSNH₂ | H | CF₃ | 434.1 | |
| 2.410. | CH₃ | cyclobutyl | 5-(2-Cl-pyridyl) | H | Cl | 452.1 | |
| 2.411. | CH₃ | cyclobutyl | 1-pyrrolidinyl | H | CN | 401.1 | |
| 2.412. | H | cyclobutyl | 1-pyrrolidinyl | H | CN | 387.2 | |
| 2.413. | OCH₃ | cyclobutyl | 1-pyrrolidinyl | H | CN | 417.1 | |
| 2.414. | CH₃ | cyclobutyl | NCH₃COCH₃ | H | CN | 403.1 | |
| 2.415. | H | cyclobutyl | NCH₃COCH₃ | H | CN | 389.2 | |
| 2.416. | OCH₃ | cyclobutyl | NCH₃COCH₃ | H | CN | 419.1 | |
| 2.417. | CH₃ | cyclobutyl | OCF₃ | H | CN | 416.1 | |
| 2.418. | CH₃ | cyclobutyl | 1-pyrrolidinonyl | H | CN | 415.1 | |
| 2.419. | H | cyclobutyl | 1-pyrrolidinonyl | H | CN | 401.1 | |

TABLE 2-continued

| No | $R^1$ | $R^2$ | $R^4$ | $R^5$ | $R^6$ | LCMS (M + H) | ED50 SHMT |
|---|---|---|---|---|---|---|---|
| 2.420. | $OCH_3$ | cyclobutyl | 1-pyrrolidinonyl | H | CN | 431.1 | |
| 2.421. | $CH_3$ | cyclobutyl | 4-morpholinyl | H | CN | 417.1 | |
| 2.422. | H | cyclobutyl | 4-morpholinyl | H | CN | 403.1 | |
| 2.423. | $OCH_3$ | cyclobutyl | 4-morpholinyl | H | CN | 433.1 | |
| 2.424. | $OC_2H_5$ | cyclobutyl | 4-morpholinyl | H | CN | 447.1 | |
| 2.425. | $OCH_3$ | $CH(CH_3)_2$ | Cl | H | CN | 370.1 | |
| 2.426. | $OCH_3$ | $CH(CH_3)_2$ | CN | H | CN | 361.1 | |
| 2.427. | $OCH_3$ | $CH(CH_3)_2$ | $CF_3$ | H | CN | 404.1 | |
| 2.428. | $CH_3$ | cyclobutyl | Cl | OH | Cl | 391.1 | |
| 2.429. | $CH_3$ | cyclobutyl | Br | OH | Br | 479.0 | |
| 2.430. | $CH_2OH$ | cyclobutyl | Cl | H | Cl | 391.1 | |
| 2.431. | $CH_3$ | 1-F-cyclopropyl | 4-morpholinyl | H | Cl | 430.1 | |
| 2.432. | $CH_3$ | 1-F-cyclopropyl | 4-morpholinyl | H | $CF_3$ | 464.1 | |
| 2.433. | $CH_3$ | $CF_2CH_2OH$ | Cl | H | Cl | 401.0 | |
| 2.434. | $CH_3$ | 1-F-cyclopropyl | 1-pyrrolidinonyl | H | $CF_3$ | 462.1 | |
| 2.435. | $CH_3$ | 1-F-cyclopropyl | 1-pyrrolidinyl | H | $CF_3$ | 448.1 | |
| 2.436. | $CH_3$ | 1-F-cyclopropyl | 1-azetidinonyl | H | $CF_3$ | 448.1 | |
| 2.437. | $CH_3$ | 1-F-cyclopropyl | $N(CH_3)_2$ | H | $CF_3$ | 422.1 | |
| 2.438. | $OCH_3$ | 1-F-cyclopropyl | $CF_3$ | H | $CF_3$ | 463.1 | |
| 2.439. | $CH_3$ | 1-F-cyclopropyl | $NCH_3COCH_3$ | H | $CF_3$ | 450.1 | |
| 2.440. | $CH_3$ | 1-F-cyclopropyl | $N(CH_3)_2$ | H | Cl | 388.1 | |
| 2.441. | $CH_3$ | cyclobutyl | 3-isoxazolinyl | H | $CF_3$ | 444.1 | |
| 2.442. | $CH_3$ | cyclobutyl | 3-isoxazolinyl | H | Cl | 410.1 | |
| 2.443. | $CH_3$ | cyclobutyl | $OCH_2CN$ | H | Cl | 396.1 | <1e-8M |
| 2.444. | $OCH_3$ | cyclobutyl | $OCH_2CN$ | H | Cl | 412.1 | <1e-7M |
| 2.445. | $CH_3$ | cyclobutyl | $OCH_2OCH_3$ | H | Cl | 401.1 | <1e-8M |
| 2.446. | $CH_3$ | cyclobutyl | $OCH_2$(5-tetrazolyl) | H | Cl | 439.1 | <1e-8M |
| 2.447. | $CH_3$ | cyclobutyl | F | $OCH_3$ | F | 373.1 | <1e-8M |
| 2.448. | $CH_3$ | 1-F-cyclopropyl | F | $OCH_3$ | F | 377.1 | <1e-6M |
| 2.449. | $CH_3$ | cyclobutyl | F | OH | F | 359.1 | <1e-7M |
| 2.450. | $CH_3$ | 1-F-cyclopropyl | F | OH | F | 363.1 | |
| 2.451. | $CH_3$ | 1-F-cyclopropyl | $NCH_3COCH_3$ | H | CN | 407.1 | <1e-8M |
| 2.452. | $CH_3$ | 1-F-cyclopropyl | 1-pyrrolidinonyl | H | CN | 419.1 | <1e-6M |
| 2.453. | $CH_3$ | cyclobutyl | $3\text{-}COOCH_3\text{---}C_6H_4$ | H | CN | 466.1 | <1e-8M |
| 2.454. | $OCH_3$ | cyclobutyl | $4\text{-}COOCH_3\text{---}C_6H_4$ | H | CN | 482.1 | <1e-6M |
| 2.455. | $CH_3$ | cyclobutyl | $4\text{-}COOCH_3\text{---}C_6H_4$ | H | CN | 466.1 | <1e-7M |
| 2.456. | $CH_3$ | cyclobutyl | $3\text{-}COOCH_3\text{---}C_6H_4$ | H | Cl | 475.1 | <1e-8M |
| 2.457. | $OCH_3$ | cyclobutyl | $3\text{-}COOCH_3\text{---}C_6H_4$ | H | Cl | 491.1 | <1e-8M |
| 2.458. | $CH_3$ | cyclobutyl | $4\text{-}COOCH_3\text{---}C_6H_4$ | H | Cl | 475.1 | <1e-7M |
| 2.459. | $CH_3$ | cyclobutyl | $3\text{-}CF_3\text{-}4\text{-}OH\text{---}C_6H_3$ | H | CN | 492.1 | <1e-8M |
| 2.460. | $CH_3$ | cyclobutyl | $4\text{-}COOH\text{---}C_6H_4$ | H | CN | 452.1 | <1e-8M |
| 2.461. | $CH_3$ | cyclobutyl | $3\text{-}COOH\text{---}C_6H_4$ | H | CN | 452.1 | <1e-8M |
| 2.462. | $CH_3$ | cyclobutyl | $2\text{-}COOCH_3\text{---}C_6H_4$ | H | CN | 466.1 | |
| 2.463. | $CH_3$ | cyclobutyl | $3\text{-}F\text{-}4\text{-}OCH_3\text{-}5\text{-}F\text{---}C_6H_2$ | H | CN | 474.1 | <1e-8M |
| 2.464. | $CH_3$ | cyclobutyl | CN | $OCH_3$ | H | 362.2 | <1e-8M |
| 2.465. | $CH_2OH$ | 1-F-cyclopropyl | $CF_3$ | H | $CF_3$ | 463.1 | <1e-7M |
| 2.466. | $CH_3$ | $C_2H_5$ | Br | $CH_3$ | H | 373.1 | <1e-7M |
| 2.467. | $CH_3$ | $C_2H_5$ | Br | H | F | 376.0 | <1e-7M |
| 2.468. | $CH_3$ | $C_2H_5$ | Br | H | Cl | 393.0 | <1e-8M |
| 2.469. | $CH_3$ | $C_2H_5$ | $CH_3$ | H | Br | 373.1 | <1e-8M |
| 2.470. | $CH_3$ | cyclobutyl | $OCH_2CN$ | H | $CF_3$ | 430.1 | <1e-7M |
| 2.471. | $CH_3$ | cyclobutyl | $OCH_2CN$ | H | CN | 387.1 | <1e-8M |
| 2.472. | $CH_3$ | $C_2H_5$ | Cl | Br | H | 393.0 | <1e-7M |
| 2.473. | $CH_3$ | $C_2H_5$ | Br | $CH_3$ | Br | 451.0 | <1e-8M |
| 2.474. | $CH_3$ | cyclobutyl | $OCH_2$(5-tetrazolyl) | H | $CF_3$ | 473.2 | <1e-8M |
| 2.475. | $CH_3$ | cyclobutyl | $OCH_2$(5-tetrazolyl) | H | CN | 430.1 | <1e-8M |
| 2.476. | $CH_3$ | cyclobutyl | $OCH_2OCH_3$ | H | $CF_3$ | 435.1 | <1e-8M |
| 2.477. | $CH_3$ | cyclobutyl | $OCH_2OCH_3$ | H | CN | 392.1 | <1e-8M |
| 2.478. | $CH_3$ | 1-F-3-oxetanyl | Cl | H | Cl | 395.0 | <1e-7M |
| 2.479. | $CH_3$ | 1-F-cyclopropyl | $OCH_2COOC_2H_5$ | H | Br | 491.1 | <1e-7M |
| 2.480. | $CH_3$ | cyclobutyl | $OCH_2COOC_2H_5$ | H | Cl | 443.1 | <1e-7M |
| 2.481. | $CH_3$ | cyclobutyl | $O(2\text{-}NO_2\text{-}4\text{-}OH\text{---}C_6H_3)$ | H | Cl | 494.1 | <1e-8M |
| 2.482. | $CH_3$ | cyclobutyl | $3\text{-}COOH\text{---}C_6H_4$ | H | Cl | 461.1 | <1e-8M |
| 2.483. | $CH_3$ | cyclobutyl | $4\text{-}COOH\text{---}C_6H_4$ | H | Cl | 461.1 | <1e-8M |
| 2.484. | $CH_3$ | cyclobutyl | $3\text{-}F\text{-}4\text{-}OH\text{-}5\text{-}F\text{---}C_6H_2$ | H | CN | 460.1 | <1e-8M |
| 2.485. | $CH_3$ | cyclobutyl | Cl | OH | H | 357.1 | <1e-8M |
| 2.486. | $CH_3$ | cyclobutyl | CN | $OCH_3$ | CN | 387.1 | <1e-8M |
| 2.487. | $CH_3$ | cyclobutyl | CN | $OCH_3$ | Cl | 396.1 | <1e-8M |
| 2.488. | $CH_3$ | cyclobutyl | 4-morpholinyl | H | Cl | 426.1 | <1e-8M |
| 2.489. | $CH_3$ | cyclobutyl | $4\text{-}CN\text{---}C_6H_4$ | H | Cl | 442.1 | |
| 2.490. | $CH_3$ | cyclobutyl | $NHSO_2C_6H_5$ | H | Cl | 496.1 | <1e-8M |
| 2.491. | $CH_3$ | cyclobutyl | $CF_3$ | $OCH_3$ | CN | 430.1 | <1e-8M |
| 2.492. | $CH_3$ | cyclobutyl | Br | $OCH_3$ | CN | 440.1 | <1e-8M |
| 2.493. | $CH_3$ | cyclobutyl | 4-(5-tetrazolyl)-$C_6H_4$ | H | Cl | 485.1 | <1e-8M |
| 2.494. | $CH_3$ | cyclobutyl | $3\text{-}COOH\text{---}C_6H_4$ | H | H | 427.1 | <1e-7M |
| 2.495. | $CH_3$ | cyclobutyl | $4\text{-}COOH\text{---}C_6H_4$ | H | H | 427.1 | <1e-8M |
| 2.496. | $CH_3$ | 1-F-3-oxetanyl | Cl | H | Cl | 391.1 | <1e-7M |

TABLE 2-continued

| No | $R^1$ | $R^2$ | $R^4$ | $R^5$ | $R^6$ | LCMS (M + H) | ED50 SHMT |
|---|---|---|---|---|---|---|---|
| 2.497. | $CH_3$ | 1-F-cyclopropyl | $CH_2CH_2COOH$ | H | Cl | 417.1 | <1e-7M |
| 2.498. | $CH_3$ | 1-F-cyclopropyl | $CH_2COOH$ | H | Cl | 403.1 | <1e-7M |
| 2.499. | $CH_3$ | cyclobutyl | $CH_2COOH$ | H | Cl | 399.1 | <1e-8M |
| 2.500. | $CH_3$ | cyclobutyl | $CH_2CH_2COOH$ | H | Cl | 413.1 | <1e-8M |
| 2.501. | $CH_3$ | 1-F-3-oxetanyl | $CF_3$ | H | $CF_3$ | 463.1 | <1e-8M |
| 2.502. | $CH_3$ | 1-F-3-oxetanyl | $CF_3$ | H | Cl | 429.1 | <1e-8M |
| 2.503. | $CH_3$ | 1-F-cyclopropyl | $OCH_2COOH$ | H | Br | 463.0 | <1e-5M |
| 2.504. | $CH_3$ | cyclobutyl | Cl | $OCH_2COOH$ | Cl | 449.1 | <1e-6M |
| 2.505. | $CH_3$ | cyclobutyl | $OCH_2CH_2COOH$ | H | Cl | 429.1 | <1e-8M |
| 2.506. | $CH_3$ | cyclobutyl | $OCH_2COOH$ | H | Cl | 415.1 | <1e-8M |
| 2.507. | $CH_3$ | cyclobutyl | $OCH_2COOH$ | H | Br | 459.1 | <1e-5M |
| 2.508. | $CH_3$ | cyclobutyl | OH | H | Cl | 357.1 | <1e-5M |
| 2.509. | $CH_3$ | cyclobutyl | 3-$COOCH_3$-4-Cl—$C_6H_3$ | H | CN | 500.2 | <1e-8M |
| 2.510. | $CH_3$ | 1-F-cyclopropyl | 3-COOH—$C_6H_4$ | H | CN | 456.1 | <1e-8M |
| 2.511. | $CH_3$ | 1-F-cyclopropyl | 3-COOH—$C_6H_4$ | H | CN | 456.1 | <1e-8M |
| 2.512. | $CH_3$ | cyclobutyl | 3-CN—$C_6H_4$ | H | Cl | 442.1 | <1e-8M |
| 2.513. | $CH_3$ | cyclobutyl | 3-$COOCH_3$-5-F—$C_6H_3$ | H | CN | 484.1 | <1e-8M |
| 2.514. | $CH_3$ | cyclobutyl | 3-$COOCH_3$-4-Cl—$C_6H_3$ | H | Cl | 510.2 | <1e-8M |
| 2.515. | $CH_3$ | cyclobutyl | 3-(5-tetrazolinyl)-$C_6H_4$ | H | Cl | 485.1 | <1e-8M |
| 2.516. | $CH_3$ | cyclobutyl | 3-$COOCH_3$-4-F—$C_6H_3$ | H | CN | 584.1 | <1e-8M |
| 2.517. | $CH_3$ | cyclobutyl | 3-$COOCH_3$-5-Cl—$C_6H_3$ | H | CN | 500.2 | <1e-8M |
| 2.518. | $CH_3$ | $CH(CH_3)_2$ | 3-COOH—$C_6H_4$ | H | CN | 449.1 | <1e-8M |
| 2.519. | $CH_3$ | $CH(CH_3)_2$ | 4-COOH—$C_6H_4$ | H | CN | 440.1 | <1e-8M |
| 2.520. | $C_2H_5$ | $CH(CH_3)_2$ | CN | H | CN | 359.2 | <1e-8M |
| 2.521. | $CH_3$ | cyclobutyl | 3-F-4-$COOCH_3$—$C_6H_3$ | H | CN | 483.1 | <1e-8M |
| 2.522. | $CH_3$ | cyclobutyl | 3-$OCH_3$-4-$COOCH_3$—$C_6H_3$ | H | CN | 496.2 | <1e-8M |
| 2.523. | $CH_3$ | cyclobutyl | 3-$CH_2CH_2COOCH_3$—$C_6H_4$ | H | CN | 494.1 | <1e-8M |
| 2.524. | $CH_3$ | cyclobutyl | 3-$CH_2COOCH_3$—$C_6H_4$ | H | CN | 480.1 | <1e-8M |
| 2.525. | $CH_3$ | cyclobutyl | 3-$CH_2CH_2COOCH_3$—$C_6H_4$ | H | CN | 494.1 | <1e-8M |
| 2.526. | $CH_3$ | cyclobutyl | 4-$CH_2COOCH_3$—$C_6H_4$ | H | CN | 480.1 | <1e-8M |
| 2.527. | $CH_3$ | cyclobutyl | 3-$NHSO_2CH_3$—$C_6H_4$ | H | Cl | 511.1 | <1e-8M |
| 2.528. | $CH_3$ | cyclobutyl | 4-$NHSO_2CH_3$—$C_6H_4$ | H | Cl | 511.1 | <1e-8M |
| 2.529. | $CH_3$ | $C_2H_5$ | CN | H | Cl | 340.2 | <1e-8M |
| 2.530. | $CH_3$ | $C_2H_5$ | CN | H | $CF_3$ | 373.1 | <1e-8M |
| 2.531. | $CH_3$ | $C_3H_7$ | $CF_3$ | H | CN | 388.1 | <1e-8M |
| 2.532. | $CH_3$ | $C_2H_5$ | Br | H | CN | 384.0 | <1e-8M |
| 2.533. | $CH_3$ | $C_3H_7$ | CN | H | Cl | 354.1 | <1e-8M |
| 2.534. | $CH_3$ | $C_3H_7$ | CN | H | Br | 398.1 | <1e-8M |
| 2.535. | $CH_3$ | $C_3H_7$ | CN | H | CN | 345.2 | <1e-8M |
| 2.536. | $CH_3$ | cyclobutyl | 4-$OCH_2COOC_2H_5$—$C_6H_4$ | H | CN | 510.2 | <1e-8M |
| 2.537. | $CH_3$ | cyclobutyl | 3-$OCH_2COOC_2H_5$—$C_6H_4$ | H | H | 510.2 | <1e-8M |
| 2.538. | $CH_3$ | cyclobutyl | 4-$OCH_2COOH$—$C_6H_4$ | H | CN | 482.1 | <1e-8M |
| 2.539. | $CH_3$ | cyclobutyl | $CH_2CH_2$(5-tetrazolyl) | H | Cl | 437.1 | <1e-8M |
| 2.540. | $CH_3$ | 4-OH-cyclobutyl | $CF_3$ | H | $CF_3$ | 459.1 | <1e-7M |
| 2.541. | $CH_3$ | cyclobutyl | CN | $CH_2COOH$ | H | 389.2 | <1e-6M |
| 2.542. | $CH_3$ | cyclobutyl | Cl | $CH_2CH_2COOH$ | H | 413.1 | <1e-7M |
| 2.543. | $CH_3$ | cyclobutyl | $CF_3$ | $CH_2CH_2COOH$ | H | 447.1 | <1e-7M |
| 2.544. | $CH_3$ | cyclobutyl | $CF_3$ | $CH_2COOH$ | H | 433.1 | <1e-7M |
| 2.545. | $CH_3$ | cyclobutyl | 3-COOH-5-F—$C_6H_3$ | H | CN | 470.1 | <1e-8M |
| 2.546. | $CH_3$ | cyclobutyl | 4-$COOCH_3$-3-Cl—$C_6H_3$ | H | CN | 500.2 | <1e-7M |
| 2.547. | $CH_3$ | cyclobutyl | 3-$CF_3$-4-$OCH_3$—$C_6H_3$ | H | CN | 506.2 | <1e-8M |
| 2.548. | $CH_3$ | cyclobutyl | 3-$COOCH_3$-5-$OCH_3$—$C_6H_3$ | H | CN | 496.2 | <1e-8M |
| 2.549. | $CH_3$ | cyclobutyl | 3-$COOCH_3$-5-$COOCH_3$—$C_6H_3$ | H | CN | 524.2 | <1e-7M |
| 2.550. | $CH_3$ | cyclobutyl | 3-$COOCH_3$-4-$COOCH_3$—$C_6H_3$ | H | CN | 524.2 | <1e-8M |
| 2.551. | $CH_3$ | cyclobutyl | 3-$COOCH_3$-5-$OCF_3$—$C_6H_3$ | H | CN | 550.2 | <1e-7M |
| 2.552. | $CH_3$ | cyclobutyl | 3-$COOCH_3$-5-CF—$C_6H_3$ | H | CN | 534.2 | <1e-8M |
| 2.553. | $CH_3$ | $CH(CH_3)_2$ | $NCH_3COCH_3$ | H | CN | 391.1 | <1e-8M |
| 2.554. | $CH_3$ | cyclobutyl | 3-$NO_2$-5-$COOCH_3$—$C_6H_3$ | H | CN | 511.1 | <1e-8M |
| 2.555. | $CH_3$ | cyclobutyl | $CH_2CH_2CN$ | H | Cl | 394.1 | <1e-8M |
| 2.556. | $CH_3$ | cyclobutyl | 3-COOH-4-Cl—$C_6H_3$ | H | CN | 486.1 | <1e-8M |
| 2.557. | $CH_3$ | cyclobutyl | 3-COOH-4-Cl—$C_6H_3$ | H | Cl | 495.1 | <1e-8M |
| 2.558. | $CH_3$ | cyclobutyl | 3-COOH-4-F—$C_6H_3$ | H | CN | 470.1 | <1e-8M |
| 2.559. | $CH_3$ | cyclobutyl | 3-COOH-5-Cl—$C_6H_3$ | H | CN | 486.1 | <1e-7M |
| 2.560. | $CH_3$ | cyclobutyl | 4-COOH-3-F—$C_6H_3$ | H | CN | 470.1 | <1e-8M |
| 2.561. | $CH_3$ | cyclobutyl | 3-$OCH_3$-4-COOH—$C_6H_3$ | H | CN | 482.1 | <1e-8M |
| 2.562. | $CH_3$ | cyclobutyl | 3-Cl-4-COOH—$C_6H_3$ | H | CN | 486.1 | <1e-8M |
| 2.563. | $CH_3$ | cyclobutyl | 3-$OCH_3$-5-COOH—$C_6H_3$ | H | CN | 482.1 | <1e-8M |
| 2.564. | $CH_3$ | cyclobutyl | 3-COOH-5-COOH—$C_6H_3$ | H | CN | 496.2 | <1e-6M |
| 2.565. | $CH_3$ | cyclobutyl | 3-COOH-4-COOH—$C_6H_3$ | H | CN | 496.2 | <1e-8M |
| 2.566. | $CH_3$ | cyclobutyl | 3-$NO_2$-5-COOH—$C_6H_3$ | H | CN | 497.2 | <1e-8M |
| 2.567. | $CH_3$ | cyclobutyl | Cl | OH | CN | 382.1 | <1e-7M |
| 2.568. | $CH_3$ | cyclobutyl | $CH_2CN$ | H | Cl | 380.1 | <1e-8M |
| 2.569. | $CH_3$ | 1-F-cyclobutyl | CN | H | CN | 375.1 | <1e-7M |
| 2.570. | $CH_3$ | cyclobutyl | $CH_2$(5-tetrazolyl) | H | Cl | 423.1 | <1e-8M |
| 2.571. | $CH_3$ | cyclobutyl | 3-$COOCH_3$-5-COOH—$C_6H_3$ | H | CN | 510.2 | <1e-7M |
| 2.572. | $CH_3$ | cyclobutyl | 3-$COOCH_3$-4-COOH—$C_6H_3$ | H | CN | 510.2 | <1e-7M |
| 2.573. | $C_2H_5$ | $C_2H_5$ | Cl | H | CN | 354.1 | <1e-7M |

TABLE 2-continued

| No | R¹ | R² | R⁴ | R⁵ | R⁶ | LCMS (M + H) | ED50 SHMT |
|---|---|---|---|---|---|---|---|
| 2.574. | $C_2H_5$ | $C_2H_5$ | $CF_3$ | H | CN | 388.1 | <1e-8M |
| 2.575. | $C_2H_5$ | $C_3H_7$ | $CF_3$ | H | CN | 402.1 | <1e-8M |
| 2.576. | $C_2H_5$ | $C_2H_5$ | CN | H | Br | 398.1 | <1e-7M |
| 2.577. | $C_2H_5$ | $C_3H_7$ | CN | H | Cl | 368.1 | <1e-7M |
| 2.578. | $C_2H_5$ | $C_3H_7$ | CN | H | Br | 412.1 | <1e-7M |
| 2.579. | $C_2H_5$ | $C_3H_7$ | CN | H | CN | 359.2 | <1e-7M |
| 2.580. | $CH(CH_3)_2$ | $C_2H_5$ | Cl | H | CN | 368.1 | <1e-7M |
| 2.581. | $CH(CH_3)_2$ | $C_2H_5$ | $CF_3$ | H | CN | 402.1 | <1e-7M |
| 2.582. | $CH(CH_3)_2$ | $C_3H_7$ | $CF_3$ | H | CN | 416.1 | <1e-8M |
| 2.583. | $CH(CH_3)_2$ | $C_2H_5$ | Br | H | CN | 412.1 | <1e-7M |
| 2.584. | $CH(CH_3)_2$ | $C_3H_7$ | Cl | H | CN | 382.1 | <1e-8M |
| 2.585. | $CH(CH_3)_2$ | $C_3H_7$ | Br | H | CN | 426.1 | <1e-7M |
| 2.586. | $CH(CH_3)_2$ | $C_3H_7$ | CN | H | CN | 373.2 | <1e-6M |
| 2.587. | $CH_2OCH_3$ | $C_2H_5$ | Cl | H | CN | 370.1 | <1e-6M |
| 2.588. | $CH_2OCH_3$ | $C_2H_5$ | $CF_3$ | H | CN | 404.1 | <1e-7M |
| 2.589. | $CH_2OCH_3$ | $C_3H_7$ | $CF_3$ | H | CN | 418.1 | <1e-7M |
| 2.590. | $CH_2OCH_3$ | $C_2H_5$ | Br | H | CN | 414.0 | <1e-6M |
| 2.591. | $CH_2OCH_3$ | $C_3H_7$ | Cl | H | CN | 384.1 | <1e-5M |
| 2.592. | $CH_2OCH_3$ | $C_3H_7$ | Br | H | CN | 428.1 | <1e-6M |
| 2.593. | $CH_2OCH_3$ | $C_3H_7$ | CN | H | CN | 375.1 | <1e-5M |
| 2.594. | $CH_3$ | cyclobutyl | Cl | COOH | H | 385.1 | <1e-6M |
| 2.595. | $CH_3$ | cyclobutyl | $4\text{-}NHSO_2CF_3\text{—}C_6H_5$ | H | Cl | 564.1 | <1e-8M |
| 2.596. | $CH_3$ | cyclobutyl | $O\text{-}(3\text{-}F\text{-}4\text{-}OH\text{-}5\text{-}F\text{—}C_6H_2)$ | H | Cl | 485.1 | <1e-7M |
| 2.597. | $CH_3$ | cyclobutyl | $O\text{-}(3\text{-}CF_3\text{-}4\text{-}OH\text{—}C_6H_3)$ | H | Cl | 517.1 | <1e-7M |
| 2.598. | $OCH_3$ | $C_2H_5$ | Cl | H | CN | 356.1 | <1e-6M |
| 2.599. | $OCH_3$ | $C_2H_5$ | $CF_3$ | H | CN | 390.1 | <1e-6M |
| 2.600. | $OCH_3$ | $C_3H_7$ | $CF_3$ | H | CN | 404.1 | <1e-6M |
| 2.601. | $OCH_3$ | $C_2H_5$ | Br | H | CN | 400.0 | <1e-6M |
| 2.602. | $OCH_3$ | $C_3H_7$ | Cl | H | CN | 370.1 | <1e-5M |
| 2.603. | $OCH_3$ | $C_3H_7$ | Br | H | CN | 414.0 | <1e-6M |
| 2.604. | $OCH_3$ | $C_3H_7$ | CN | H | CN | 361.1 | <1e-6M |
| 2.605. | $CHF_2$ | $C_2H_5$ | Cl | H | CN | 376.1 | <1e-8M |
| 2.606. | $CHF_2$ | $C_2H_5$ | $CF_3$ | H | CN | 410.1 | <1e-8M |
| 2.607. | $CHF_2$ | $C_2H_5$ | Br | H | CN | 420.0 | <1e-8M |
| 2.608. | $CHF_2$ | $C_3H_7$ | Cl | H | CN | 390.1 | <1e-8M |
| 2.609. | $CHF_2$ | $C_3H_7$ | Br | H | CN | 434.0 | <1e-7M |
| 2.610. | $CHF_2$ | $C_3H_7$ | CN | H | CN | 381.1 | <1e-7M |
| 2.611. | $CH_3$ | cyclobutyl | $NCH_3COC_2H_5$ | H | CN | 417.1 | <1e-8M |
| 2.612. | $CH_3$ | cyclobutyl | $NCH_3COC_3H_7$ | H | CN | 431.1 | <1e-8M |
| 2.613. | $CH_3$ | cyclobutyl | $NCH_3COCH(CH_3)_2$ | H | CN | 431.1 | <1e-8M |
| 2.614. | $CH_3$ | cyclobutyl | $NCH_3COC_4H_9$ | H | CN | 445.1 | <1e-8M |
| 2.615. | $CH_3$ | cyclobutyl | $NCH_3COCH_2OCH_3$ | H | CN | 433.1 | <1e-8M |
| 2.616. | $CH_3$ | cyclobutyl | $NCH_3COCH_2OCH_2CH_2OCH_3$ | H | CN | 477.1 | <1e-8M |
| 2.617. | $CH_3$ | cyclobutyl | $NCH_3SO_2CH_3$ | H | CN | 439.1 | <1e-8M |
| 2.618. | $CH_3$ | cyclobutyl | $CH_2CH_2COOH$ | H | CN | 404.1 | |
| 2.619. | $CH_3$ | $CH(CH_3)_2$ | Cl | OH | Cl | 379.1 | |
| 2.620. | $CH_3$ | $CF(CH_3)_2$ | Cl | $OCH_3$ | H | 377.1 | <1e-8M |
| 2.621. | $CH_3$ | cyclobutyl | Cl | $CH_2CH_2CN$ | H | 394.1 | |
| 2.622. | $CH_3$ | cyclobutyl | Cl | $OCH_2CN$ | H | 396.1 | |
| 2.623. | $CH_3$ | cyclobutyl | 2-(5-$COOCH_3$)-thienyl | H | CN | 472.1 | |
| 2.624. | $CH_3$ | cyclobutyl | Cl | $CH_2CN$ | H | 380.1 | |
| 2.625. | $CH_3$ | cyclobutyl | $OCH_2COOH$ | H | CN | 406.1 | <1e-7M |
| 2.626. | $CH_3$ | cyclobutyl | OH | H | CN | 348.1 | <1e-7M |
| 2.627. | $CH_3$ | cyclobutyl | $CH_2COOH$ | H | CN | 389.2 | <1e-7M |
| 2.628. | $CH_3$ | cyclobutyl | $NCH_3COCH_3$ | H | $NCH_3COCH_3$ | 453.1 | <1e-8M |
| 2.629. | $CH_3$ | cyclobutyl | $NCH_3CH_2CN$ | H | CN | 414.1 | <1e-8M |
| 2.630. | $CH_3$ | cyclobutyl | 2-imidazolinonyl | H | CN | 416.1 | |
| 2.631. | $CH_3$ | cyclobutyl | $NCH_3CH_2CN$ | H | CN | 400.1 | <1e-8M |
| 2.632. | $CH_3$ | cyclobutyl | $NCH_3COCH_2CH_2COOH$ | H | CN | 461.1 | <1e-8M |
| 2.633. | $CH_3$ | cyclobutyl | $NCH_3CO(3\text{-}COOH\text{—}C_6H_4)$ | H | CN | 509.2 | <1e-7M |
| 2.634. | $CH_3$ | cyclobutyl | $NCH_3CO(4\text{-}COOH\text{—}C_6H_4)$ | H | CN | 509.2 | <1e-7M |
| 2.635. | $CH_3$ | cyclobutyl | $NCH_3COCH_2CN$ | H | CN | 428.1 | <1e-8M |
| 2.636. | $CH_3$ | cyclobutyl | $NCH_3COCH_2CH_2CH_2COOH$ | H | CN | 475.1 | <1e-8M |
| 2.637. | $CH_3$ | cyclobutyl | Cl | $CH_2CH_2\text{(5-tetrazolyl)}$ | H | 437.1 | <1e-8M |
| 2.638. | $CH_3$ | cyclobutyl | Cl | $OCH_2\text{(5-tetrazolyl)}$ | H | 439.1 | <1e-8M |
| 2.639. | $CH_3$ | cyclobutyl | Cl | $CH_2\text{(5-tetrazolyl)}$ | H | 423.1 | <1e-8M |
| 2.640. | $CH_3$ | cyclobutyl | 2-(5-COOH-thienyl) | H | CN | 458.1 | <1e-8M |
| 2.641. | $CH_3$ | cyclobutyl | 2-(5-$COOCH_3$-furanyl) | H | CN | 456.1 | |
| 2.642. | $CH_3$ | cyclobutyl | 2-(5-COOH-furanyl) | H | CN | 442.1 | |
| 2.643. | $CH_3$ | cyclobutyl | $3\text{-}OCF_3\text{-}5\text{-}COOH\text{—}C_6H_3$ | H | CN | 536.2 | <1e-8M |
| 2.644. | $CH_3$ | cyclobutyl | $3\text{-}CF_3\text{-}5\text{-}COOH\text{—}C_6H_3$ | H | CN | 520.2 | <1e-8M |
| 2.645. | $CH_3$ | cyclobutyl | Cl | $OCH_2CH_2CN$ | H | 410.1 | <1e-8M |
| 2.646. | $CH_3$ | cyclobutyl | Cl | $OCH_2CH_2\text{(5-tetrazolyl)}$ | H | 453.1 | <1e-8M |
| 2.647. | $CH_3$ | cyclobutyl | CN | $CH_2CH_2CN$ | H | 385.2 | <1e-8M |
| 2.648. | $CH_3$ | cyclobutyl | CN | $CH_2CH_2\text{(5-tetrazolyl)}$ | H | 418.1 | <1e-8M |
| 2.649. | $CH_3$ | cyclobutyl | $CH_2NHCOCH_2COOH$ | H | $CF_3$ | 504.2 | <1e-8M |
| 2.650. | $CH_3$ | cyclobutyl | $CH_2CH_2CN$ | H | CN | 385.2 | <1e-8M |

TABLE 2-continued

| No | R¹ | R² | R⁴ | R⁵ | R⁶ | LCMS (M + H) | ED50 SHMT |
|---|---|---|---|---|---|---|---|
| 2.651. | $CH_3$ | $CHFCH_3$ | Cl | H | Cl | 367.0 | <1e-8M |
| 2.652. | $CH_3$ | 3,3-diF-cyclobutyl | Cl | H | Cl | 411.1 | <1e-8M |
| 2.653. | $CH_3$ | $CF_2CH_3$ | Cl | H | Cl | 384.0 | <1e-7M |
| 2.654. | $CH_3$ | cyclobutyl | 5-tetrazolyl | $CH_2CH_2$(5-tetrazolyl) | H | 470.2 | <1e-7M |
| 2.655. | $CH_3$ | cyclobutyl | $CH_2CH_2$($_5$-tetrazolyl) | H | 5-tetrazolyl | 470.2 | <1e-5M |
| 2.656. | $CH_3$ | 1-F-3-oxetanyl | 3-COOH—$C_6H_4$ | H | CN | 472.1 | <1e-8M |
| 2.657. | $CH_3$ | 1-F-3-oxetanyl | H | H | CN | 472.1 | <1e-6M |
| 2.658. | $CH_3$ | cyclobutyl | $NCH_3CH_2CH_2CH_2COOC_2H_5$ | H | CN | 475.1 | <1e-8M |
| 2.659. | $CH_3$ | cyclobutyl | $NCH_3COCH_2CH_2CN$ | H | CN | 456.1 | <1e-8M |
| 2.660. | $CH_3$ | cyclobutyl | $N(CH_3)CH_2C_6H_5$ | H | CN | 451.1 | <1e-8M |
| 2.661. | $CH_3$ | cyclobutyl | $NCH_3COCH_2CN$ | H | CN | 442.1 | <1e-8M |
| 2.662. | $CH_3$ | $CH(CH_3)_2$ | $NCH_3COCH_2CN$ | H | CN | 416.1 | <1e-8M |
| 2.663. | $CH_3$ | $CH(CH_3)_2$ | $NCH_3COCH_2CH_2CN$ | H | CN | 430.1 | <1e-8M |
| 2.664. | $CH_3$ | $CH(CH_3)_2$ | $NCH_3COCH_2CH_2CH_2CN$ | H | CN | 444.1 | <1e-8M |
| 2.665. | $CH_3$ | cyclobutyl | $SCH_2CN$ | H | Cl | 412.1 | <1e-8M |
| 2.666. | $CH_3$ | $CH(CH_3)_2$ | $NCH_3COCH_2OCH_2CH_2OCH_3$ | H | CN | 465.1 | <1e-8M |
| 2.667. | $CH_3$ | cyclobutyl | $SCH_2$(5-tetrazolyl) | H | Cl | 455.1 | <1e-8M |
| 2.668. | $CH_3$ | cyclobutyl | $NCH_3COCH_2CH_2CN$ | H | 5-tetrazolyl | 485.2 | <1e-7M |
| 2.669. | $CH_3$ | $CH(CH_3)_2$ | $NCH_3CO(4-COOH—C_6H_4)$ | H | CN | 497.2 | <1e-7M |
| 2.670. | $CH_3$ | cyclobutyl | $CH_2CH_2CH_2CN$ | H | Cl | 408.1 | <1e-8M |
| 2.671. | $CH_3$ | $CH(CH_3)_2$ | $CH_2CH_2CN$ | H | CN | 373.2 | <1e-8M |
| 2.672. | $CH_3$ | cyclobutyl | CN | $CH_2CN$ | H | 371.1 | <1e-8M |
| 2.673. | $CH_3$ | cyclobutyl | Cl | $CH_2CH_2CH_2CN$ | H | 408.1 | <1e-8M |
| 2.674. | $CH_3$ | 3-F-cyclobutyl | Cl | H | Cl | 393.1 | <1e-8M |
| 2.675. | $CH_3$ | $CH(CH_3)_2$ | $CH_2CH_2CH_2CN$ | H | CN | 387.2 | <1e-8M |
| 2.676. | $CH_3$ | 1-F-3-oxetanyl | 2-(5-$COOCH_3$-thienyl) | H | CN | 492.1 | <1e-7M |
| 2.677. | $CH_3$ | cyclobutyl | $CH_2CH_2$-(5-tetrazolyl) | H | Cl | 452.1 | <1e-8M |
| 2.678. | $CH_3$ | cyclobutyl | Cl | $CH_2CH_2CH_2$-(5-tetrazolyl) | H | 452.1 | <1e-8M |
| 2.679. | $CH_3$ | $CH(CH_3)_2$ | 2-(4-$COOCH_3$-thienyl) | H | CN | 460.1 | <1e-8M |
| 2.680. | $CH_3$ | 1-F-3-oxetanyl | 2-(5-COOH-thienyl) | H | CN | 478.1 | <1e-6M |
| 2.681. | $CH_3$ | 1-F-3-oxetanyl | 2-(5-COOH-furyl) | H | CN | 462.1 | <1e-5M |
| 2.682. | $CH_3$ | cyclobutyl | 2-(4-$COOCH_3$-thienyl) | H | CN | 472.1 | <1e-8M |
| 2.683. | $CH_3$ | cyclobutyl | 2-(4-COOH-thienyl) | H | CN | 458.1 | <1e-8M |
| 2.684. | $CH_3$ | cyclobutyl | 2-(4-COOH-furyl) | H | CN | 442.1 | <1e-8M |
| 2.685. | $CH_3$ | $CHFCH_3$ | Br | H | Br | 454.9 | <1e-8M |
| 2.686. | $CH_3$ | $CH(CH_3)_2$ | 2-(4-COOH-thienyl) | H | CN | 446.1 | <1e-7M |
| 2.687. | $CH_3$ | $CHFCH_3$ | CN | H | CN | 349.2 | <1e-7M |
| 2.688. | $CH_3$ | $CH(CH_3)_2$ | $NCH_3COC_2OCH_3$ | H | CN | 421.1 | <1e-8M |
| 2.689. | $CH_3$ | $CH(CH_3)_2$ | $NCH_3COCH_2CH_2CH_2COOH$ | H | $CH_2NH_2$ | 467.1 | <1e-6M |
| 2.690. | $CH_3$ | cyclobutyl | $NCH_3COCH_2CH_2CH_2CN$ | H | 5-tetrazolyl | 499.1 | <1e-6M |
| 2.691. | $CH_3$ | cyclobutyl | $NCH_3CH_2$-(5-tetrazolyl) | H | CN | 443.1 | <1e-7M |
| 2.692. | $CH_3$ | cyclobutyl | $NCH_3CH_2CH_2CN$ | H | 5-tetrazolyl | 457.1 | <1e-6M |
| 2.693. | $CH_3$ | cyclobutyl | $NCH_3CH_2COOH$ | H | CN | 419.1 | <1e-7M |
| 2.694. | $CH_3$ | $CH(CH_3)_2$ | $NCH_3COCH_2CH_2CH_2COOH$ | H | CN | 463.1 | <1e-8M |
| 2.695. | $CH_3$ | cyclobutyl | $NCH_3CH_2CH_2CH_2COOH$ | H | CN | 447.1 | <1e-7M |
| 2.696. | $CH_3$ | cyclobutyl | $NCH_3COCH_2CN$ | H | Cl | 437.1 | <1e-8M |
| 2.697. | $CH_3$ | cyclobutyl | $NCH_3COCH_2CH_2CN$ | H | Cl | 451.1 | <1e-7M |
| 2.698. | $CH_3$ | cyclobutyl | $NCH_3COCH_2CH_2$-(5-tetrazolyl) | H | Cl | 494.1 | <1e-7M |
| 2.699. | $CH_3$ | cyclobutyl | $NCH_3COCH_2$-(5-tetrazolyl) | H | Cl | 480.1 | <1e-7M |
| 2.700. | $CH_3$ | cyclobutyl | $NCH_3COCH_2CH_2CH_2CN$ | H | Cl | 465.1 | <1e-7M |
| 2.701. | $CH_3$ | cyclobutyl | $NCH_3COCH_2CH_2CH_2$-(5-tetrazolyl) | H | Cl | 508.1 | <1e-7M |
| 2.702. | $CH_3$ | $CF_2CH_3$ | H | H | Br | 394.0 | <1e-7M |
| 2.703. | $CH_3$ | 3,3-diF-cyclobutyl | Br | H | Br | 498.9 | <1e-7M |
| 2.704. | $CH_3$ | cyclobutyl | $NHSO_2CH_3$ | H | CN | 424.1 | <1e-7M |
| 2.705. | $CH_3$ | $CH(CH_3)_2$ | 2-(5-$COOCH_3$-thienyl) | H | CN | 460.1 | <1e-8M |
| 2.706. | $CH_3$ | $CH(CH_3)_2$ | 2-(5-$COOCH_3$-furanyl) | H | CN | 444.1 | <1e-8M |
| 2.707. | $CH_3$ | 3,3-diF-cyclobutyl | CN | H | CN | 393.1 | <1e-6M |
| 2.708. | $CH_3$ | cyclobutyl | 5-tetrazolyl | $CH_2CN$ | H | 414.1 | <1e-5M |
| 2.709. | $CH_3$ | cyclobutyl | $NCH_3COCH_2NHCOCH_3$ | H | CN | 460.1 | <1e-7M |
| 2.710. | $CH_3$ | $CH(CH_3)_2$ | $CH_2CH_2CN$ | H | 5-tetrazolyl | 416.1 | <1e-7M |
| 2.711. | $CH_3$ | $CH(CH_3)_2$ | $CH_2CH_2CH_2CN$ | H | 5-tetrazolyl | 430.1 | <1e-7M |
| 2.712. | $CH_3$ | cyclobutyl | H | $NHSO_2CH_3$ | Cl | 334.2 | <1e-7M |
| 2.713. | $CH_3$ | cyclobutyl | $NCH_3CH_2CH_2CH_2NHCOCH_3$ | H | CN | 488.1 | <1e-7M |
| 2.714. | $CH_3$ | 3-F-cyclobutyl | CN | H | CN | 375.1 | <1e-7M |
| 2.715. | $CH_3$ | $CH(CH_3)_2$ | $CH_2CH_2CH_2$-(5-tetrazolyl) | H | 5-tetrazolyl | 473.2 | <1e-6M |
| 2.716. | $CH_3$ | $CH(CH_3)_2$ | $CH_2CH_2$-(5-tetrazolyl) | H | 5-tetrazolyl | 459.1 | <1e-5M |
| 2.717. | $CH_3$ | $CH(CH_3)_2$ | $NCH_3CO(3-COOH—C_6H_4)$ | H | CN | 497.2 | <1e-7M |
| 2.718. | $CH_3$ | cyclobutyl | $NCH_3COCH_2$-(5-tetrazolyl) | H | CN | 485.2 | <1e-7M |
| 2.719. | $CH_3$ | cyclobutyl | $NCH_3SO_2CH_2COOC_2H_5$ | H | CN | 511.2 | <1e-7M |
| 2.720. | $CH_3$ | $CH(CH_3)_2$ | $NCH_3CH_2CH_2COOH$ | H | CN | 449.1 | <1e-7M |
| 2.721. | $CH_3$ | $CH(CH_3)_2$ | $NCH_3COCH_2$-(5-tetrazolyl) | H | CN | 459.1 | <1e-7M |
| 2.722. | $CH_3$ | $CH(CH_3)_2$ | $NCH_3COCH_2CH_2CH_2$-(5-tetrazolyl) | H | CN | 487.1 | <1e-7M |
| 2.723. | $CH_3$ | cyclobutyl | $NCH_3SO_2CH_2CH_2COOCH_3$ | H | CN | 511.2 | <1e-7M |
| 2.724. | $CH_3$ | cyclobutyl | $NCH_3SO_2CH_2CN$ | H | CN | 464.1 | <1e-7M |
| 2.725. | $CH_3$ | $CH(CH_3)_2$ | $NCH_3SO_2CH_2COOC_2H_5$ | H | CN | 499.2 | <1e-7M |

TABLE 2-continued

| No | R¹ | R² | R⁴ | R⁵ | R⁶ | LCMS (M + H) | ED50 SHMT |
|---|---|---|---|---|---|---|---|
| 2.726. | CH₃ | CH(CH₃)₂ | NCH₃SO₂CH₂CH₂COOCH₃ | H | CN | 499.2 | <1e−7M |
| 2.727. | CH₃ | cyclobutyl | NCH₃COCH₂CH₂CH₂-(5-tetrazolyl) | H | CN | 499.2 | <1e−7M |
| 2.728. | CH₃ | CH(CH₃)₂ | NCH₃CH₂CH₂-(5-tetrazolyl) | H | CN | 473.1 | <1e−8M |
| 2.729. | CH₃ | cyclobutyl | NCH₃CH₂CN | H | Br | 481.1 | <1e−8M |
| 2.730. | CH₃ | cyclobutyl | NCH₃COCH₂-(5-tetrazolyl) | H | Br | 524.1 | <1e−8M |
| 2.731. | CH₃ | cyclobutyl | NCH₃SO₂CH₂COOH | H | CN | 483.2 | <1e−7M |
| 2.732. | CH₃ | CH(CH₃)₂ | NCH₃SO₂CH₂COOH | H | CN | 471.1 | <1e−7M |
| 2.733. | CH₃ | cyclobutyl | NHSO₂CF₃ | H | CN | 479.1 | <1e−7M |
| 2.734. | CH₃ | CH(CH₃)₂ | H | CH₂CH₂(5-tetrazolyl) | CN | 416.1 | <1e−7M |
| 2.735. | CH₃ | CH(CH₃)₂ | CH₂-(5-tetrazolyl) | H | 5-tetrazolyl | 445.1 | <1e−5M |
| 2.736. | CH₃ | CH(CH₃)₂ | 5-tetrazolyl | CH₂CH₂CN | H | 416.1 | <1e−6M |
| 2.737. | CH₃ | CH(CH₃)₂ | 5-tetrazolyl | CH₂CH₂CN | H | 459.1 | <1e−6M |
| 2.738. | CH₃ | CH(CH₃)₂ | CH₂-(5-tetrazolyl) | H | CN | 402.1 | <1e−7M |

I.1.B'

TABLE 3

| No | R⁴ | R⁵ | R⁶ | LCMS (M + H) | ED50 SHMT |
|---|---|---|---|---|---|
| 3.1. | H | F | H | 317.2 | |
| 3.2. | H | H | H | 299.2 | |
| 3.3. | F | F | H | 335.2 | <1e−5M |
| 3.4. | F | H | F | 335.2 | <1e−5M |

I

TABLE 4

| No | R¹ | R² | R³ | LCMS (M + H) | ED50 SHMT |
|---|---|---|---|---|---|
| 4.1. | CH₃ | cyclobutyl | 2-(5-(2-thienyl)-thienyl) | 395.1 | <1e−8M |
| 4.2. | CH₃ | 1-F-cyclopropyl | 6-(8-CF₃-2-COOH-quinoline) | 474.0 | <1e−8M |
| 4.3. | CH₃ | cyclobutyl | 2-(5-(2-furyl)-thienyl) | 379.1 | <1e−8M |
| 4.4. | CH₃ | cyclobutyl | 2-(8-CF₃-benzthiazolyl) | 432.0 | <1e−8M |
| 4.5. | CH₃ | cyclobutyl | 7-(5-Cl-2,3-dihydro-1,4-benzodioxinyl) | 399.1 | <1e−8M |
| 4.6. | CH₃ | cyclobutyl | 2-(5-(3-Cl—C₆H₄)-thienyl) | 423.1 | <1e−8M |
| 4.7. | CH₃ | cyclobutyl | 2-(5-Cl-benzofuranyl) | 380.1 | <1e−8M |
| 4.8. | CH₃ | cyclobutyl | 2-(5-(4-F—C₆H₄)-thienyl) | 407.1 | <1e−8M |
| 4.9. | CH₃ | cyclobutyl | 2-(5-Cl-benzothiophenyl) | 397.1 | <1e−8M |
| 4.10. | CH₃ | cyclobutyl | 2-(5-C₆H₅-thienyl) | 389.1 | <1e−8M |
| 4.11. | CH₃ | cyclobutyl | 3-(5-Cl-pyridyl) | 342.1 | <1e−8M |
| 4.12. | CH₃ | cyclobutyl | 5-(7-Cl-5-2,3-dihydrobenzofuranyl) | 383.1 | <1e−8M |
| 4.13. | CH₃ | cyclobutyl | 2-(5-(4-CH₃—C₆H₄)-thienyl) | 403.1 | <1e−8M |
| 4.14. | CH₃ | cyclobutyl | 2-(5-(3-F—C₆H₄)-thienyl) | 407.1 | <1e−8M |
| 4.15. | CH₃ | CH(CH₃)₂ | 7-(5-Cl-2,3-dihydro-1,4-benzodioxinyl) | 387.1 | <1e−8M |
| 4.16. | CH₃ | cyclobutyl | 2-(4-(2-thienyl)-thienyl) | 395.1 | <1e−8M |
| 4.17. | CH₃ | cyclobutyl | 2-(5-(2-F—C₆H₄)-thienyl) | 407.1 | <1e−8M |
| 4.18. | CH₃ | cyclobutyl | 6-(4,4-difluorochromanyl) | 399.0 | <1e−8M |
| 4.19. | CH₃ | cyclobutyl | 6-(2-CH₃-8-CF₃-quinolinyl) | 440.1 | <1e−8M |
| 4.20. | CH₃ | cyclobutyl | 2-(5-(4-Cl—C₆H₄)-thienyl) | 423.1 | <1e−8M |
| 4.21. | CH₃ | cyclobutyl | 2-(5-(3-thienyl)-thienyl) | 394.1 | <1e−8M |
| 4.22. | CH₃ | cyclobutyl | 2-(5-CF₃-benzothiophenyl) | 431.1 | <1e−8M |
| 4.23. | CH₃ | cyclobutyl | 6-(8-F-2,2-dimethyl-chromenyl) | 407.1 | <1e−8M |

TABLE 4-continued

| No | R¹ | R² | R³ | LCMS (M + H) | ED50 SHMT |
|---|---|---|---|---|---|
| 4.24. | CH₃ | cyclobutyl | 2-(4-C₆H₅-thienyl) | 389.1 | <1e−8M |
| 4.25. | CH₃ | cyclobutyl | 5-(2,2-diF-1,3-benzodioxolyl) | 387.0 | <1e−8M |
| 4.26. | CH₃ | cyclobutyl | 2-(5-(4-CF₃—C₆H₄)-thienyl) | 457.1 | <1e−8M |
| 4.27. | CH₃ | cyclobutyl | 2-(5-COOCH₃-thienyl) | 371.1 | <1e−8M |
| 4.28. | CH₃ | cyclobutyl | 2-Benzothienyl | 363.1 | <1e−8M |
| 4.29. | CH₃ | cyclobutyl | 2-(5-(3-CH₃—C₆H₄)-thienyl) | 403.1 | <1e−8M |
| 4.30. | CH₃ | cyclobutyl | 2-(4-COOCH₃-thienyl) | 371.1 | <1e−8M |
| 4.31. | H | cyclobutyl | 6-(8-F-2,2-dimethyl-chromenyl) | 393.0 | <1e−8M |
| 4.32. | CH₃ | cyclobutyl | 5-(2,3-dihydrobenzofuranyl) | 349.1 | <1e−8M |
| 4.33. | CH₃ | cyclobutyl | 2-(4-(3-thienyl)thienyl) | 395.1 | <1e−8M |
| 4.34. | CH₃ | cyclobutyl | 2-(5-(2-CF₃—C₆H₄)-thienyl) | 457.1 | <1e−8M |
| 4.35. | CH₃ | cyclobutyl | 3-(5-CF₃-pyridyl) | 376.0 | <1e−8M |
| 4.36. | CH₃ | cyclobutyl | 2-(6-OCH₃-naphthalenyl) | 387.1 | <1e−8M |
| 4.37. | CH₃ | cyclobutyl | 2-(6-Cl-benzoxazolyl) | 382.1 | <1e−8M |
| 4.38. | CH₃ | cyclobutyl | 2-(4-CF₃-benzothiophenyl) | 431.1 | <1e−8M |
| 4.39. | CH₃ | cyclobutyl | 6-(8-CF₃-2-COOH-quinoline) | 470.1 | <1e−8M |
| 4.40. | CH₃ | 1-F-cyclopropyl | 2-(6-OCH₃-naphthalenyl) | 391.1 | <1e−8M |
| 4.41. | CH₃ | cyclobutyl | 2-(4-(2-furyl)-thienyl) | 379.2 | <1e−8M |
| 4.42. | CH₃ | cyclobutyl | 5-(1-CH(CH₃)₂-benzotriazolyl) | 390.1 | <1e−8M |
| 4.43. | CH₃ | cyclobutyl | 2-(5-(3-CF₃—C₆H₄)-thienyl) | 457.1 | <1e−8M |
| 4.44. | CH₃ | cyclobutyl | 5-(1,3-benzodioxolyl) | 351.2 | <1e−8M |
| 4.45. | CH₃ | cyclobutyl | 2-(4-Cl-benzthiazolyl) | 398.1 | <1e−8M |
| 4.46. | CH₃ | cyclobutyl | 2-benzoxazolyl | 348.1 | <1e−8M |
| 4.47. | CH₃ | cyclobutyl | 2-(4-(3-F—C₆H₄)-thienyl) | 407.1 | <1e−7M |
| 4.48. | CH₃ | cyclobutyl | 5-(2-(CF₃)-1H-benzimidazolyl) | 415.0 | <1e−7M |
| 4.49. | CH₃ | cyclobutyl | 5-(1-CH₃-benzotriazolyl) | 362.0 | <1e−7M |
| 4.50. | CH₃ | cyclobutyl | 2-(5-(3-F-4-OCH₃-5-F—C₆H₂)thienyl) | 455.1 | <1e−7M |
| 4.51. | CH₃ | 1-F-cyclopropyl | 7-(2,3-dihydro-1,4-benzodioxinyl) | 369.0 | <1e−7M |
| 4.52. | CH₃ | cyclobutyl | 2-benzofuranyl | 347.2 | <1e−7M |
| 4.53. | CH₃ | cyclopropyl | 2-(5-(3-CF₃—C₆H₄)-thienyl) | 443.1 | <1e−7M |
| 4.54. | H | cyclobutyl | 2--benzofuranyl | 333.1 | <1e−7M |
| 4.55. | CH₃ | cyclopropyl | 2-(5-C₆H₅-thienyl) | 375.1 | <1e−7M |
| 4.56. | CH₃ | cyclopropyl | 2-(5-(3-F—C₆H₄)-thienyl) | 393.1 | <1e−7M |
| 4.57. | cyclopropyl | cyclopropyl | 2-(4-(3-CF₃—C₆H₄)-thienyl) | 443.1 | <1e−7M |
| 4.58. | CH₃ | cyclobutyl | 2-(4-Br-benzoxazolyl) | 443.0 | <1e−7M |
| 4.59. | CH₃ | 1-F-cyclopropyl | 2-naphthalenyl | 361.1 | <1e−7M |
| 4.60. | CH₃ | cyclopropyl | 2-(4-(3-F—C₆H₄)-thienyl) | 393.1 | <1e−7M |
| 4.61. | CH₃ | C₂H₅ | 2-(4-(2-thienyl)-thienyl) | 369.0 | <1e−7M |
| 4.62. | CH₃ | C₂H₅ | 2-(4-(3-CH₃-2-thienyl)-thienyl) | 397.1 | <1e−7M |
| 4.63. | CH₃ | cyclobutyl | 2-(6-Cl-benzothiophenyl) | 397.1 | <1e−6M |
| 4.64. | CH₃ | cyclopropyl | 2-(4-C₆H₄-thienyl) | 375.1 | <1e−6M |
| 4.65. | CH₃ | C₂H₅ | CH₂CH₂-cyclohexyl | 313.2 | <1e−6M |
| 4.66. | CH₃ | cyclobutyl | 2-(4-COOH-thienyl) | 357.1 | <1e−6M |
| 4.67. | CH₃ | CH(CH₃)₂ | CF₂(3-Cl—C₆H₄) | 379.1 | <1e−6M |
| 4.68. | CH₃ | cyclobutyl | 2-(4-(3-CF₃—C₆H₄)-thienyl) | 457.1 | <1e−6M |
| 4.69. | CH₃ | C₂H₅ | 6-(1,1,4,4-tetramethyltetralinyl) | 391.1 | <1e−6M |
| 4.70. | CH₃ | cyclopropyl | 2-(4-CH₃-thienyl) | 312.2 | <1e−6M |
| 4.71. | CH₃ | C₂H₅ | 5-(1,1,2,3,3-pentamethylindanyl) | 391.1 | <1e−6M |
| 4.72. | CH₃ | C₂H₅ | 6-(3H-1,3-benzoxazol-2-onyl) | 338.1 | <1e−6M |
| 4.73. | C₂H₅ | C₂H₅ | 2-(4-3-CH₃-2-thienyl)-thienyl) | 411.2 | <1e−6M |
| 4.74. | CH₃ | cyclopropyl | 2-(5-Cl-thienyl) | 333.1 | <1e−6M |
| 4.75. | H | 1-F-cyclopropyl | 2-(6-OCH₃-naphthalenyl) | 377.1 | <1e−6M |
| 4.76. | CH₃ | C₂H₅ | CH₂CH₂C₆H₅ | 309.1 | <1e−6M |
| 4.77. | CH₂OH | cyclobutyl | 2-(6-OCH₃-naphthalenyl) | 403.1 | <1e−6M |
| 4.78. | C₂H₅ | cyclopropyl | 2-(5-Cl-thienyl) | 347.1 | <1e−6M |
| 4.79. | CH₃ | C₂H₅ | 2-(4-CH₃-Furyl) | 285.1 | <1e−5M |
| 4.80. | CH₃ | cyclobutyl | 2-(5-COOH-thienyl) | 357.2 | <1e−5M |
| 4.81. | CH₃ | CH(CH₃)₂ | 2-(4-C₆H₅-thienyl) | 377.1 | <1e−5M |
| 4.82. | CH(CH₃)₂ | C₂H₅ | 2-(4-(3-CH₃-2-thienyl)-thienyl) | 425.2 | <1e−5M |
| 4.83. | CHF₂ | cyclopropyl | 2-(5-Cl-thienyl) | 369.1 | <1e−5M |
| 4.84. | CH₃ | 1-F-3-oxetanyl | 5-(2,2-di-F-1,3-benzodioxolyl) | 407.0 | <1e−5M |
| 4.85. | CH₃ | C₂H₅ | CH₂C₆H₅ | 295.1 | |
| 4.86. | CH₃ | C₂H₅ | C₂H₅ | 233.1 | |
| 4.87. | CH₃ | cyclopentyl | cyclopentyl | 313.2 | |
| 4.88. | CH₃ | CH(CH₃)₂ | CH(CH₃)₂ | 261.1 | |
| 4.89. | CH₃ | C₂H₅ | 2-(6-OCH₃-naphthalenyl) | 361.1 | |
| 4.90. | CH₃ | C₂H₅ | 2-(5-Cl-thienyl) | 321.1 | |
| 4.91. | CH₃ | C₂H₅ | 3-(1-CH₃-4-Cl-pyrazolyl) | 319.1 | |
| 4.92. | CH₃ | C₂H₅ | 4-(2-(4-Cl—C₆H₄)-thiazolyl) | 398.1 | |

Determination of the ED50 SHMT was carried out as described hereinunder.

Purification of Arabidopsis thaliana SHMT

The following buffers were used during the purification protocol:

Buffer A (Lysis and Wash Buffer):
20 mM Na-Phosphat (pH 7,4)
500 mM NaCI
40 mM Imidazole
1.0 mM L-Serine
0.5 mM Pyridoxal-5-phosphate
0.5 mM DTT Buffer B (Elution Buffer):
20 mM Na-Phosphat (pH 7,4)
500 mM NaCl
250 mM Imidazole
1.0 mM L-Serine
0.5 mM Pyridoxal-5-phosphate
0.5 mM DTT Cell Lysis All procedures were conducted at 4° C. or on ice. Pellets were suspended in Buffer A containing 1 mg/ml DNAse +Complete EDTA-free protease inhibitor tablet. Cells were lysed using sonication or a French Press device, using standard settings. Lysis was centrifuged at 40000×g for 25 minutes. The supernatant was filtered (0.22 µM) before loading onto a Ni-NTA column.

Purification

A gravity flow column containing Ni-NTA resin was equilibrated with 10 CV Buffer A and loaded with filtered cell lysate. The column was then washed with 10 CV Buffer A. Elution was afforded using Buffer B and collected manually as mini-factions. EDTA was added after elution to a final concentration of 1 mM. Fractions were pooled on the basis of the correct band for SHMT visualised via SDS-PAGE and staining.

Activity Assay:

SHMT Assay Buffer:
50 mM $KH_2PO_4$ (pH 7,4)
2.0 mM NAD+
7.5 mM DTT
0.3 mM Tetrahydrofolic acid
4% DMSO Reaction Start: 20 mM L-Serine The rate of N5,N10-$CH_2$-THF formation catalyzed by SHMT was monitored at 340 nm by coupling with excess N5,N10-$CH_2$-THF dehydrogenase, which converts NAD+to NADH. Reactions were initiated by adding 20 mM L-Serine. Inhibition of initial velocity was determined by adding various inhibitors of the SHMT reaction and monitored as described. Reactions were measured in a Bio Tek micro titer plate reader following the change in absorption with the formation of NADH for 30 mimnutes.

USE EXAMPLES

The herbicidal activity of the pyrazolopyrans of the formula I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this has been impaired by the active ingredients.

For the post-emergence treatment, the test plants were first grown to a height of 2 to 5 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C. The test period extended over 8 to 9 days. During this time, the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A good herbicidal activity is given at values of at least 70 and a very good herbicidal activity is given at values of at least 85.

The plants used in the greenhouse experiments belonged to the following species:

| Bayer Code | Scientific Name | Common Name |
|---|---|---|
| SETFA | Setaria faberi | Giant foxtail |
| AMARE | Amaranthus retroflexus | Redroot pigweed |
| POLCO | Poligonum convolvulus | Wild buckwheat |
| CHEAL | Chenopodium album | lambsquarters |
| GALAP | Galium aparine | catchweed |

At an application rate of 1 kg/ha the compounds 2.112, 2.247, 2.280, 2.281, 2.282, 2.283, 2.335, 2.362, 2.399, 2.400, 2.404, 2.409, 2.414, 2.417, 2.439, 2.470, 2.486, 2.569, 2.611, 2.612, 2.615, 2.616, 2.617, 2.635, 2.662, 2.663, 2.664, 2.675, 2.688, 2.709 and 2.729 applied by the post-emergence method showed good or very good herbicidal activity against at least three of the weeds SETFA, AMARE, POLCO, CHEAL, GALAP.

In particular, the compounds 2.112, 2.247, 2.280, 2.281, 2.282, 2.283, 2.335, 2.362, 2.400, 2.404, 2.414, 2.417, 2.569, 2.611, 2.612 and 2.615 showed very good herbicidal activity against AMARE, POLCO and CHEAL when applied as described above.

The compound 2.399 showed good herbicidal activity against POLCO and very good herbicidal activity against AMARE and CHEAL when applied as described above.

The compound 2.409 showed good herbicidal activity against AMARE and very good herbicidal activity against POLCO and CHEAL when applied as described above.

The compounds 2.439, 2.616, 2.617 and 2.635 showed very good herbicidal activity against AMARE, CHEAL and GALAP when applied as described above.

The compound 2.486 showed good herbicidal activity against CHEAL and very good herbicidal activity against AMARE and GALAP when applied as described above.

The compounds 2.470, 2.662, 2.664 and 2.688 showed very good herbicidal activity against AMARE, CHEAL and SETFA when applied as described above.

Compound 2.663 showed good herbicidal activity against CHEAL and very good herbicidal activity against AMARE and SETFA when applied as described above.

The ompounds 2.675, 2.709 and 2.729 showed good herbicidal activity against SETFA and very good herbicidal activity against AMARE and CHEAL and when applied as described above.

The pharmaceutical activity of the pyrazolopyrans of formula I can be demonstrated by the following in vitro experiments:

For the activity of a pyrazolopyran of the formula I against Mycobacteria an assay described in Hawkins, J. E., Wallace Jr., R. J., Brown, A.; 1991, Antibacterial susceptibility test: Mycobacteria: in A. Balows, W. et al. Manual of Clinical Microbiology, 5th edn., American Society of Microbiology, Washington D.C., can be used.

The invention claimed is:

1. A compound of formula I

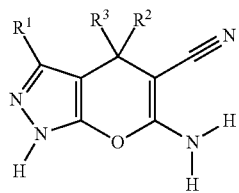

wherein
R$^1$ is hydrogen, C$_1$-C$_6$-alkyl, C$_3$-C$_6$-cycloalkyl, C$_1$-C$_6$-haloalkyl, C$_3$-C$_6$-halocyclo-alkyl, C$_1$-C$_6$-hydroxyalkyl, C$_1$-C$_6$-alkoxy-C$_1$-C$_6$-alkyl, C$_1$-C$_6$-haloalkoxy-C$_1$-C$_6$-alkyl, C$_2$-C$_6$-alkenyl, C$_2$-C$_6$-haloalkenyl, C$_2$-C$_6$-alkynyl, C$_2$-C$_6$-haloalkynyl, hydroxy, C$_1$-C$_6$-alkoxy, C$_1$-C$_6$-haloalkoxy, C$_3$-C$_6$-cycloalkoxy, C$_3$-C$_6$-alkenyloxy, C$_3$-C$_6$-alkynyloxy, C$_1$-C$_6$-alkylthio, C$_1$-C$_6$-alkylamino, or cyano, R$^2$ is C$_2$-C$_6$-alkyl, C$_3$-C$_6$-cycloalkyl, C$_3$-C$_6$-halocycloalkyl, C$_1$-C$_6$-haloalkyl, C$_3$-C$_6$-cycloalkenyl, C$_3$-C$_6$-halocycloalkenyl, C$_1$-C$_6$-hydroxyalkyl, C$_1$-C$_6$-hydroxyhaloalkyl, C$_1$-C$_6$-hydroxycycloalkyl, C$_1$-C$_6$-alkoxy-C$_1$-C$_6$-alkyl, C$_1$-C$_6$-haloalkoxy-C$_1$-C$_6$-alkyl, C$_1$-C$_6$-cyanoalkyl, C$_2$-C$_6$-alkenyl, C$_2$-C$_6$-haloalkenyl, C$_2$-C$_6$-alkynyl, C$_2$-C$_6$-haloalkynyl, C$_1$-C$_6$-alkylthio-C$_1$-C$_6$-alkyl, or 3-7-membered heterocyclyl, 3-7-membered haloheterocyclyl,
wherein each heterocyclyl has one to three nitrogen atoms and/or one or two oxygen and/or sulfur atoms, R$^3$ is phenyl substituted by 1-3 substituents selected from the group consisting of halogen, cyano, C$_1$-C$_6$-alkyl, C$_1$-C$_6$-haloalkyl, C$_1$-C$_6$-alkoxy, C$_1$-C$_6$-haloalkoxy, phenyl, phenyloxy, wherein each of the phenyl groups may be partially or fully halogenated and/or may carry one to three substituents selected from the group consisting of cyano, C$_1$-C$_6$-alkyl, C$_1$-C$_6$haloalkyl, and C$_1$-C$_6$-alkoxy or a tautomer, salt, or mixtures thereof.

2. The pyrazolopyran of claim 1 in form of an agriculturally useful salt.

3. The pyrazolopyran of claim 1 in form of a pharmaceutically acceptable salt.

4. The compound of claim 1, wherein R$^1$ is hydrogen, C$_1$-C$_6$-alkyl, C$_3$-C$_6$-cycloalkyl, C$_1$-C$_6$-haloalkyl, C$_3$-C$_6$-halocycloalkyl, C$_1$-C$_6$-alkoxy-C$_1$-C$_6$-alkyl, C$_1$-C$_6$-haloalkoxy-C$_1$-C$_6$-alkyl, C$_2$-C$_6$-alkenyl, C$_2$-C$_6$-haloalkenyl, C$_2$-C$_6$-alkynyl, and C$_2$-C$_6$-haloalkynyl.

5. The compound of claim 4, wherein R$^1$ is hydrogen, C$_1$-C$_6$alkyl, or C$_3$-C$_6$-cycloalkyl.

6. The compound of claim 5, wherein R$^1$ is C$_1$-C$_6$-alkyl.

7. The compound of claim 1, wherein R$^2$ is C$_2$-C$_6$-alkyl, C$_3$-C$_6$-cycloalkyl, C$_1$-C$_6$-haloalkyl, C$_3$-C$_6$-cycloalkenyl, C$_1$-C$_6$-hydroxyalkyl, C$_1$-C$_6$-alkoxy-C$_1$-C$_6$-alkyl, C$_1$-C$_6$-haloalkoxy-C$_1$-C$_6$-alkyl, C$_2$-C$_6$-alkenyl, C$_2$-C$_6$-haloalkenyl, C$_2$-C$_6$-alkynyl, C$_2$-C$_6$-haloalkynyl, 3-7-membered heterocyclyl, or 3-7-membered haloheterocyclyl.

8. The compound of claim 7, wherein R$^2$ is C$_2$-C$_6$-alkyl, C$_3$-C$_6$-cycloalkyl, C$_3$-C$_6$-cycloalkenyl, 4-6-membered heterocyclyl, or 4-6-membered haloheterocyclyl.

9. The compound of claim 8, wherein R$^2$ is C$_2$-C$_6$-alkyl, C$_3$-C$_6$-cycloalkyl, C$_3$-C$_6$-cycloalkenyl, or 4-6-membered heterocyclyl.

10. The compound of claim 9, wherein R$^2$ is ethyl, i-propyl, cyclobutyl, oxetanyl, cyclopropyl or cyclopentenyl.

11. A herbicidal composition comprising a herbicidal active amount of a pyrazolopyran as defined in claim 1 and auxiliaries customary for formulating crop protection agents.

12. A pharmaceutical composition comprising a pharmaceutically effective amount of a pyrazolopyran as defined in claim 1 and auxiliaries customary for formulating pharmaceuticals.

13. A process for the preparation of a pyrazolopyran of formula I as defined in claim 1, wherein a vinyl-1,1-dinitrile of formula II

1.

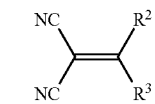

is cyclized with an hydroxypyrazole of formula III,

2.

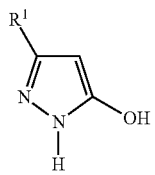

to give the pyrazolopyran of formula I,

3.

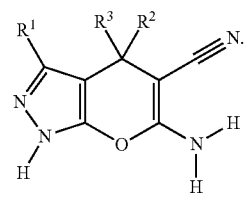

14. A process for the preparation of a herbicidal composition, which comprises mixing a herbicidal active amount of a pyrazolopyran as defined in claim 1 and auxiliaries customary for formulating crop protection agents.

15. A process for the preparation of a pharmaceutical composition, which comprises mixing a pharmaceutically effective amount of a pyrazolopyran as defined in claim 1 and auxiliaries customary for formulating pharmaceuticals.

16. A method of controlling undesired vegetation, which comprises allowing a herbicidal active amount of a compound of claim 1 to act on plants, their environment or on seed, provided that treating of human or animal body is excluded.

17. A method of controlling undesired vegetation, which comprises allowing a herbicidal active amount of a compound of claim 4 to act on plants, their environment or on seed.

18. A method of controlling undesired vegetation, which comprises allowing a herbicidal active amount of a compound of claim 5 to act on plants, their environment or on seed.

19. A method of controlling undesired vegetation, which comprises allowing a herbicidal active amount of a compound of claim 6 to act on plants, their environment or on seed.

20. A method of controlling undesired vegetation, which comprises allowing a herbicidal active amount of a compound of claim 7 to act on plants, their environment or on seed.

21. A method of controlling undesired vegetation, which comprises allowing a herbicidal active amount of a compound of claim 8 to act on plants, their environment or on seed.

22. A method of controlling undesired vegetation, which comprises allowing a herbicidal active amount of a compound of claim 9 to act on plants, their environment or on seed.

23. A method of controlling undesired vegetation, which comprises allowing a herbicidal active amount of a compound of claim 10 to act on plants, their environment or on seed.

* * * * *